(12) United States Patent
Fishman et al.

(10) Patent No.: US 10,940,334 B2
(45) Date of Patent: Mar. 9, 2021

(54) SYSTEMS AND METHODS FOR REAL TIME BEAM SCULPTING INTRA-OPERATIVE-RADIATION-THERAPY TREATMENT PLANNING

(71) Applicant: Sensus Healthcare, Inc., Boca Raton, FL (US)

(72) Inventors: Kalman Fishman, Boca Raton, FL (US); Yonatan Vainer, Giv'Atayim (IL)

(73) Assignee: SENSUS HEALTHCARE, INC., Boca Raton, FL (US)

( * ) Notice: Subject to any disclaimer, the term of this patent is extended or adjusted under 35 U.S.C. 154(b) by 0 days.

(21) Appl. No.: 16/657,228

(22) Filed: Oct. 18, 2019

(65) Prior Publication Data

US 2020/0121957 A1 Apr. 23, 2020

Related U.S. Application Data

(60) Provisional application No. 62/865,338, filed on Jun. 24, 2019, provisional application No. 62/820,452, (Continued)

(51) Int. Cl.
*A61N 5/10* (2006.01)

(52) U.S. Cl.
CPC ......... *A61N 5/1083* (2013.01); *A61N 5/1015* (2013.01); *A61N 5/1039* (2013.01); (Continued)

(58) Field of Classification Search
CPC .......... A61N 2005/1062; A61N 5/1039; A61N 5/1015; A61N 5/1083; A61N 2005/1055; (Continued)

(56) References Cited

U.S. PATENT DOCUMENTS

| 4,401,406 A | 8/1983 | Rovira |
| 5,621,214 A | 4/1997 | Sofield |

(Continued)

FOREIGN PATENT DOCUMENTS

| CN | 204951972 U | 1/2016 |
| DE | 102010009276 A1 | 8/2011 |

(Continued)

OTHER PUBLICATIONS

Extended European Search Report dated Jan. 31, 2020 in EP 17828486.5 filed Jan. 23, 2019.

(Continued)

*Primary Examiner* — Navin Natnithithadha
*Assistant Examiner* — Sunita Reddy
(74) *Attorney, Agent, or Firm* — Fox Rothschild LLP

(57) ABSTRACT

Systems and methods for radiation therapy. The methods comprise: acquiring an image of a treatment area using a Robotic Sculpted Beam Radiation Treatment System ("RCBRTS"); presenting, by a Mobile Computing Platform ("MCP"), the image in a GUI; creating a Real-Time Beam Sculpting Treatment Plan ("RTBSTP") for the patient based on user inputs to MCP via GUI; verifying an expected effectiveness of RTBSTP using a virtual measurement component of GUI (where the virtual measurement component simultaneously provides distance measurements and radiation dose deposition measurements associated with the patient's anatomy and RTBSTP); verifying the final treatment plan using cross sectional 3D view and/or AR view; programming RCBRTS such that radiation therapy delivery will be provided in accordance with RTBSTP; setting RCBRTS so part of it will be inserted into a cavity formed during a medical procedure; and/or performing operations by RCBRTS to apply radiation to the patient.

36 Claims, 60 Drawing Sheets

Related U.S. Application Data filed on Mar. 19, 2019, provisional application No. 62/748,032, filed on Oct. 19, 2018.

(52) U.S. Cl.
CPC ............... *A61N 2005/1052* (2013.01); *A61N 2005/1055* (2013.01); *A61N 2005/1061* (2013.01); *A61N 2005/1062* (2013.01); *A61N 2005/1074* (2013.01)

(58) Field of Classification Search
CPC .... A61N 2005/1074; A61N 2005/1061; A61N 2005/1052
USPC ........................................................ 600/1–8
See application file for complete search history.

(56) References Cited

U.S. PATENT DOCUMENTS

| | | | |
|---|---|---|---|
| 5,635,709 A | 6/1997 | Sliski et al. | |
| 5,635,721 A | 6/1997 | Bardi et al. | |
| 6,144,875 A | 11/2000 | Schweikard et al. | |
| 6,207,952 B1 | 3/2001 | Kan et al. | |
| 6,826,254 B2 | 11/2004 | Mihara et al. | |
| 6,977,987 B2 | 12/2005 | Yamashita et al. | |
| 7,005,623 B2 | 2/2006 | Neuberger et al. | |
| 7,140,771 B2 | 11/2006 | Leek | |
| 7,188,999 B2 | 3/2007 | Mihara et al. | |
| 7,193,220 B1 | 3/2007 | Navarro | |
| 7,200,203 B2 | 4/2007 | Cocks et al. | |
| 7,239,684 B2 | 7/2007 | Hara et al. | |
| 7,263,170 B2 | 8/2007 | Pellegrino | |
| 7,266,176 B2 | 9/2007 | Allison et al. | |
| 7,283,610 B2 | 10/2007 | Low et al. | |
| 7,356,120 B2 | 4/2008 | Main et al. | |
| 7,420,160 B2 | 9/2008 | Delaperriere et al. | |
| 7,505,559 B2 | 3/2009 | Kuduvalli | |
| 7,590,219 B2 | 9/2009 | Maurer, Jr. et al. | |
| 7,605,365 B2 | 10/2009 | Chen et al. | |
| 7,619,374 B2 | 11/2009 | Aoi et al. | |
| 7,656,998 B2 | 2/2010 | Main et al. | |
| 7,686,755 B2 | 3/2010 | Smith et al. | |
| 7,693,257 B2 | 4/2010 | Allison | |
| 7,713,205 B2 | 5/2010 | Fu et al. | |
| 7,894,649 B2 | 2/2011 | Fu et al. | |
| 7,902,515 B2 | 3/2011 | Navarro | |
| 8,050,384 B2 | 11/2011 | Carol et al. | |
| 8,126,114 B2 | 2/2012 | Naylor et al. | |
| 8,139,714 B1 * | 3/2012 | Sahadevan | A61N 5/025 378/63 |
| 8,180,020 B2 | 5/2012 | Kilby et al. | |
| 8,183,522 B2 | 5/2012 | Celi de la Torre et al. | |
| 8,295,435 B2 | 10/2012 | Wang et al. | |
| 8,303,476 B2 | 11/2012 | Francescatti et al. | |
| 8,321,179 B2 | 11/2012 | Simon et al. | |
| 8,332,072 B1 | 12/2012 | Schaible et al. | |
| 8,520,801 B2 | 8/2013 | Henning | |
| 8,559,596 B2 | 10/2013 | Thomson et al. | |
| 8,559,598 B2 | 10/2013 | Kindlein et al. | |
| 8,602,647 B2 | 12/2013 | Navarro | |
| 8,655,429 B2 | 2/2014 | Kuduvalli et al. | |
| 8,660,235 B2 | 2/2014 | Koehler | |
| 8,792,613 B2 | 7/2014 | Gardner et al. | |
| 8,804,901 B2 | 8/2014 | Maurer, Jr. et al. | |
| 8,917,813 B2 | 12/2014 | Maurer, Jr. | |
| 8,929,511 B2 | 1/2015 | van der Veen et al. | |
| 8,934,605 B2 | 1/2015 | Maurer, Jr. et al. | |
| 8,989,846 B2 | 3/2015 | Kuduvalli et al. | |
| 8,995,616 B2 | 3/2015 | van der Veen et al. | |
| 9,036,787 B2 | 5/2015 | de Jager | |
| 9,040,945 B1 | 5/2015 | Hayman | |
| 9,076,201 B1 * | 7/2015 | Negahdar | G06T 7/0012 |
| 9,108,048 B2 | 8/2015 | Maurer, Jr. et al. | |
| 9,168,391 B2 | 10/2015 | Henning et al. | |
| 9,289,268 B2 | 3/2016 | Ramraj et al. | |
| 9,333,031 B2 | 5/2016 | Salahieh et al. | |
| 9,415,239 B2 | 8/2016 | Lubock et al. | |
| 9,561,009 B2 | 2/2017 | Woudstra et al. | |
| 9,616,251 B2 | 4/2017 | Filiberti et al. | |
| 9,724,066 B2 | 8/2017 | Van Der Veen et al. | |
| 9,743,912 B2 | 8/2017 | Fichtinger et al. | |
| 10,327,716 B2 | 6/2019 | Mazin | |
| 10,350,437 B2 | 7/2019 | Fishman | |
| 10,398,519 B2 | 9/2019 | Kim et al. | |
| 10,607,802 B2 | 3/2020 | Fishman et al. | |
| 10,646,726 B2 | 5/2020 | Fishman | |
| 2001/0049475 A1 * | 12/2001 | Bucholz | A61N 5/1049 600/411 |
| 2002/0077545 A1 * | 6/2002 | Takahashi | A61N 5/1049 600/424 |
| 2002/0085668 A1 * | 7/2002 | Blumhofer | A61B 6/547 378/68 |
| 2002/0136439 A1 * | 9/2002 | Ruchala | A61B 6/5235 382/131 |
| 2004/0218721 A1 | 11/2004 | Chornenky et al. | |
| 2004/0227056 A1 | 11/2004 | Neuberger et al. | |
| 2005/0101824 A1 | 5/2005 | Stubbs | |
| 2005/0111621 A1 * | 5/2005 | Riker | G06F 19/3481 378/65 |
| 2005/0276377 A1 | 12/2005 | Carol | |
| 2006/0020195 A1 * | 1/2006 | Falco | G21K 1/046 600/407 |
| 2006/0085053 A1 | 4/2006 | Anderson et al. | |
| 2007/0076851 A1 | 4/2007 | Pellegrino | |
| 2008/0009659 A1 | 1/2008 | Smith et al. | |
| 2008/0170663 A1 * | 7/2008 | Urano | A61N 5/1049 378/65 |
| 2008/0198970 A1 | 8/2008 | Kirshner et al. | |
| 2009/0161826 A1 | 6/2009 | Gertner et al. | |
| 2010/0030463 A1 | 2/2010 | Tomizawa | |
| 2010/0040198 A1 * | 2/2010 | Comer | G21K 1/10 378/65 |
| 2010/0237259 A1 | 9/2010 | Wang | |
| 2010/0274151 A1 | 10/2010 | Chi et al. | |
| 2011/0105822 A1 | 5/2011 | Roeder | |
| 2012/0016175 A1 | 1/2012 | Roberts et al. | |
| 2012/0037807 A1 | 2/2012 | Ujhazy et al. | |
| 2013/0025055 A1 | 1/2013 | Saracen et al. | |
| 2013/0116555 A1 | 5/2013 | Kuzelka | |
| 2013/0131428 A1 * | 5/2013 | Jiang | A61N 5/1031 600/1 |
| 2013/0217947 A1 * | 8/2013 | Fishman | A61N 5/1049 600/1 |
| 2013/0231516 A1 * | 9/2013 | Loo | A61N 5/1043 600/1 |
| 2013/0345718 A1 | 12/2013 | Crawford et al. | |
| 2014/0054465 A1 * | 2/2014 | Berke | A61N 5/1075 250/358.1 |
| 2014/0086388 A1 | 3/2014 | Yamada et al. | |
| 2014/0105361 A1 | 4/2014 | Vogtmeier et al. | |
| 2014/0121501 A1 | 5/2014 | Fichtinger et al. | |
| 2014/0171919 A1 | 6/2014 | Blacker | |
| 2014/0185778 A1 | 7/2014 | Lee et al. | |
| 2014/0205067 A1 | 7/2014 | Carol et al. | |
| 2014/0348288 A1 | 11/2014 | Boyd et al. | |
| 2015/0265306 A1 * | 9/2015 | Andrews | A61B 90/50 606/31 |
| 2015/0265353 A1 * | 9/2015 | Andrews | A61B 18/24 600/411 |
| 2015/0265366 A1 * | 9/2015 | Andrews | A61N 7/00 600/417 |
| 2015/0366546 A1 | 12/2015 | Kamen et al. | |
| 2016/0106387 A1 | 4/2016 | Kahn et al. | |
| 2016/0184032 A1 | 6/2016 | Romo et al. | |
| 2016/0193482 A1 * | 7/2016 | Fahrig | A61N 5/1067 600/1 |
| 2017/0001939 A1 | 1/2017 | Sookraj et al. | |
| 2017/0004267 A1 * | 1/2017 | Svatos | G06F 19/3481 |
| 2017/0296289 A1 * | 10/2017 | Andrews | A61B 34/30 |
| 2017/0368369 A1 * | 12/2017 | Heinrich | A61B 6/12 |
| 2018/0286623 A1 | 10/2018 | Fishman et al. | |
| 2019/0022418 A1 | 1/2019 | Fishman | |
| 2019/0060674 A1 | 2/2019 | Fishman | |

(56) References Cited

U.S. PATENT DOCUMENTS

| | | |
|---|---|---|
| 2020/0038691 A1 | 2/2020 | Fishman et al. |
| 2020/0101325 A1* | 4/2020 | Ollila .................... G06T 7/0012 |
| 2020/0121957 A1 | 4/2020 | Fishman et al. |

FOREIGN PATENT DOCUMENTS

| | | |
|---|---|---|
| RU | 2013147424 A | 4/2015 |
| WO | 2010030463 | 3/2010 |
| WO | 2010065740 A2 | 6/2010 |

OTHER PUBLICATIONS

International Search Report dated Aug. 8, 2018 in PCT/US18/25438.
International Search Report dated Sep. 21, 2017 in PCT/US17/041986.
International Search Report dated Sep. 21, 2017 in PCT/US2017/041986.
International Search Report dated Nov. 26, 2018 in PCT/IB2018/055352.
International Search Report dated Oct. 29, 2018 in PCT/US18/46663.
International Search Report and Written Opinion dated Feb. 19, 2020 in PCT/US19/57191.
Extended European Search Report dated Jul. 9, 2020 in EP 18776334.

* cited by examiner

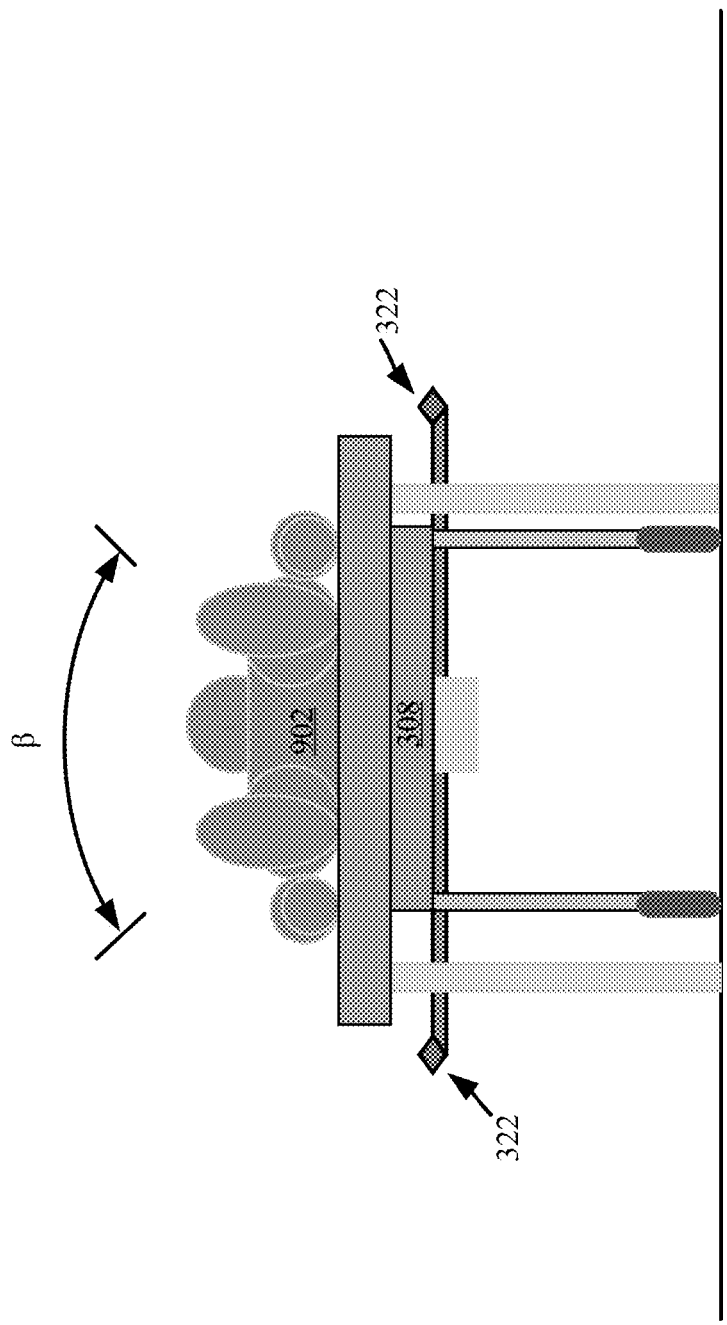

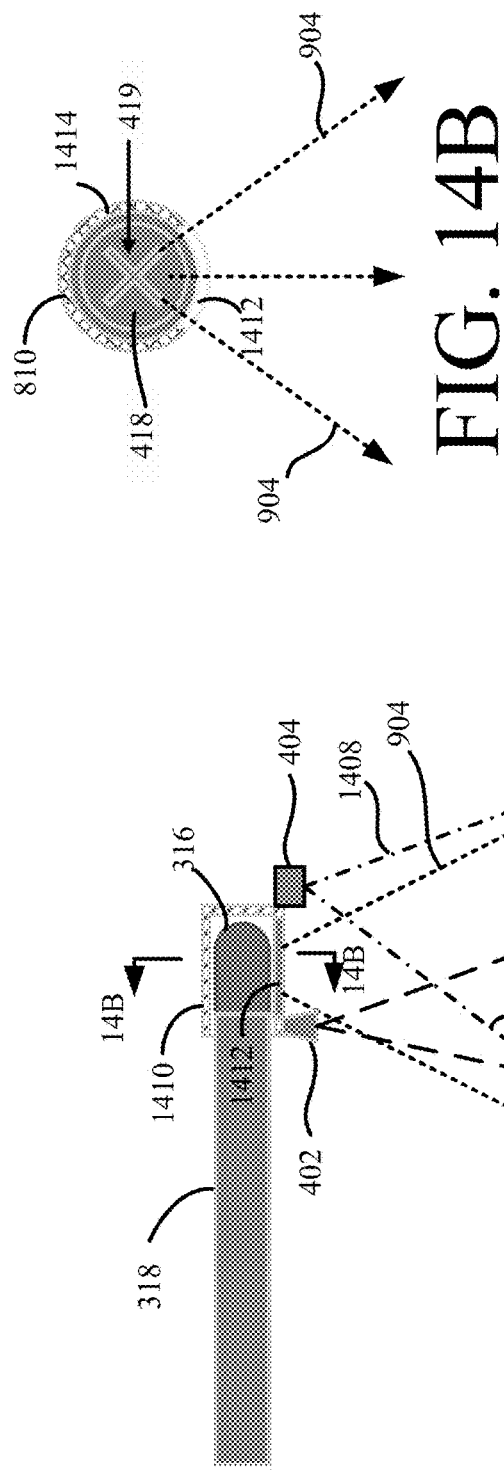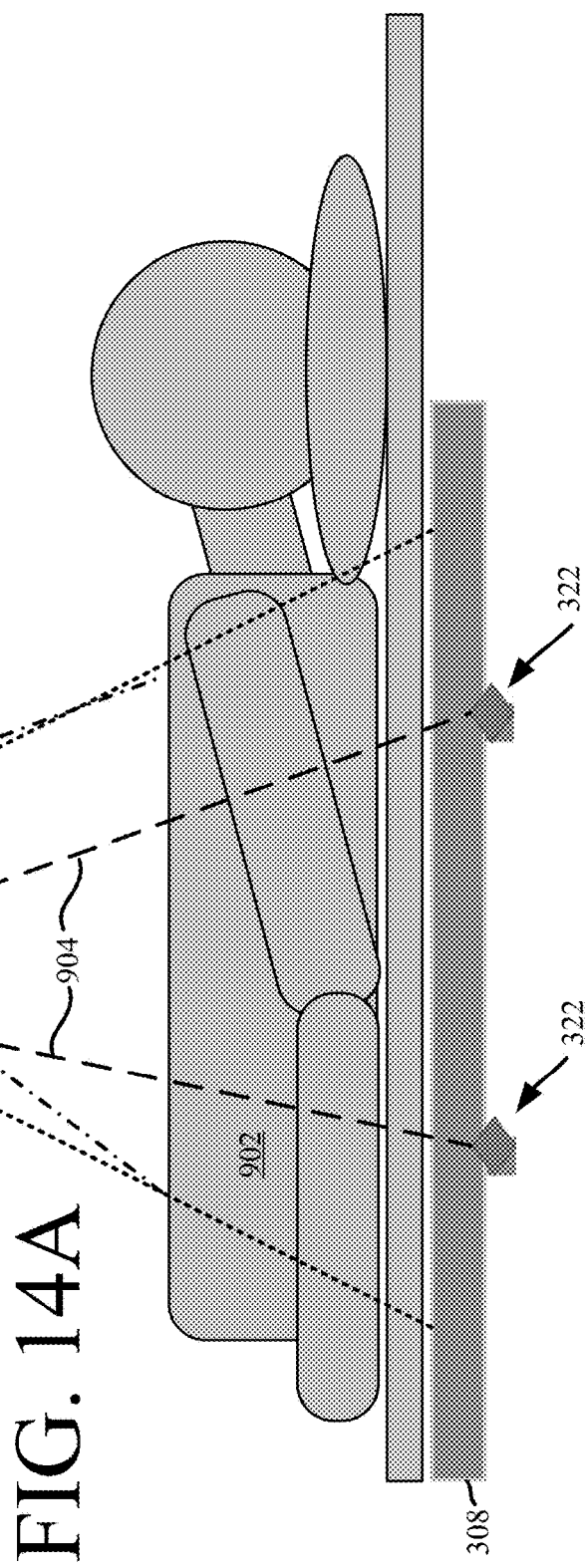

SYSTEMS AND METHODS FOR REAL TIME BEAM SCULPTING INTRA-OPERATIVE-RADIATION-THERAPY TREATMENT PLANNING

CROSS-REFERENCE TO RELATED APPLICATIONS

The present application claims the benefit of U.S. Patent Ser. No. 62/748,032 which was filed on Oct. 19, 2019, U.S. Patent Ser. No. 62/820,452 which was filed on Mar. 19, 2019, and U.S. Patent Ser. No. 62/865,338 which was filed on Jun. 24, 2019. The contents of these application are incorporated herein by reference in their entirety.

BACKGROUND

Statement of the Technical Field

The present disclosure relates generally to computing systems. More particularly, the present disclosure relates to implementing systems and methods for real time beam sculpting intra-operative-radiation-therapy treatment planning.

DESCRIPTION OF RELATED ART

Ionizing radiation is commonly used for different purposes in the medical field. One such application involves medical imaging. There are many different types of medical imaging techniques, each of which uses different technologies and methods to achieve a desired imaging product. Among the most basic of these is conventional radiography or X-ray imaging, which uses ionizing radiation to generate images of the body. In conventional radiography, a single image is recorded for later evaluation. In a Computed Tomography ("CT") systems (which is sometimes referred to as computed axial tomography or CAT), many X-ray images are recorded as a detector moves around the patient's body. A computer reconstructs all the individual images into cross-sectional images or "slices" of internal organs and tissues. With CT, a motorized table moves the patient through a circular opening in the CT imaging system while an X-ray source and a detector assembly within the system rotate around the patient. The X-ray source produces a narrow, fan-shaped beam of X-ray radiation that passes through a section of the patient's body and detectors opposite the X-ray register the X-rays that pass through the patient's body to form a scan. The scan is then used in a process of creating an image. Many different "scans" (at many angles through the patient) are collected during one complete rotation of the detector assembly. For each rotation of the X-ray source and detector assembly, the image data are sent to a computer to reconstruct all of the individual scans into one or multiple cross-sectional images (slices) of the internal organs and tissues. Reconstruction is performed using an inverse Radon transformation.

Digital Tomosynthesis ("DT") is an imaging technique that is somewhat similar to CT. With DT, ionizing radiation (e.g., X-ray radiation) is again used to obtain multiple two-dimensional ("2D") projection images of a subject (e.g., a patient) from a plurality of different angles as an X-ray source moves over a predetermined path. From these projection images, a computer system reconstructs section or slice images of the subject. One distinction between CT and DT is that the range of angles that are used. For example, the total angular range of movement in the case of DT is often less than 40°. In this sense DT may be considered to be a form of limited angle tomography. In conventional DT systems, the image reconstruction is often obtained using a technique known as Filtered Back Projection ("FBP"). As is known, FBP is a type of inverse Radon Transformation.

Another purpose for which ionizing radiation is used in a medical context involves therapeutic treatment of patients. For example, radiation is often used to damage cancer cells so that they will no longer grow and spread within a patient. One example of a particular type of radiation therapy is Intraoperative Radiation Therapy ("IORT"). As is known, IORT is a radiation treatment that is administered to a tumor bed during surgery. This treatment is intended to damage any cancer cells which may remain in the tumor bed after the tumor has been removed. Another type of radiation therapy is Brachytherapy, which is used to treat cancer by positioning a radiation source inside the body of a cancer patient.

SUMMARY

The present disclosure concerns systems and methods for radiation therapy. The method comprises: acquiring at least one image of a treatment area (e.g., a DT scan, a CT scan image, a Magnetic Resonance Imaging ("MRI") image or a Positron Emission Tomography ("PET") scan image) using a robotic sculpted beam radiation treatment system (e.g., an X-ray system); presenting, by a mobile computing platform, at least one image in a Graphical User Interface ("GUI"); creating a real-time beam sculpting treatment plan for the patient based on user inputs to the mobile computing platform via the GUI; verifying an expected effectiveness of the real-time beam sculpting treatment plan using a virtual measurement component of the GUI (where the virtual measurement component simultaneously provides distance measurements and radiation dose deposition measurements associated with the patient's anatomy and the real-time beam sculpting treatment plan); programming the robotic beam sculpting radiation treatment system such that radiation therapy delivery will be provided in accordance with the real-time beam sculpting treatment plan; and/or performing operations by the real-time beam sculpting radiation treatment system to apply radiation to the patient.

In some scenarios, the radiation is applied to the patient prior to when the robotic sculpted radiation treatment system is inserted into the cavity formed during a medical procedure. Additionally or alternatively, at least one image is acquired using an X-ray system. The X-ray system: uses a robotic arm to precisely control a position of an X-ray radiation source relative to the patient; uses an X-ray detector to obtain multiple two-dimensional X-ray projection images of the patient from a plurality of different angles as the X-ray radiation source is moved by the robotic arm over a predetermined path; determines a location of the X-ray radiation source relative to an X-ray detector panel as the X-ray radiation source is moved along the predetermined path by the robotic arm, concurrent with obtaining each said two-dimensional X-ray projection image; and processes the multiple two-dimensional X-ray projection images and the determined locations in a computer system to perform a digital tomo synthesis reconstruction in which section or slice images of the patient are reconstructed from the multiple two-dimensional X-ray projection images that have been acquired. The X-ray radiation source is moved along the predetermined path by selectively controlling a plurality of joint positions associated with a plurality of joints that are respectively associated with the robotic arm.

The X-ray system may further: use the robotic arm to reposition the X-ray radiation source with respect to the patient so that the X-ray radiation source is disposed at a treatment location with respect to the patient; and activate the X-ray radiation source while the X-ray radiation source is at the treatment location so as to carry out a therapeutic X-ray treatment of the patient. The therapeutic X-ray treatment can include, but is not limited to, an intra-operative radiotherapy treatment. The X-ray radiation source may be controlled to produce a first X-ray beam pattern for purposes of obtaining the two-dimensional X-ray projection images, and a second X-ray beam pattern for purposes of the therapeutic X-ray treatment. The X-ray radiation source may alternatively or additionally be controlled to generate an X-ray beam having a first X-ray beam intensity for purposes of obtaining the two-dimensional X-ray projection images, and a second X-ray beam intensity for purposes of carrying out the therapeutic X-ray treatment, the first X-ray beam intensity different as compared to the second X-ray beam intensity. The predetermined path can define an arc which has a central angle of between 15° and 40°.

In some scenarios, a deformable image fusing operation is performed in which a pre-operative volumetric imaging of the patient is deformably fused with the multiple two-dimensional X-ray projection images obtained using DT. The deformable image fusing operation may be performed after the medical procedure has been performed on the patient, but immediately prior to performing an Intraoperative Radiation Therapy procedure on the patient. The deformable image fusing operation comprises fusing the pre-operative volumetric imaging with the intraoperative DT imaging to combine the higher quality pre-operative volumetric imaging, with the lesser quality but more current results obtained using the intraoperative DT imaging. Deep learning or other artificial intelligence techniques can be used to guide the deformable image fusing operation.

In those or other scenarios, the expected effectiveness of the real-time beam sculpting treatment plan is verified using a 3D sculpted beam tool in addition to the virtual measurement component. The 3D sculpted beam tool presents a cross sectional anatomy of the patient together with the isospheres and the radiation source. The rendered 3D isopheres present the distribution of the radiation forming the shape of the beam inside an anatomy of the patient. The 3D sculpted beam tool allows a user to see how a dose or beam will be distributed inside the patient during a treatment. The 3D sculpted beam tool also allows a user to perform fine tuning of the position and orientation of the radiation sources if any correction is required for more accurate delivery of the radiation.

BRIEF DESCRIPTION OF THE DRAWINGS

The present solution will be described with reference to the following drawing figures, in which like numerals represent like items throughout the figures.

FIG. 13 is a drawing which is useful for understanding a range of scan angles which can be used by a robotic X-ray system when performing tomosynthesis operations.

FIGS. 14A and 14B (collectively referred to herein as "FIG. 14") provide a series of drawings that are useful for understanding certain X-ray system components that facilitate DT operations.

DETAILED DESCRIPTION

Figure 1:
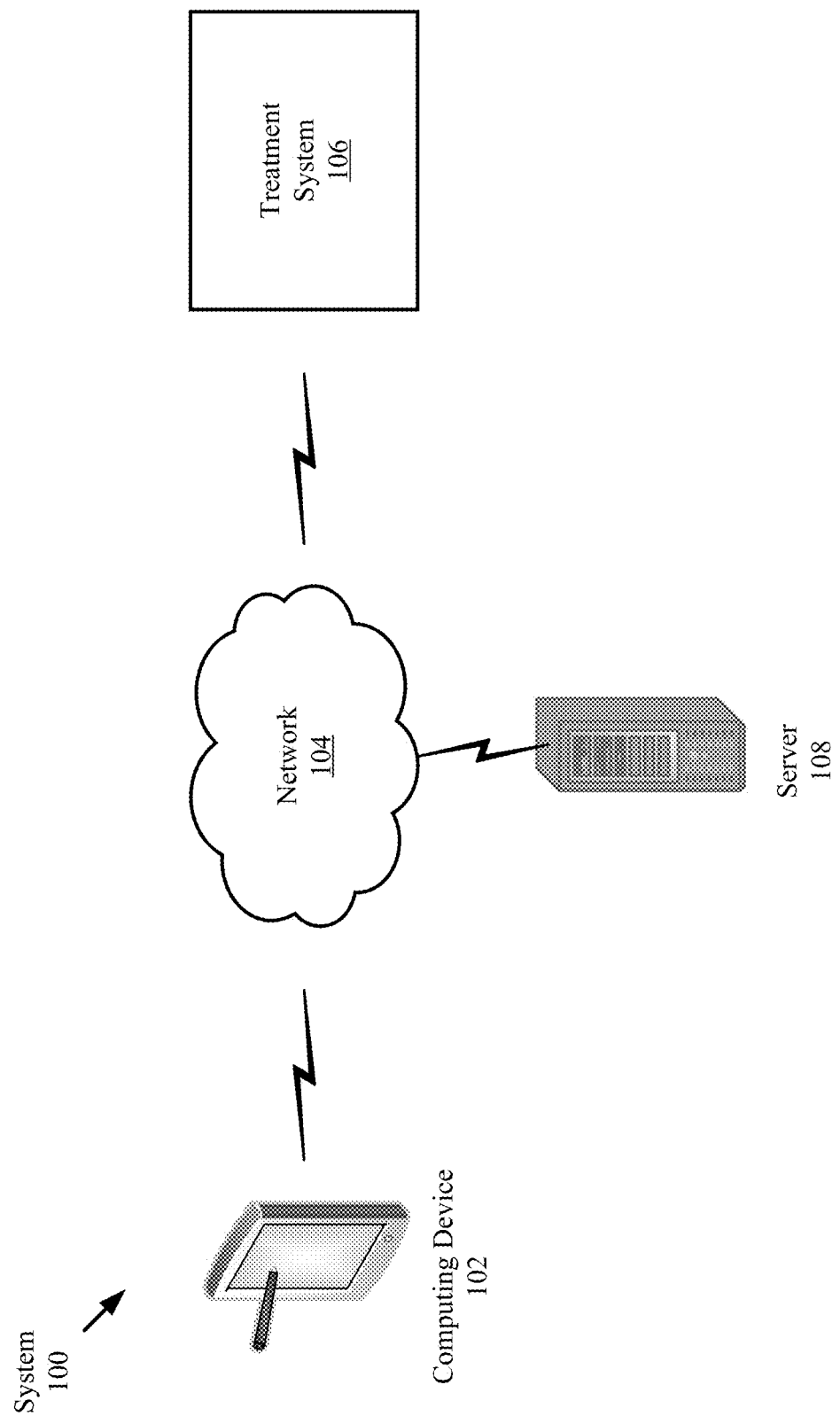
FIG. 1 is an illustration of an illustrative system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present solution may be embodied in other specific forms without departing from its spirit or essential characteristics. The described embodiments are to be considered in all respects only as illustrative and not restrictive. The scope of the present solution is, therefore, indicated by the appended claims rather than by this detailed description. All changes that come within the meaning and range of equivalency of the claims are to be embraced within their scope.

Reference throughout this specification to features, advantages, or similar language does not imply that all of the features and advantages that may be realized with the present solution should be or are in any single embodiment of the present solution. Rather, language referring to the features and advantages is understood to mean that a specific feature, advantage, or characteristic described in connection with an embodiment is included in at least one embodiment of the present solution. Thus, discussions of the features and advantages, and similar language, throughout the specification may, but do not necessarily, refer to the same embodiment.

Furthermore, the described features, advantages and characteristics of the present solution may be combined in any suitable manner in one or more embodiments. One skilled in the relevant art will recognize, in light of the description herein, that the present solution can be practiced without one or more of the specific features or advantages of a particular embodiment. In other instances, additional features and advantages may be recognized in certain embodiments that may not be present in all embodiments of the present solution.

Reference throughout this specification to "one embodiment", "an embodiment", or similar language means that a particular feature, structure, or characteristic described in connection with the indicated embodiment is included in at least one embodiment of the present solution. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

The present solution generally relates to a treatment planning system uniquely designed for a 3D beam sculpting radiotherapy system. The system is comprised of a computational algorithm which is directly derived from the beam sculpting hardware structure and physics, not a generic beam simulator. This algorithm uniquely and precisely simulates the beam particle ballistics as they occur from the specific hardware and physics of the beam sculpting x-ray source. This treatment planning system and method is unique and proprietary to the beam sculpting x-ray source and it intrinsically simulates and renders the cause and effect of an x-ray beam for the accurate simulation of a beam sculpted therapy delivery system. Most current systems model for example an electron striking a tungsten atom thus generating an isotropic x-ray photon release. This algorithm calculates the unique target hardware structure and physics to simulate the 3D beam sculpting effect as influence for example by the position where the electron beam strikes the diamond target and the segments and the collimation effect of the molybdenum scepta.

The present solution is configured for providing real time beam sculpting IORT treatment planning. The present solution is implemented in a system such as that shown in FIG. 1. As shown in FIG. 1, the system 100 comprises a computing device 102 communicatively coupled to a server 108 and/or a treatment system 106 via a network 104 (e.g., an Internet or an Intranet). The network can be a wired network or a wireless network. The computing device 102 includes, but is not limited to, a personal computer, a laptop computer, a smart device, a tablet device (e.g., an iPhone, iPad, Windows® Surface™ or Android® device), or any other portable computing device. The server 108 and treatment system 106 are also communicatively coupled to each other via the network 104. An illustrative architecture for the treatment system 106 will be discussed below in relation to FIG. 2. An illustrative architecture for the computing device 102 and/or server 108 will be discussed below in relation to FIG. 3.

During operation, a user of computing device 102 creates a treatment plan for a patient who is to have radiation therapy in relation to his/her cancer. The expected effectiveness of the treatment plan is verified by the user using a novel feature of the present solution. This novel feature generally comprises a dynamic virtual measurement component (e.g., a ruler) presented on and controlled through widgets of a GUI. The GUI and dynamic virtual measurement component will be discussed below in relation to FIGS. 4-11. Notably, the GUI and dynamic virtual measurement component are provided using a software program installed on the computing device 102 or run through a software program installed on the server 108.

Figure 2:
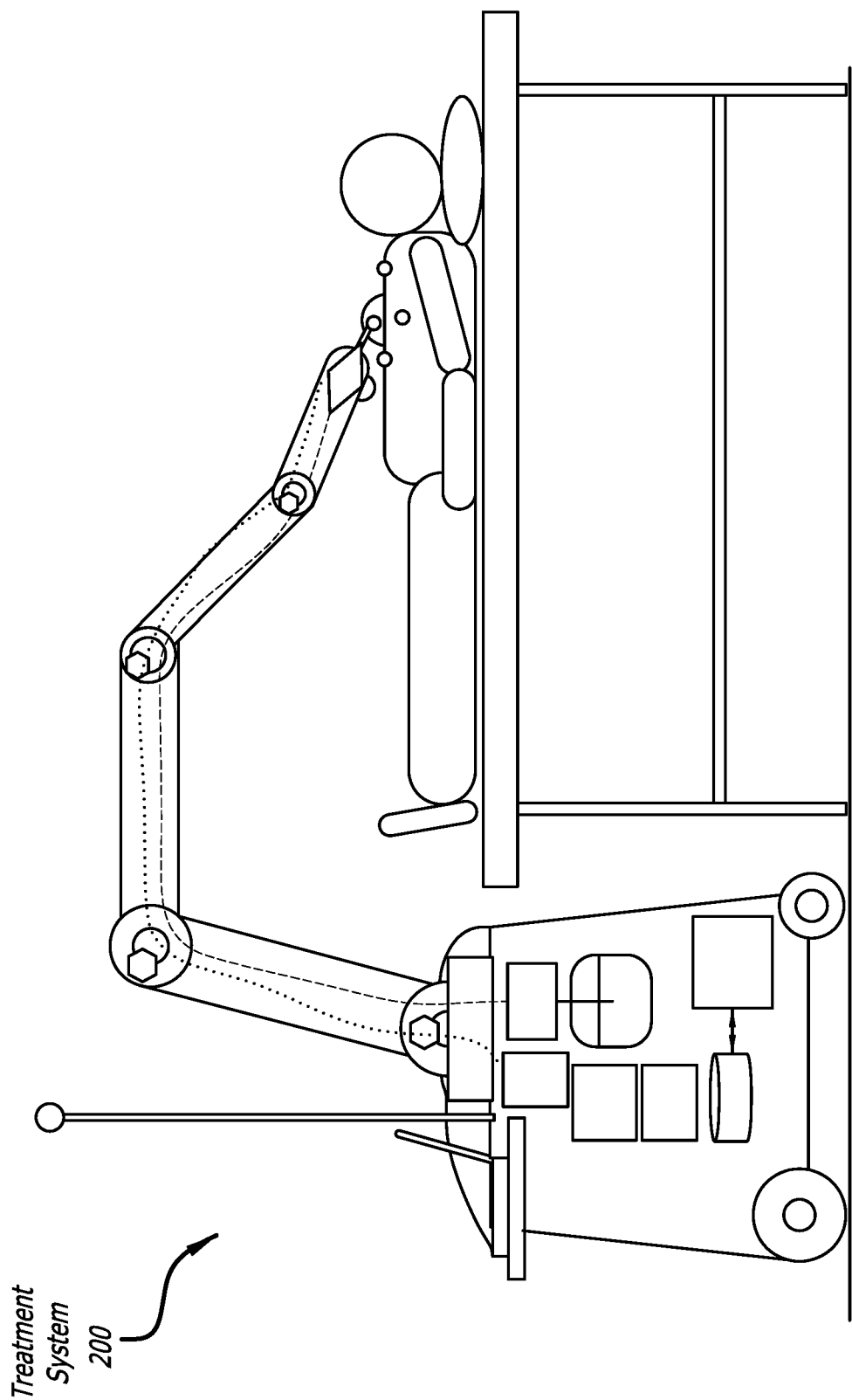
FIG. 2 is an illustration of an illustrative treatment system.

Referring now to FIG. 2, there is provided an illustration of an illustrative treatment system 200 of FIG. 1. Treatment system 106 of FIG. 1 may be the same as or similar to treatment system 200. The treatment system 200 is the same as or substantially similar to that described in U.S. patent application Ser. No. 15/488071 (issued as U.S. Pat. No.

10,596,392), U.S. patent application Ser. No. 15/649361 (issued as U.S. Pat. No. 10,646,726), U.S. patent application Ser. No. 15/941547 (issued as U.S. Pat. No. 10,607,802), U.S. patent application Ser. No. 16/038807 (published as U.S. Publication No. 2019/0022418), and/or U.S. patent application Ser. No. 16/103241 (issued as U.S. Pat. No. 10,350,437). Each of these listed U.S. patent applications are incorporated by reference herein in their entirety.

Another illustrative treatment system 300 will now be discussed in relation to FIGS. 3-15. Treatment system 106 of FIG. 1 may be the same as or similar to treatment system 300. Treatment system 300 comprise X-ray equipment. X-ray equipment is used in the medical field for both imaging and therapeutic purposes. The different nature of these tasks, and the corresponding differences in the technical requirements associated with such equipment, are such that equipment designed for X-ray imaging is not generally used for carrying out therapeutic treatment. However, new advances in robotics and X-ray sources have the potential to facilitate X-ray equipment that can be used for multiple purposes, which can include tasks associated with both tomosynthesis imaging and therapeutic treatment. Accordingly, a robotic X-ray system disclosed herein comprises an X-ray generating system, and includes an X-ray treatment head which is secured to a movable end portion of a robotic arm. X-ray energy is emanated or radiated from the treatment head when the X-ray generating system is activated. In some scenarios, the X-ray treatment head can be disposed at the tip end of an elongated applicator body which is secured to the robotic arm by a base portion. By controlling the position of one or more robotic arm joints, the robotic arm can control a position of the treatment head relative to the patient. The precise and highly adaptable robotic arm, when combined with special features of the X-ray source described herein allow such a system to be used for carrying out medical imaging. With an advanced control system, such imaging can be extended to include digital tomography ("DT"). Further, the highly adaptive nature of the robotic arm and the X-ray source in such an X-ray system can permit the same system to be used for carrying out therapeutic X-ray treatments, including but not limited to IORT.

Figure 3:
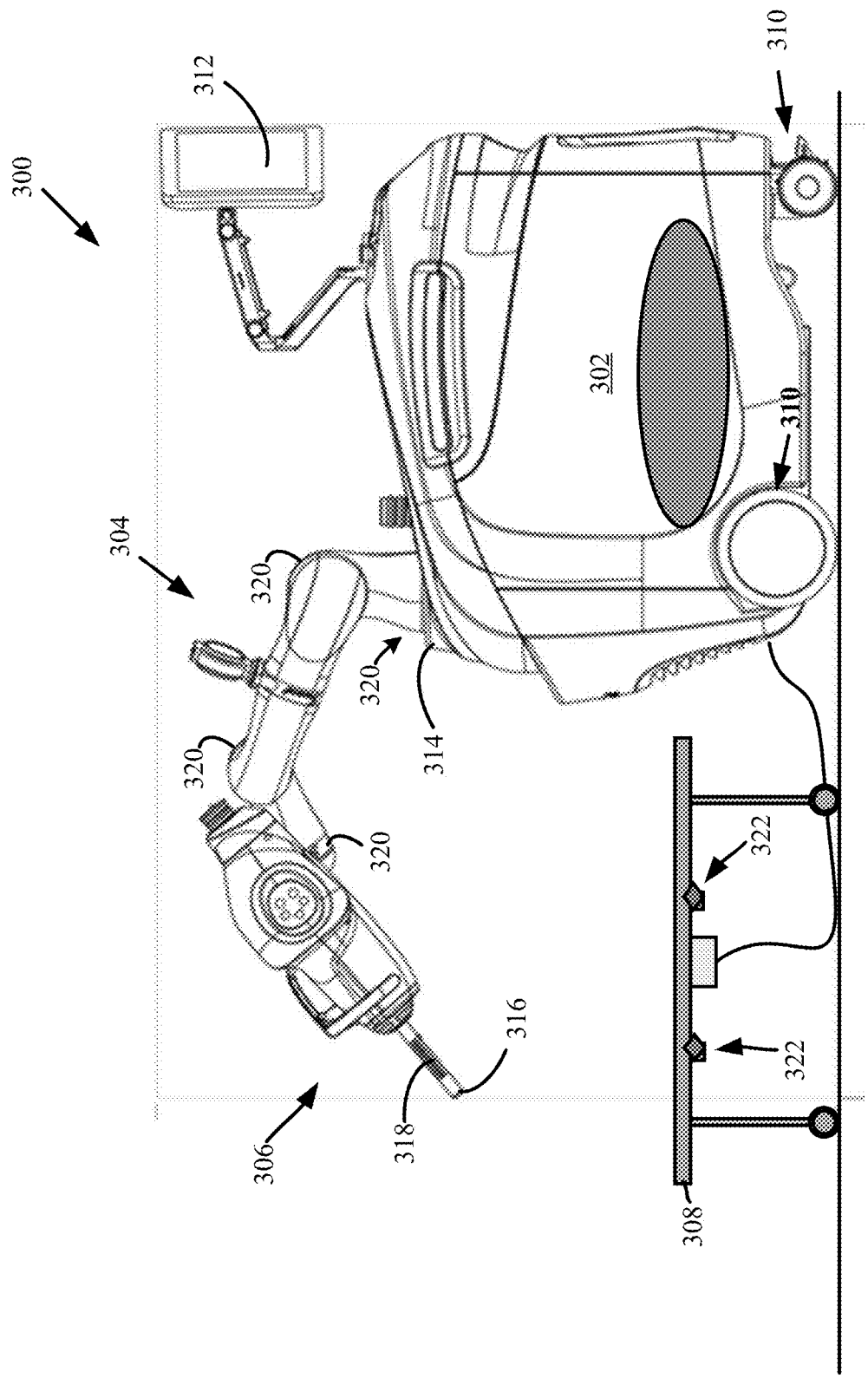
FIG. 3 is a diagram which is useful for understanding an implementation of a robotic X-ray system.

An X-ray system 300 as shown in FIG. 3 comprises a portable base unit or cart 302 (e.g., a movable cart on casters) to which a robotic arm 304 is attached. A head unit 306 is fixed to a first end of the robotic arm 304 distal from a second end of the robotic arm 304 which is attached to the portable base unit 302. The head unit 306 is comprised of an X-ray source which is part of an X-ray system for generating X-ray radiation. A power supply and control unit for the X-ray system (including the robotic arm) can be integrated within the base unit 302.

A solid-state X-ray imaging array 308 is provided as part of the system. In some scenarios, the solid-state X-ray imaging array 308 can be separate with respect to the base unit 302 as shown in FIG. 3. However, in other scenarios, the solid-state X-ray imaging array 308 can be an integral component of the base unit 302 which is extendable from the base unit 302 (e.g., on wheels and/or with a mechanical arm). The solid-state X-ray imaging array 308 is communicatively coupled to the X-ray system 300 by means of a wired or wireless communication link. The purpose of the imaging array will be discussed below in greater detail.

The base unit 302 is advantageously a compact unit such as one with a 30"×48" footprint and can be mounted on casters 310 for ease of maneuverability. The base unit 302 can include a power lead (not shown) for optionally providing power to all of the components housed in or connected to the base unit 102. In this regard, the base unit 302 can contain one or more components of an X-ray system as described in further detail herein with respect to FIG. 4. For example, a display device 312 is shown mounted to the base unit 302 to facilitate a user interface. Likewise, a user interface device (such as a keyboard, mouse or touchpad) can be included in the base unit. In some scenarios, the display device 312 can be associated with a computer workstation (not shown in FIG. 3).

A rigid mechanical mount 314 is provided on the base unit 302 for mounting the robotic arm 304 in a fixed location on the base unit. In a solution presented herein, the robotic arm 304 is used to control a position of the head unit 306 with great precision. Control of the position of head unit 306 also facilitates control over the position of a treatment head 316 from which X-ray energy is emitted during an X-ray session. This controlled position can be a static position in which the treatment head 316 does not move during a time when X-ray radiation is being applied. However, the robotic arm 304 can also facilitate a predetermined motion or movement of the treatment head during an X-ray session. In some scenarios, the movement can occur concurrent with the application of the X-ray radiation. In other scenarios, the application of X-ray radiation can be temporarily interrupted while the robotic arm repositions the treatment head.

In some scenarios, an elongated X-ray applicator body 318 extends from a portion of the head unit 306 to the treatment head 316. The robotic arm 304 is articulated with appropriate robotic joints or articulation members 320 under the control of the control unit. Although not shown in FIG. 3, more or fewer articulation members 320 can be provided at different points of robotic arm 304. Such articulation members 320 can increase or decrease a number of degrees of freedom for placing, orienting and moving the X-ray treatment head 316. Moreover, the number of articulation members illustrated in FIG. 3 is solely for ease of illustration. The present disclosure contemplates that the any number of articulation points can be provided so as to provide any number of degrees of freedom in robotic arm 304 as may be required for dynamically positioning and orienting the X-ray treatment head 316 with respect to the patient.

In some scenarios, the robotic arm 304 is a robotic system that provides freedom of movement about multiple orthogonal axes (e.g., up to seven axes) and includes lightweight force and torque sensors to ensure safe operation with humans without the need for a safety fence. Illustrative robots of this kind are commercially available from various sources. For example, KUKA Roboter GmbH of Augsburg Germany ("KUKA") manufactures a line of direct Human-Robot Collaboration ("HRC") capable lightweight robots which are suitable for direct human-robot interaction. These robots include the LBR iiwa model and/or the LBR iisy model produced by KUKA. Robots of this kind are well suited for the delicate operations described herein because they include high-grade joint torque sensors included in all six axes, which can detect the slightest of external forces resulting from contact with objects, and can respond by immediately reducing a level of force and speed associated with robot movements. The robotic arm 304 will precisely maintain a position of the X-ray treatment head relative to a subject patient. In order to accomplish this result, the robotic arm can move along multiple motion axes (e.g., up to seven motion axes) to maintain a relative position of the X-ray treatment head at a particular location and/or along a predetermined movement path.

In some scenarios, the X-ray generating system is distributed between the base unit 302 and the head unit 306. A power and/or control signal conduit (not shown in FIG. 3) can facilitate communication of power and/or control signals between the base unit 302 and the head unit 306. These signals can be used to control and facilitate operation of the X-ray generating system. In some scenarios, high voltage cables, fluid conduits, and control circuitry may not be included as part of the robotic arm, but can instead comprise a separate control cable bundle which simply attaches to the X-ray treatment head.

Figure 4:
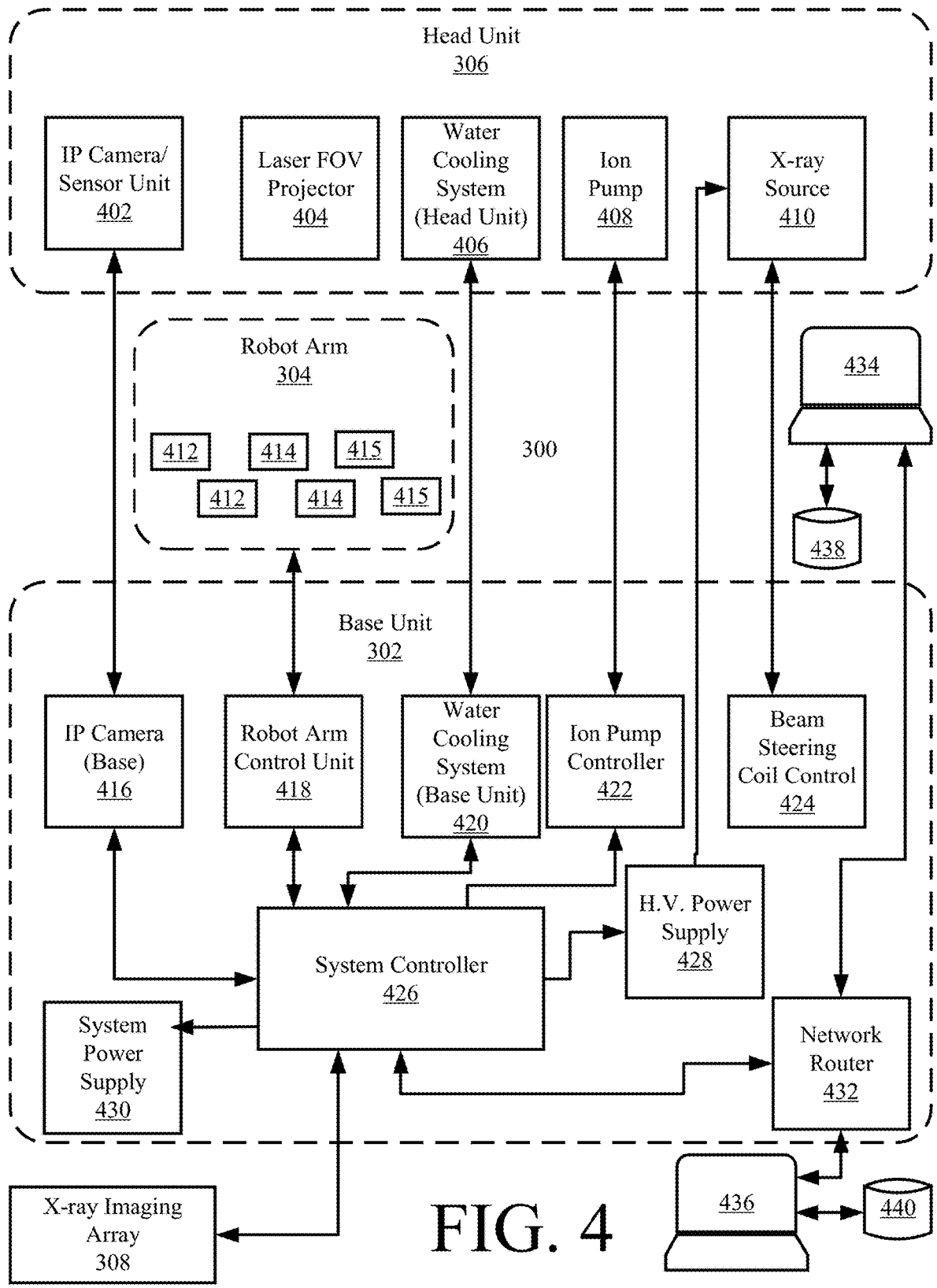
FIG. 4 is a block diagram that is useful for understanding an architecture of a robotic X-ray system.

Referring now to FIG. 4 there is shown a high level block diagram representation of the X-ray system 300 which is useful for understanding certain aspects of a solution presented herein. The block diagram shows the main subsystems including the base unit 302, the robot arm 304, and the head unit 306 as described in relation to FIG. 3, and includes details of certain components that can be distributed among these various subsystems. For example, the base unit can be comprised of a system power supply 430, an Internet Protocol ("IP") camera base component 416, and a robot arm control unit 418. The base unit 302 includes various base unit components associated with an X-ray generating system. For example, the base unit components include a high voltage power supply 428, an ion pump controller 422, a beam steering coil control 424, and a water cooling system base unit portion 420. In some scenarios, the water cooling system uses water as a coolant to carry heat away from certain components of the X-ray generating system described herein. Although referred to herein as a water cooling system, it should be understood that water is just one example of a suitable coolant which can be used for this purpose. As will be understood by those skilled in the art, other types of fluid coolants can also be used for this purpose.

A system controller 426 is provided to control the overall operation of the X-ray system 300. As such, the system controller 426 is communicatively connected to one or more of the IP camera base component 416, robot arm control unit 418, water cooling system base unit portion 420, the ion pump controller 422, system power supply 430, and the high voltage power supply 428.

The head unit 306 can include various head unit components associated with the X-ray generating system including a water cooling system head unit portion 306, and an ion pump 308. As explained below in further detail, the ion pump may comprise a part of an Electron Beam Generator ("EBG") for an X-ray source 410. The X-ray source 410 includes electron beam steering coils (not shown in FIG. 4) which are used to help shape an X-ray beam. The ion pump 408 operates under the control of the ion pump controller 422, and the X-ray source 410 operates under the control of the beam steering coil control unit 424. In some scenarios, the X-ray source 410 is configured so that X-ray radiation is emitted from the treatment head 316 disposed on the movable end of the robotic arm 304. The X-ray generating system described herein can be configured to facilitate treatment of a patient in accordance with various treatment methods (e.g., IORT and/or Brachytherapy methods) which are now known or known in the future.

The water cooling system head unit portion 406 operates cooperatively with, and under the control of, the water cooling system base unit portion 420. For example, the water cooling system head unit portion 406 can be configured to facilitate a flow of cooling water (or any other suitable coolant) to one or more of the components associated with the X-ray generating system. The head unit 306 also includes an IP camera/sensor head unit 402, a laser Field of View ("FOV") projector component 404. The IP camera/sensor head unit 402 is configured to capture one or more images which are useful for facilitating an X-ray imaging and/or treatment session. The purpose and function of the IP camera/sensor system (402, 416) will be described in greater detail below.

Communication of data, fluids and/or control signals between the various components of X-ray system 300 that are disposed in the base unit 302 and the head unit 306 can be facilitated by cables and/or conduits that are routed internally through the robotic arm 304 or externally thereof. For purposes of clarity, these cables and/or conduits are shown as being external of the robotic arm in FIG. 3, but it should be understood that the solution is not limited in this regard.

The robot arm 304 can include a plurality of robot arm actuators 412 which determine a position of articulation members 320 under the control of the robot arm control unit 418. Although not shown in FIG. 3, more or fewer robot arm actuators 412 can be provided in the robotic arm 304 to facilitate movement with respect to each of the articulation members. In some scenarios, the robotic arm includes a plurality of joint position sensors 414. These position sensors are advantageously associated with the robot arm joints 320. In some scenarios, this position information can be used by the system controller 426 to determine a pose of the robotic arm. As explained below in further detail, this information can be useful for determining an exact location and orientation of the X-ray radiation treatment head 316 relative to the X-ray detector panel and/or a person undergoing therapeutic radiation treatment. The robotic arm 304 also optionally include one or more force sensors 415 for determining or sensing a force exerted on the robotic arm 304. These force sensors can be useful to facilitate position tracking, whereby a position of the robotic arm is automatically adjusted in response to patient movements (such as respiratory movement) which occur during an X-ray treatment session.

The X-ray system 300 can be controlled by a computer workstation 434. To facilitate such control, the computer workstation 434 is configured to communicate with the system controller 426 by means of a suitable high speed data connection. The computer workstation includes an operating system and suitable application software to facilitate the various systems and methods described herein. Computer workstations are well-known in the art, and therefore will not be described here in detail. However, it should be noted that the computer workstation includes, but is not limited to, a computer processor, a memory, a display screen (such as display screen 312 of FIG. 3) which may be a touchscreen, one or more user interface components (such as a keyboard and/or a pointing device (e.g., a mouse)), and a network interface component to facilitate communications with the X-ray system 300. The X-ray system 300 can also be operatively coupled to a Radiation Therapy Planning ("RTP") computer workstation 436 which is configured to facilitate therapeutic radiation treatment planning. Data communications among the X-ray system 300, and external computer systems such as the workstation 434 and RTP workstation 436 can be facilitated by a network router 432.

The various components comprising the X-ray generating system in system 300 can be controlled so that they are selectively optimized for a therapeutic radiation treatment and/or certain patient imaging operations as hereinafter described. In some scenarios, a Superficial Radiation Therapy ("SRT") type of X-ray source can be used for this purpose. As will be appreciated, an SRT type of X-ray unit produces low energy X-rays that is suitable for this purpose. In other scenarios, a therapeutic treatment can involve Brachytherapy.

In some scenarios, the solid-state X-ray imaging array 308 can be used to capture 2D X-ray projection images of a subject patient when the patient is exposed to X-rays produced by the X-ray source 410. These 2D X-ray projection images can be obtained with the X-ray source at a plurality of different locations relative to the patient. In such a scenario, the 2D X-ray projections images are captured with the X-ray source 410 positioned at a plurality of different angles (relative to the patient) as the X-ray radiation source (e.g., the X-ray tube) is moved by the robotic arm 304 over a predetermined path. Solid-state X-ray imaging arrays are well-known in the art, and therefore will not be described here in detail. However, it should be understood that captured 2D X-ray projection images can be communicated to an on-board processing element (such as system controller 426), a separate image processing computer (e.g., workstation 434 and/or RTP workstation 436) and/or a data storage device (not shown) for later processing.

The X-ray system 300 is controlled and operated by the system controller 426. System controller 426 includes, but is not limited to, a central computer with a motherboard running operation and control software that allows the system controller 426 to control, communicate, and monitor the various sub-components and modules of the X-ray system 300. This achieves harmonious functionality between the main clinical components of the X-ray system 300 including the X-ray generating components 408, 410, 422, 424 and the robotic arm 304.

The system controller 426 is in communication with a machine-readable medium which can be static memory on which is stored one or more sets of instructions (e.g., software) embodying any one or more of the methodologies or functions described herein, including those methods illustrated herein. The instructions may also reside, completely or at least partially, within the system data repository, static memory, or within the processor, or a combination thereof, during execution thereof by the X-ray system 300. The system data repository, patient data repository and processor also may constitute machine-readable media.

Patient-related data and treatment parameters, such as patient records, treatment session details, and disease documentation and photos can be stored in one or more patient data storage devices 440 which are communicatively coupled to the RTP workstation 436. System-related data and parameters, such as the system log, x-ray calibration data, and system diagnostics results can be stored in a data repository 438 associated with workstation 434. The patient data repository and the system data repository can be discrete devices or physically combined. Both data repositories can be mirrored and backed up to a secured and encrypted HIPAA-compliant cloud storage medium.

Figure 5:
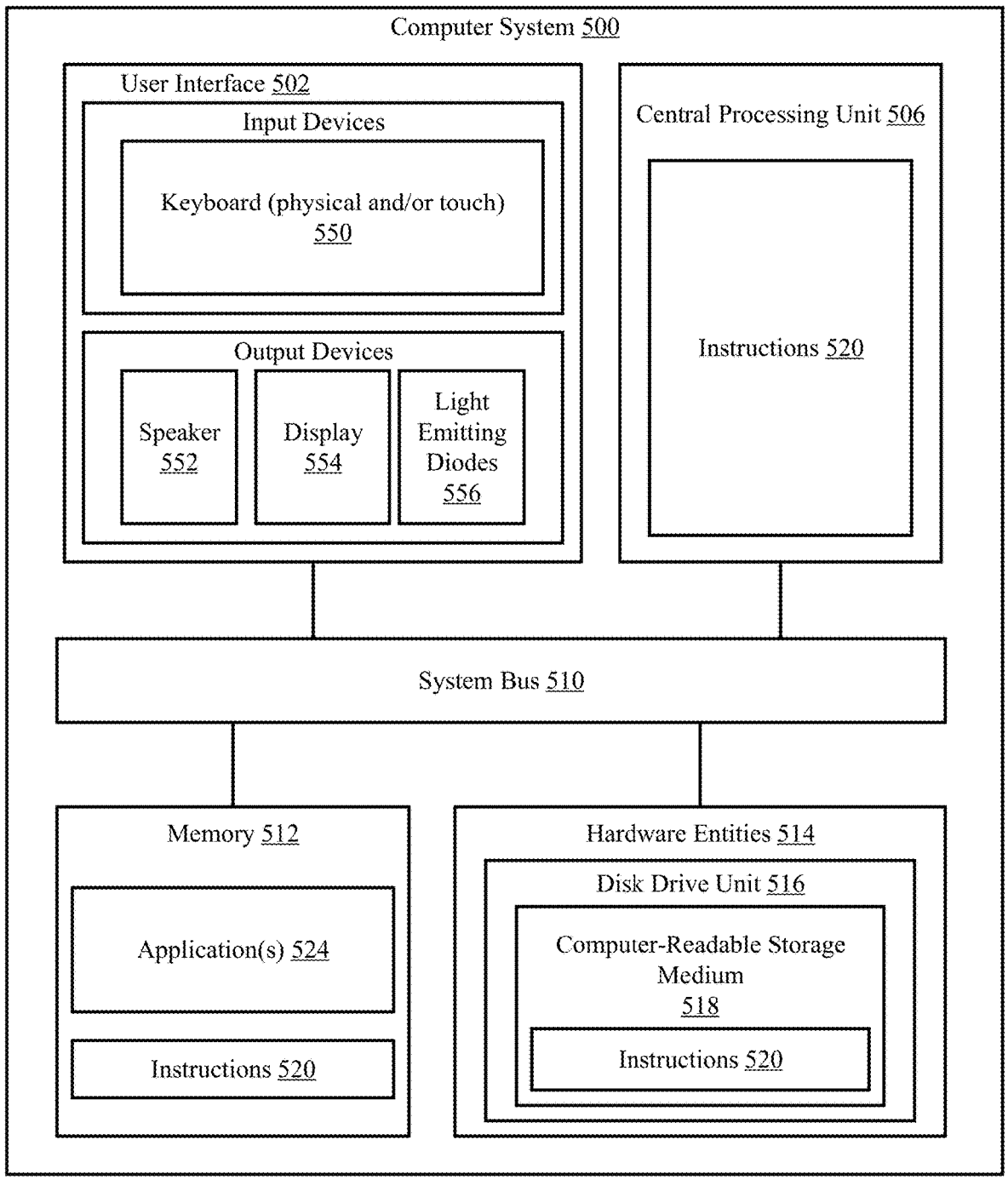
FIG. 5 is a block diagram which is useful for understanding certain aspects of a control system which can be used to perform certain processing operations of associated with a robotic X-ray system as described herein.

Referring now to FIG. 5, there is provided an illustration of an illustrative computer system 500 which can serve as the system controller 426 for controlling a robotic X-ray system 300 as described herein. The computer system 500 is also sufficient to understand an illustrative architecture associated with one or more of the workstations which are described herein. The computer system 500 can include, but is not limited to, machines (or computing devices) running a suitable operating system (e.g., Windows, Linux, macOS or other type of operating system now known or known in the future). Such machines (or computing devices) are well known in the art, and will not be described in detail herein. Still, it should be understood that such machines are modified to implement all or a portion of the methods described herein. Such modifications can include software modifications, hardware modification or a combination of both.

Computer system 500 may include more or less components than those shown in FIG. 5. However, the components shown are sufficient to disclose an illustrative embodiment implementing the present solution. The hardware architecture of FIG. 5 represents one representative computing device configured to facilitate the operations described herein.

Some or all the components of the computer system 500 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 5, the computer system 500 comprises a user interface 502, a Central Processing Unit ("CPU") 506, a system bus 510, a memory 512 connected to and accessible by other portions of computing device 500 through system bus 510, and hardware entities 514 connected to system bus 510. The user interface includes, but is not limited to, input devices and output devices, which facilitate user-software interactions for controlling operations of the computing device 500. The input devices include, but are not limited, a physical and/or touch keyboard 550. The input devices are connected to the computing device 500 via a wired or wireless connection (e.g., a Bluetooth® connection). The output devices include, but are not limited to, a speaker 552, a display 554, and/or light emitting diodes 556.

At least some of the hardware entities 514 perform actions involving access to and use of memory 512, which can be a Random Access Memory ("RAM"), a disk drive and/or a Compact Disc Read Only Memory ("CD-ROM"). Hardware entities 514 can include a disk drive unit 516 comprising a computer-readable storage medium 518 on which is stored one or more sets of instructions 520 (e.g., software code) configured to implement one or more of the methodologies, procedures, or functions described herein. The instructions 520 can also reside, completely or at least partially, within the memory 512 and/or within the CPU 506 during execution thereof by the computing device 500. The memory 512 and the CPU 506 also can constitute machine-readable media. The term "machine-readable media", as used here, refers to a single medium or multiple media (e.g., a centralized or distributed database, and/or associated caches and servers) that store the one or more sets of instructions 520. The term "machine-readable media", as used here, also refers to any medium that is capable of storing, encoding or carrying a set of instructions 520 for execution by the computer system 500 and that cause the computer system 500 to perform any one or more of the methodologies of the present disclosure.

Figure 6:
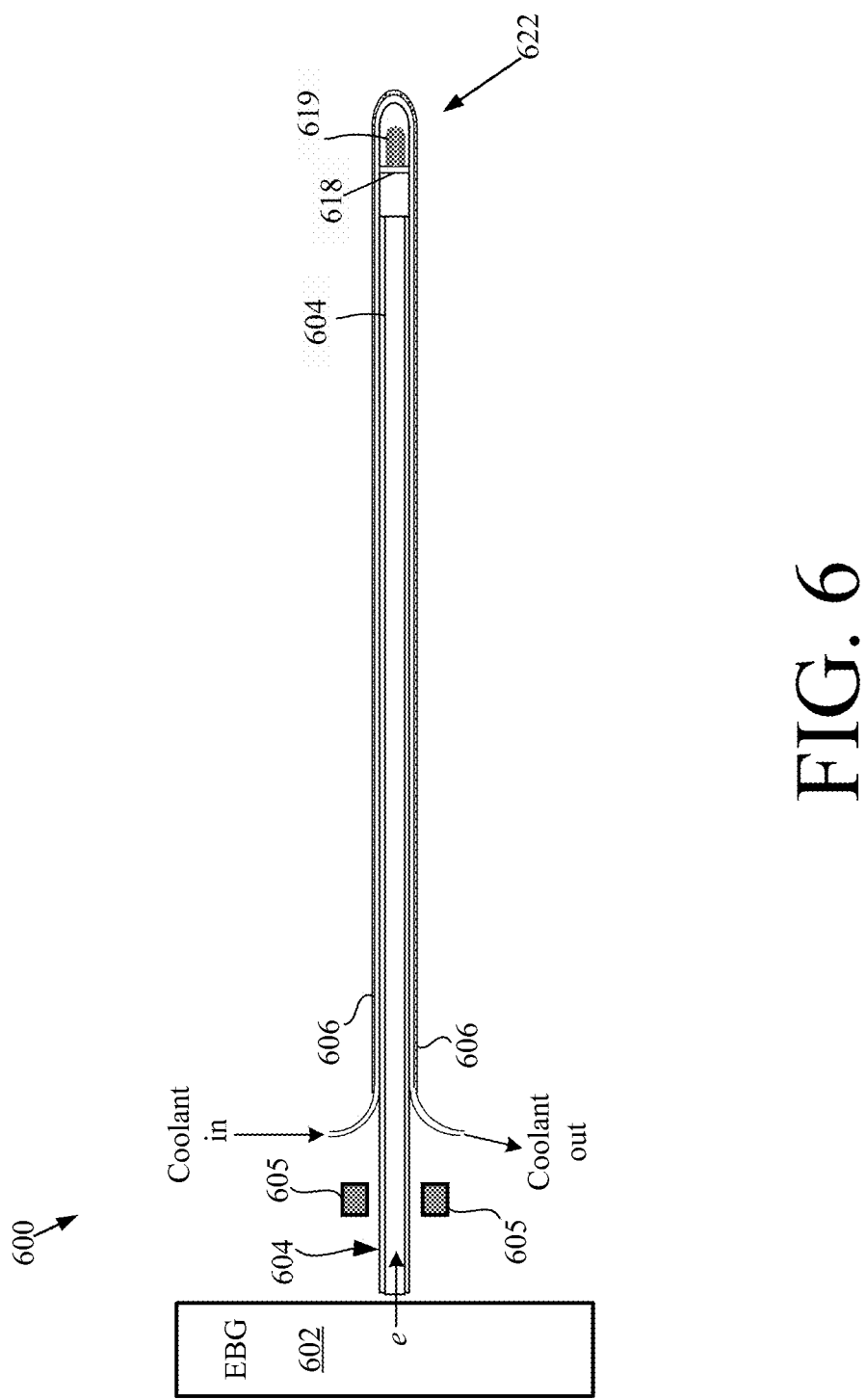
FIG. 6 is a schematic diagram that is useful for understanding a controlled beam X-ray source that can be used with the robotic X-ray system.

Turning now to FIG. 6, there is shown an illustrative X-ray source 600 which can be used with the robotic X-ray system described herein. This type of X-ray source is described in detail in U.S. patent application Ser. No. 15/941,547, filed Mar. 30, 2018 and entitled "Three-Dimensional Beam Forming X-ray Source" (issued as U.S. Pat. No. 10,607,802). The disclosure of which is incorporated herein by reference. Briefly, the system comprises an EBG 602 and a drift tube 604 which is supported on an end of the robotic arm distal from the base. The EBG 602 comprises an ion pump (e.g., ion pump 408 of FIG. 4). An X-ray generating element 622 resides at an end of the drift tube 604, distal from the EBG. In some scenarios, the EBG 602 resides in a head unit (e.g., head unit 306 of FIG. 3) as described herein. For example, the EBG 602 can reside in the head unit attached to a robotic arm (e.g., robotic arm 304 of FIG. 3). The elongated applicator body (e.g., applicator body 318 of FIG. 3) is comprised of the drift tube 604. The treatment head comprises the X-ray generating element 622. The presents solution is not limited to the particulars of this example.

The drift tube 604 is comprised of a conductive material such as stainless steel. Alternatively, the drift tube 604 is comprised a ceramic material such as alumina or aluminum nitride with a conductive inner lining. The hollow inner portion of the drift tube is maintained at a vacuum pressure (e.g., a suitable vacuum pressure for the systems described herein can be in the range below about 10-5 torr or particularly between about $10^{-9}$ torr to $10^{-7}$ torr).

In the X-ray source shown in FIG. 6, electrons e generated by the ion pump form an electron beam as they are accelerated by the EBG toward an X-ray target 618. These electrons have significant momentum when they arrive at the entry aperture of the drift tube. The hollow interior of the drift tube is maintained at a vacuum pressure and at least the inner lining of the drift tube is maintained at ground potential. Accordingly, the momentum imparted to the electrons by EBG 602 continues to ballistically carry the electrons down the length of the drift tube at very high velocity (e.g., a velocity approaching the speed of light) toward the X-ray target 618. As the electrons are traveling along the length of the drift tube 604, they are no longer electrostatically accelerated. When the electrons impact upon the X-ray target 618, X-rays are generated.

Figure 7:
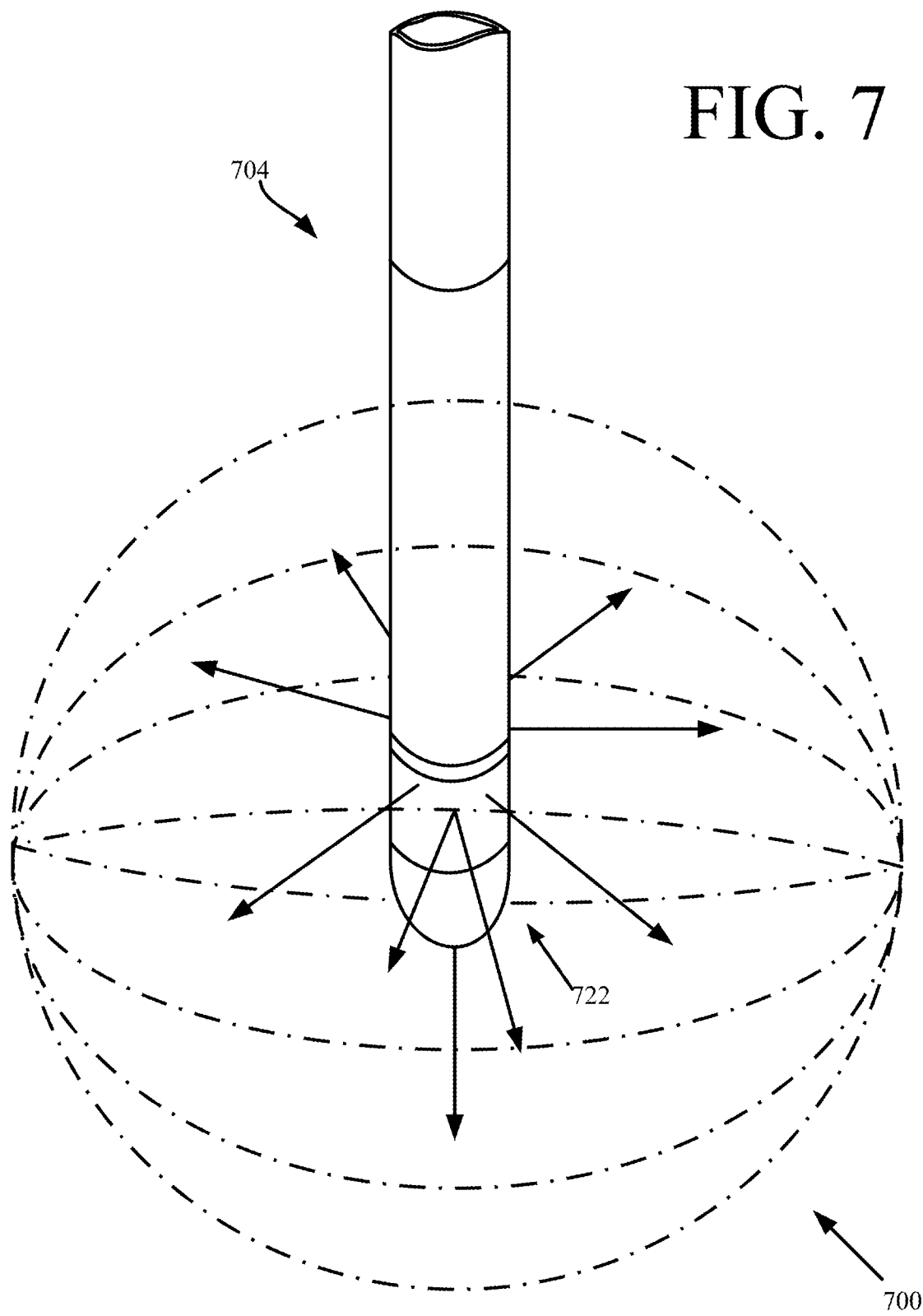
FIG. 7 is an example of a first beam pattern that can be created using the controlled beam X-ray source.
Figure 8:
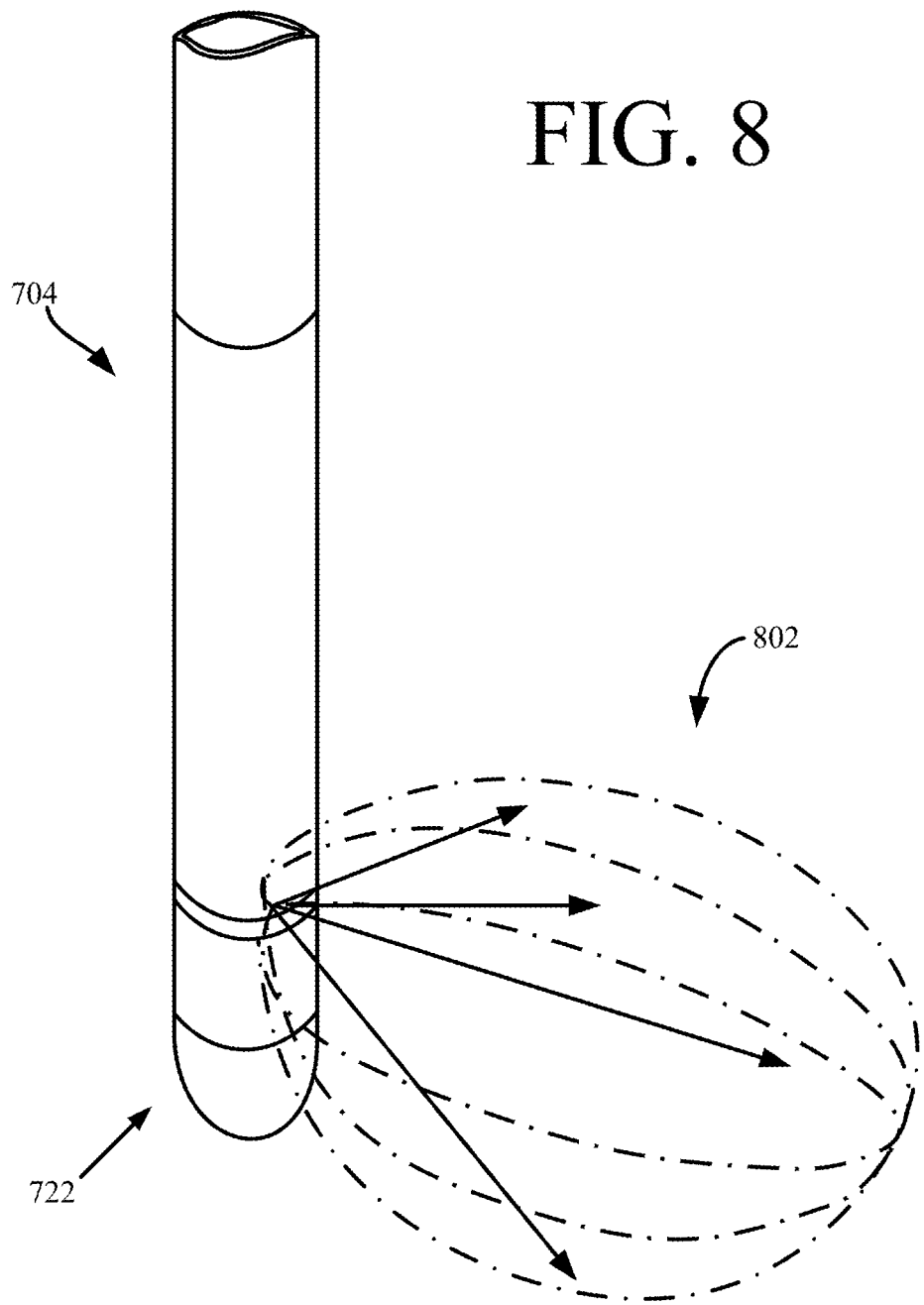
FIG. 8 is an example of a second beam pattern that can be created using the controlled beam X-ray source.

Details of the beam steering and sculpting aspects of the X-ray source in FIG. 6 are beyond the scope of this disclosure. However, it is noted that the direction and shape of the X-ray beam produced by X-ray source 600 can be sculpted or varied by using electromagnetic steering coils 605. The steering coils 605 are under the control of beam steering coil control 624 provided in the base unit. The steering coils 605 are configured to vary the portion of the X-ray target 618 that is impacted by the electrons comprising the electron beam. This steering process is facilitated by a scepter element 619, which is disposed adjacent to the X-ray target 618. For example, in some scenarios, the X-ray source 600 is dynamically configured or controlled so as to facilitate an isotropic pattern 700 for x-ray photon particles as shown in FIG. 7. In other scenarios, the X-ray source 600 is selectively controlled to instead facilitate a directional X-ray beam 802 as shown in FIG. 8. For example, a beam controlled radiation pattern can be facilitated with an X-ray generating system as disclosed in U.S. patent application Ser. No. 15/941,547, which was filed Mar. 30, 2018 and is entitled "Three-Dimensional Beam Forming X-ray Source" (issued as U.S. Pat. No. 10,607,802). The entirety of this patent application is incorporated herein by reference.

The X-ray target 618 is comprised of a disk-shaped element which is disposed transverse to the direction of electron beam travel. For example, the disk-shaped element is disposed in a plane which is approximately orthogonal to the direction of electron beam travel. In some scenarios, the X-ray target 618 encloses an end portion of the drift tube distal from the EBG 602 to facilitate maintenance of the vacuum pressure within the drift tube. The X-ray target 618 can be almost any material. However, the X-ray target 618 is advantageously comprised of a material such as molybdenum, gold, or tungsten which has a high atomic number so as to facilitate the production of X-rays at relatively high efficiency when bombarded with electrons. The generation of X-rays at X-ray target 618 can generate substantial amounts of heat. So a flow of coolant provided by the water cooling system 406 is provided to the treatment head through coolant conduits 606. The various components comprising the X-ray source 600 (e.g., EBG 602, the drift tube 604, and treatment head 622) are mounted on the robotic arm 304 as shown in FIGS. 3 and 4.

Figure 9:
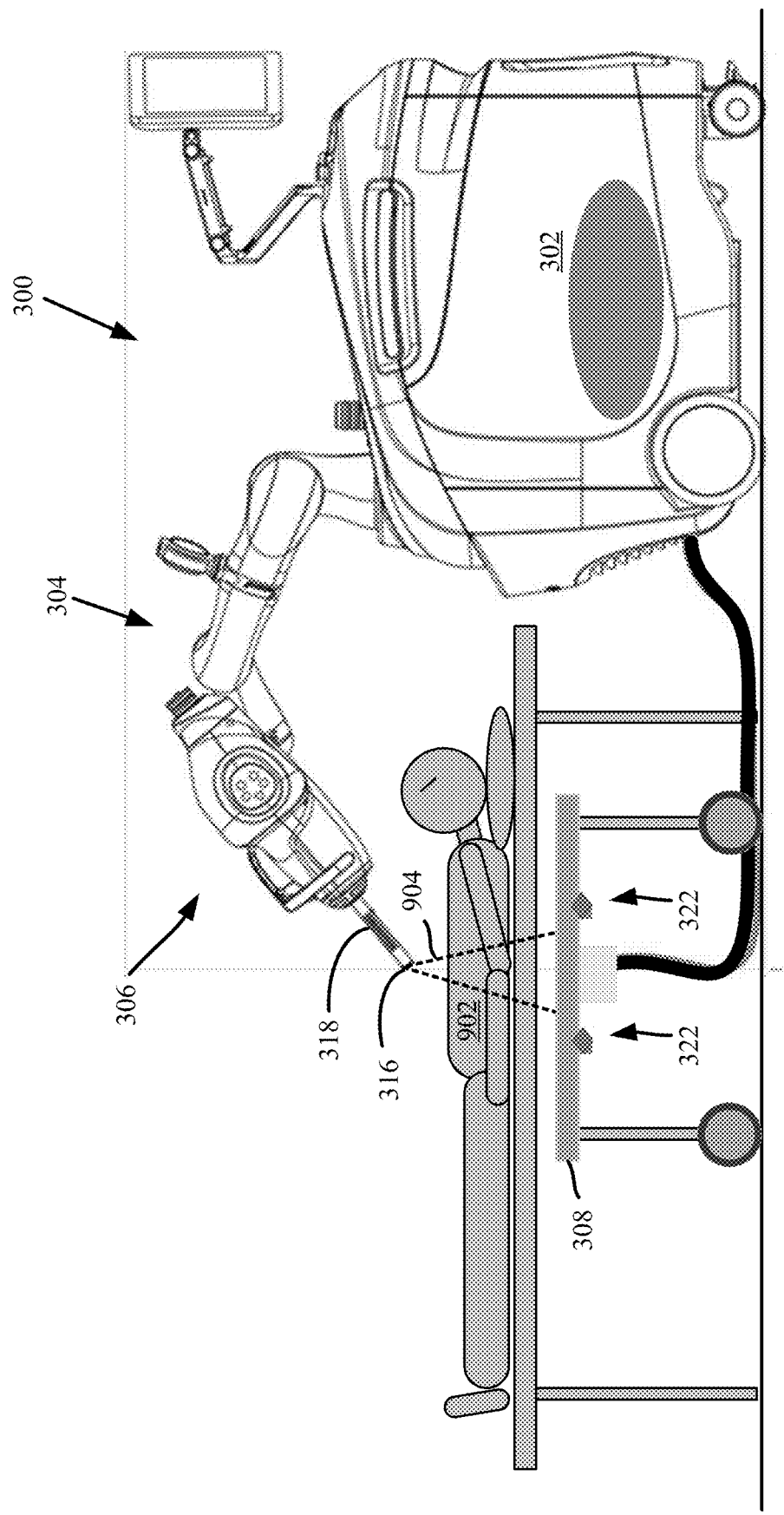
FIG. 9-12 are a series of drawings that are useful for understanding a process whereby tomosynthesis is performed using a robotic X-ray system.
Figure 10:
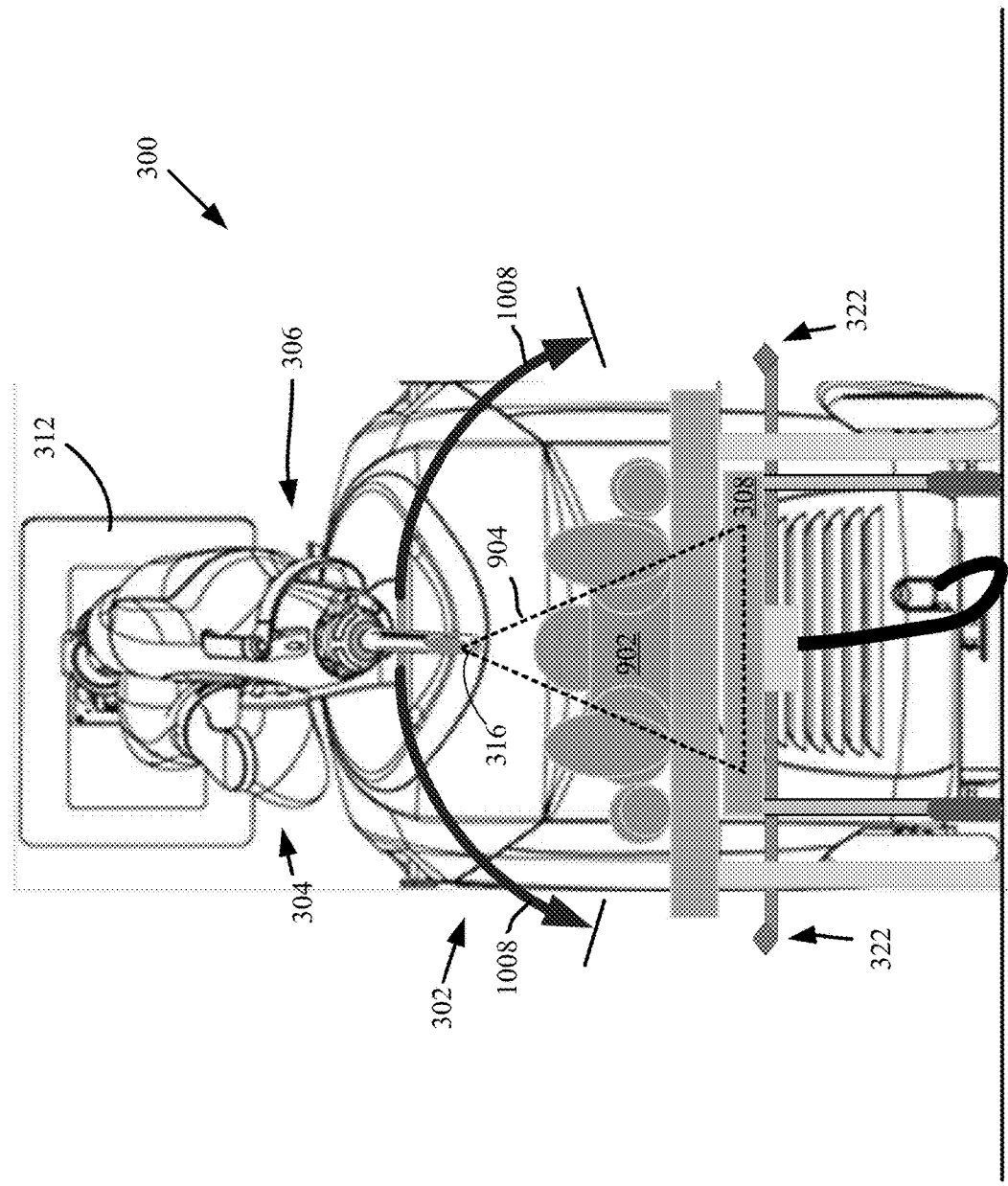
Figure 11:
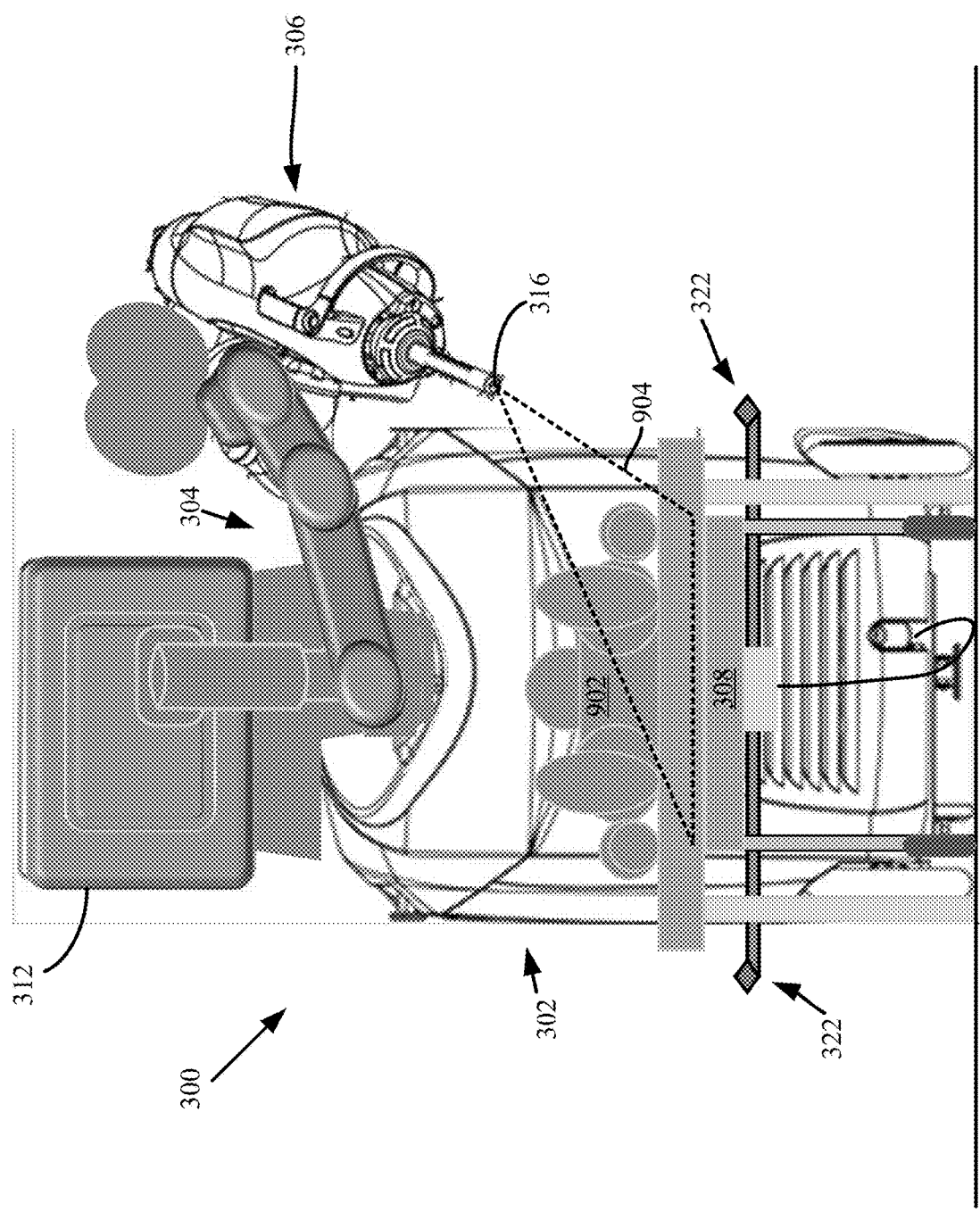
Figure 12:
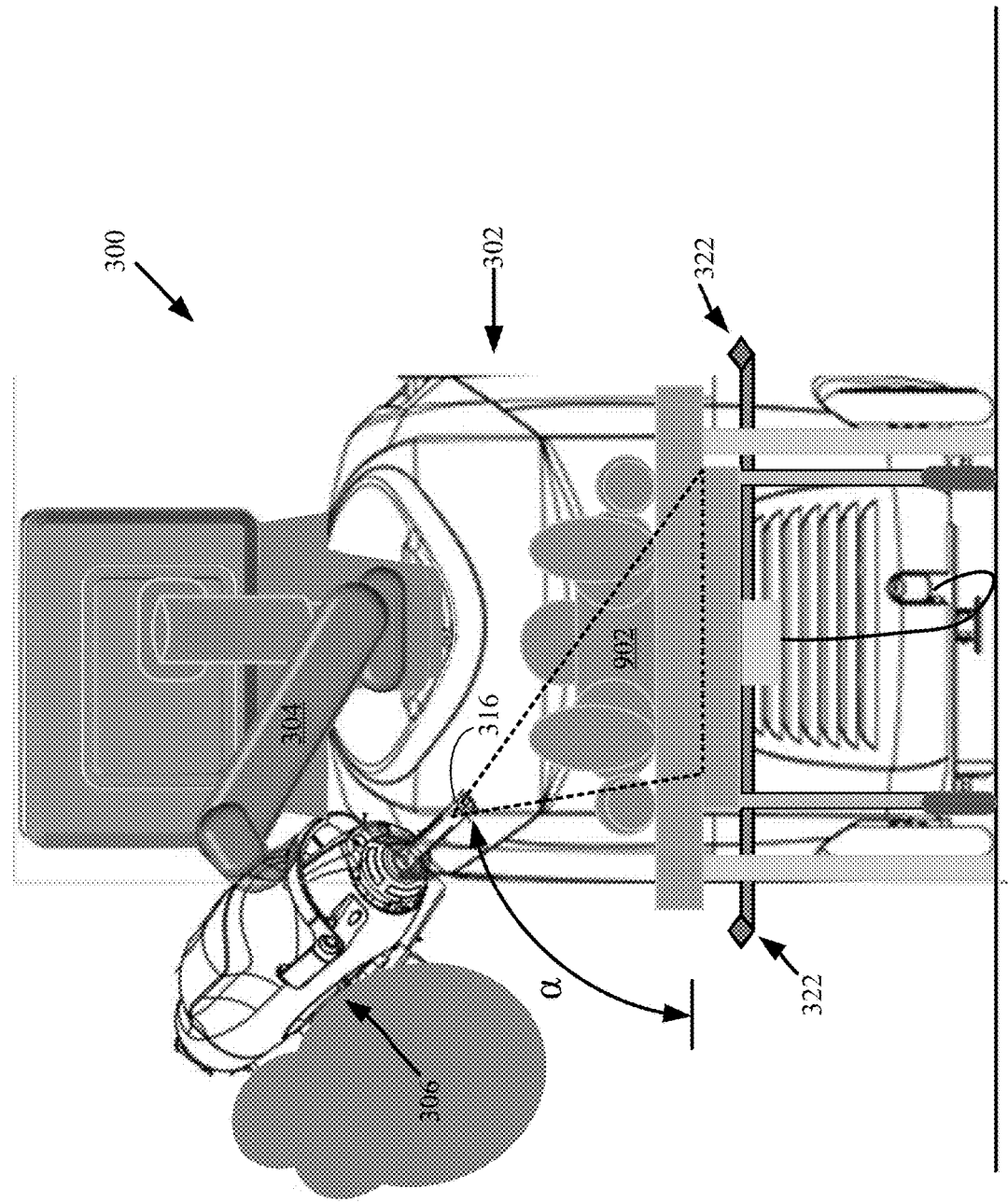

As hereinafter described in greater detail, the X-ray system in FIGS. 3-8 comprises a multifunctional X-ray system which can be adapted or configured for a plurality of different tasks in a medical facility. One such task involves medical imaging, and more particularly DT. Referring now to FIGS. 9-12, the robotic arm 304 precisely controls a position of the X-ray treatment head 316 which serves as an X-ray radiation source. The X-ray treatment head 316 is shown in FIG. 9 as being positioned relative to a subject patient 902 such that a beam 904 of X-ray radiation can be projected through a portion of the patient which is to be imaged. The X-ray detector panel 308 is disposed on a side of the patient opposing the X-ray treatment head such that it is positioned to capture 2D X-ray projection images of the subject patient 902 when the patient is exposed to X-rays produced by treatment head 316.

The 2D X-ray projection images are captured or obtained with the X-ray treatment head 316 located at a plurality of different locations relative to the patient. This concept is illustrated in reference to FIGS. 10-12 which show that the X-ray treatment 316 head is moved by the robotic arm 304 along a predetermined path 1008 in a peripheral space around the patient. The X-ray treatment head 316 is moved along the predetermined path 1008 by selectively controlling (e.g., with system controller 426) a plurality of joint positions associated with a plurality robot arm joints 320. As shown in FIG. 13, the predetermined path 1008 can in some scenarios define an arc which has a central angle β of between 15° and 40°.

In the system described herein, the X-ray beam 904 is shaped or sculpted to primarily direct X-ray radiation toward the X-ray detector panel 308. For example, the beam is controlled in a manner similar to that shown in FIG. 8 to create a cone geometry in which X-ray radiation is primarily directed toward the patient and the X-ray detector panel 308. Further, a cap is disposed on the treatment head 316 when the X-ray system 300 is used for DT operations to facilitate beam shaping and beam hardening. The cap 1410, which is illustrated in FIGS. 14A and 14B, includes a shielded portion 1414 which extends circumferentially around the treatment head 316 so as to ensure that the transmission of X-ray radiation does not occur in undesired directions. An X-ray window 1412 allows collimation of X-ray radiation so that the energy is transmitted in a limited range of angles. This collimation can be configured to facilitate a cone beam geometry in which X-ray radiation is primarily directed to the patient 902 and the X-ray detector panel 308. The X-ray window 1412 is formed of a suitable material such as aluminum so as to facilitate beam filtering and hardening. The cap 1410 includes a registration notch or groove which engages a corresponding structure on the treatment head 316 so that the cap can only reside on the treatment head in one position. Consequently, the X-ray window 1412 is known in advance, and may be registered with a shaped X-ray beam that is produced at the treatment head 316.

For purposes of carrying out DT operations as described herein, the X-ray system 300 is selectively controlled to facilitate an X-ray beam having a suitable intensity. This can involve selectively applying an appropriate accelerating voltage within the X-ray source for purposes of forming the X-ray beam. For example, the system controller 426 applies an energy level of 120 kV for this purpose, which is common for use in DT. The system controller 426 controls the energy associated with the electron beam by selectively varying the output voltage of the H.V. power supply 428.

A laser FOV projector 404 is disposed on the cap 1410. The laser FOV projector 404 is configured to project a pattern of visible laser light 1408 on the patient 902. When projected on the patient, the locations of this pattern of laser light 1408 will correspond to locations which will be exposed to an X-ray beam that is produced by the X-ray system during DT operations. Accordingly, a technician can visibly verify that certain desired portions of the patient anatomy will be illuminated with X-ray radiation during the DT procedure.

The robotic arm 304 controls a position of the X-ray treatment head 316 so that the beam is always oriented in a direction toward the X-ray detector panel 308. In some scenarios, a primary direction of the beam 904 is dynamically controlled concurrent with the movement of the X-ray treatment head 316. For example, the direction of the beam is varied as the X-ray treatment head is moved by the robotic arm along the predetermined path. The direction of the X-ray beam is controlled by selectively varying the position and/or orientation of the treatment head using the robotic arm. The direction of the X-ray beam is also modifiable by using the beam shaping methods described herein with respect to FIGS. 7 and 8.

With the arrangement as described, the 2D projection images are captured by the X-ray detector panel 308 at different times when the X-ray treatment head 316 is located at a plurality of different locations along the predetermined path 1008. Consequently, the 2D X-ray projection images are captured with the X-ray source disposed at a plurality of different angles α (relative to the patient) as the X-ray radiation source (e.g., the X-ray tube) is moved by the robotic arm 304 over a predetermined path 1008.

Solid-state X-ray imaging arrays are well-known in the art, and therefore will not be described here in detail. However, it should be understood that captured 2D X-ray projection images from the X-ray detector panel 308 are communicated to an on-board processing element (such as system controller 426 of FIG. 4). These communications are facilitated by a wired or a wireless link which communicatively couples the X-ray detector panel 308 to the X-ray system 300. In other scenarios, these projection images are communicated to a separate image processing computer (not shown) and/or a data storage device provided in the X-ray system 300.

Concurrent with obtaining each 2D projection image, the system controller 426 determines a corresponding location of the X-ray radiation source as it is moved along the predetermined path by the robotic arm. The position information may be determined based on information received by the system controller 426 (directly or indirectly) from a plurality of joint position sensors 315 which are associated with the joints 320 comprising the robotic arm 304. The position information may be used by the system controller 426 to determine a specific angle α and an exact location of the X-ray radiation source relative to the X-ray detector panel.

Once all of the 2D projection images have been obtained in this manner, the multiple 2D projection images and the location information is processed in a computer processing element (e.g., system controller 426 of FIG. 4) to perform a DT operation. As part of the DT operation, section or slice images of the subject patient are reconstructed based on the 2D projection images. This reconstruction can take place in a manner that is similar to that which is used in a conventional DT systems. In some scenarios, the image reconstruction is performed using a conventional technique known as FBP. As is known, FBP is a type of inverse Radon Transformation.

In order to facilitate the X-ray imaging described herein, it is advantageous for the X-ray system 300 to be able to determine a location of the X-ray detector panel 308 relative to the source of X-ray radiation (which in this case is the treatment head 316 of FIG. 3). This information can be useful for determining an appropriate path 1008 of the treatment head. The information also facilitates the FBP processing associated with the reconstruction of slice images of the subject. In this regard, fiducial markers 322 are provided to facilitate position sensing of the X-ray detector panel 308. The fiducial markers 322 also facilitate registration of images acquired by the imaging array. The exact type of fiducial markers selected for this purpose will depend on the registration system utilized. However, in some scenarios, the fiducial markers comprise simple optical markers suitable for detection for an imaging device.

The one or more fiducial markers 322 are advantageously fixed to the X-ray detector panel 308 in location(s) that allows them to be imaged by an IP camera/imaging sensor 302. The optically imaged positions of these fiducial markers 322 can facilitate the determination of the appropriate path 1008, and the position of the X-ray detector panel 308 relative to the treatment head 316. The position information is then used to facilitate the image collection process, and the image reconstruction process.

Figure 15:
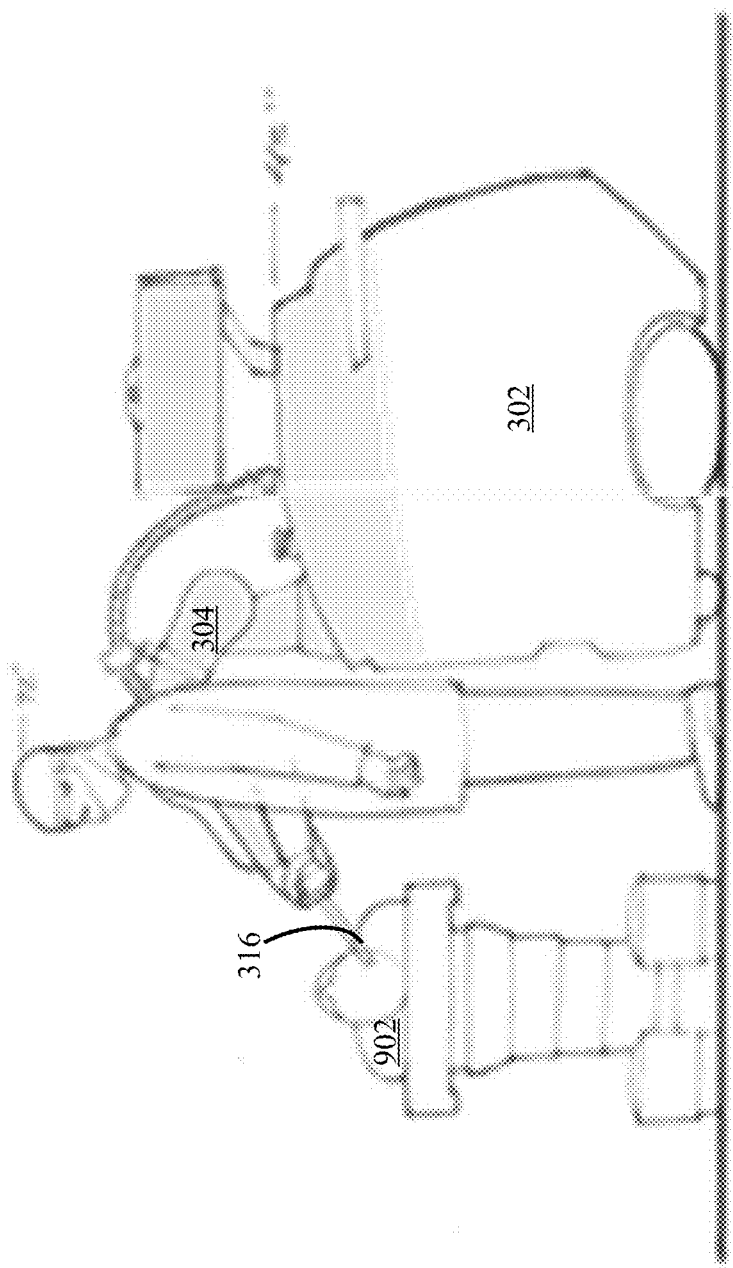
FIG. 15 is a drawing which is useful for understanding how a robotic X-ray system can be used to perform a therapeutic X-ray treatment when it is not being used for tomosynthesis imaging.

The X-ray system 300 is multifunctional insofar as it can be used to perform therapeutic treatment such as IORT, Brachytherapy, and External Beam Radiation Therapy ("EBRT") when it is not being used for tomographic imaging as described herein. For example, consider an IORT scenario in which a surgical procedure has been performed to remove a cancerous tumor from a patient. During the surgical procedure, a practitioner may use the X-ray system to perform certain medical imaging operations as described herein. The surgeon can review the reconstructed images based on the 2D projection images and then initiate an IORT procedure using the X-ray system 300. This IORT procedure is illustrated in FIG. 15 which shows the surgeon can use the robotic arm 304 to reposition the X-ray treatment head 316 with respect to the subject patient 902. In particular, the X-ray source can be repositioned within a tumor bed of the removed cancerous tumor. Thereafter, the X-ray source can be activated while the treatment head 316 is disposed at the treatment location so as to carry out a therapeutic X-ray treatment of the subject patient. In some scenarios, the DT imaging described herein is performed during the procedure, after the tumor has been removed. Such intraoperative imaging is particularly useful to help with RTP because it allows the practitioner to image the tissue to be irradiated immediately after tumor removal, and just before the IORT procedure is initiated.

The usefulness of the DT imaging described herein may be further enhanced by using an image fusion technique. In such a scenario, pre-operative volumetric imaging of a patient undergoing treatment (e.g., tumor removal) can be performed using a conventional imaging method. Examples of suitable volumetric imaging methodologies which can be used for this purpose can include CT and MRI. However, the solution is not limited in this regard and any other suitable volumetric imaging technology can also be used for this purpose, whether now known or known in the future. The acquired pre-operative volumetric imaging can then be stored in a database, such as patient data storage device 440 of FIG. 4. Thereafter, a surgical procedure can be performed on the patient, such as removal of a cancerous tumor. This step can be followed by the intraoperative DT imaging described herein. But rather than simply rely upon the intraoperative DT imaging for purposes of the RTP, an improved or enhanced result can be obtained in a deformable image fusing step. This step can involve fusing the higher quality pre-operative volumetric imaging with the somewhat lower quality intraoperative results obtained using DT.

It will be understood that the internal anatomy of the patient undergoing treatment will necessarily be changed somewhat as a result of the surgical procedure involving cancerous tumor removal. The deformable image fusing step described herein will therefore make use of anatomical landmarks to facilitate image registration, but will advantageously fit the pre-operative volumetric imaging with the intraoperative DT imaging. The resulting fused volumetric image will combine the higher quality pre-operative volumetric imaging, with the lesser quality but more current results obtained using the intraoperative DT imaging. Deep learning or other artificial intelligence techniques can be used to develop and guide this deformable image fusion process. Further, artificial intelligence can be applied to the fusion process to ensure that the deformable image fusion process. Once the deformable fusion process is complete, the RTP process can continue so as to facilitate any IORT treatment. Such fused image can be particularly useful to help with RTP because it allows the practitioner to image the tissue to be irradiated immediately after tumor removal, and just before the IORT procedure is initiated.

Notably, an X-ray beam 904 that is suitable for tomosynthesis as described herein may not be suitable for carrying out a therapeutic treatment, such as IORT. However, a beam shaping capability of the X-ray source can be used to dynamically change the beam shape so that it is suitable for the particular therapeutic treatment. Accordingly, control system 424 of FIG. 4 can be used to selectively control the X-ray source to generate an X-ray beam 904 having a first beam shape for purposes of obtaining the 2D projection images, and subsequently generate an X-ray beam having a different shape for purposes of carrying out the therapeutic X-ray treatment. Similarly, the control system 424 can control an X-ray beam intensity. In this regard it should be understood that the beam intensity used for imaging may be controlled by the control system 424 so that it is different as compared to the beam intensity used for therapeutic purposes (e.g., during IORT procedure). The X-ray system 300 can be controlled to emit low energy X-ray radiation levels for IORT. In some scenarios, the X-ray system 300 reduces X-ray energy to about 50 kV or less for this purpose.

Figure 16:
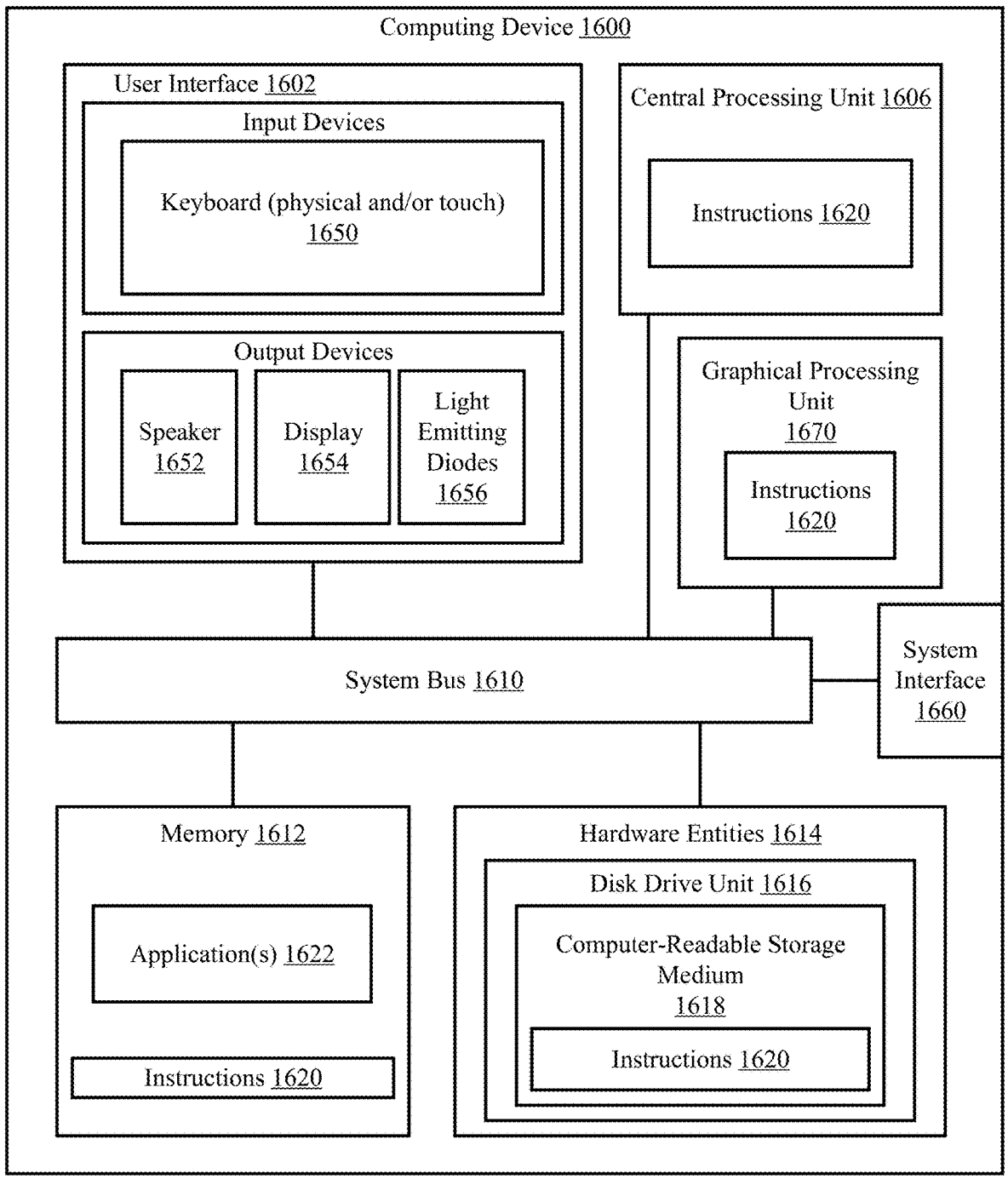
FIG. 16 is an illustration of an illustrative architecture for a computing device.

Referring now to FIG. 16, there is provided an illustration of an illustrative architecture for a computing device 1600. Computing device 102 and/or server 108 of FIG. 1 is(are) the same as or similar to computing device 1600. As such, the discussion of computing device 1600 is sufficient for understanding these components of system 100.

In some scenarios, the present solution is used in a client-server architecture. Accordingly, the computing device architecture shown in FIG. 16 is sufficient for understanding the particulars of client computing devices and servers.

Computing device 1600 may include more or less components than those shown in FIG. 16. However, the components shown are sufficient to disclose an illustrative solution implementing the present solution. The hardware architecture of FIG. 16 represents one implementation of a representative computing device configured to provide real time beam sculpting IORT treatment planning, as described herein. As such, the computing device 1600 of FIG. 16 implements at least a portion of the method(s) described herein. The computing device 1600 can include a battery (not shown) and/or be connected to an external power supply.

Some or all components of the computing device 1600 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 16, the computing device 1600 comprises a user interface 1602, a Central Processing Unit ("CPU") 1606, a Graphical Processing Unit ("GPU") 1670, a system bus 1610, a memory 1612 connected to and accessible by other portions of computing device 1600 through system bus 1610, a system interface 1660, and hardware entities 1614 connected to system bus 1610. The user interface can include input devices and output devices, which facilitate user-software interactions for controlling operations of the computing device 1600. The input devices include, but are not limited, a physical and/or touch keyboard 1650, and/or a physical and/or touch pointing device (not shown in FIG. 16). The input devices can be connected to the computing device 1600 via a wired or wireless connection (e.g., a Bluetooth® connection). The output devices include, but are not limited to, a speaker 1652, a display 1654, and/or light emitting diodes 1656. System interface 1660 is configured to facilitate wired or wireless communications to and from external devices (e.g., network nodes such as access points, etc.).

At least some of the hardware entities 1614 perform actions involving access to and use of memory 1612, which can be a Random Access Memory ("RAM"), a solid-state or a disk driver and/or a Compact Disc Read Only Memory ("CD-ROM"). Hardware entities 1614 can include a disk drive unit 1616 comprising a computer-readable storage medium 1618 on which is stored one or more sets of instructions 1620 (e.g., software code) configured to implement one or more of the methodologies, procedures, or functions described herein. The instructions 1620 can also reside, completely or at least partially, within the memory 1612 and/or within the CPU 1606 during execution thereof by the computing device 1600. The memory 1612 and the CPU 1606 also can constitute machine-readable media. The term "machine-readable media", as used here, refers to a single medium or multiple media (e.g., a centralized or distributed database, and/or associated caches and servers) that store the one or more sets of instructions 1620. The term "machine-readable media", as used here, also refers to any medium that is capable of storing, encoding or carrying a set of instructions 1620 for execution by the computing device

1600 and that cause the computing device 1600 to perform any one or more of the methodologies of the present disclosure.

The GPU 1670 is used for, but not limited to, 2D images rendering, 3D isospheres rendering, augmented reality objects rendering and parallel mathematical processing tasks. The GPU has its own instruction set, as described with the CPU.

Computing device 1600 implements treatment plan creation technology. In this regard, computing device 1600 runs one or more software applications 1622 for facilitating real time beam sculpting IORT treatment planning. Operations of the software applications 1622 will become evident as the discussion progresses.

Figure 17:
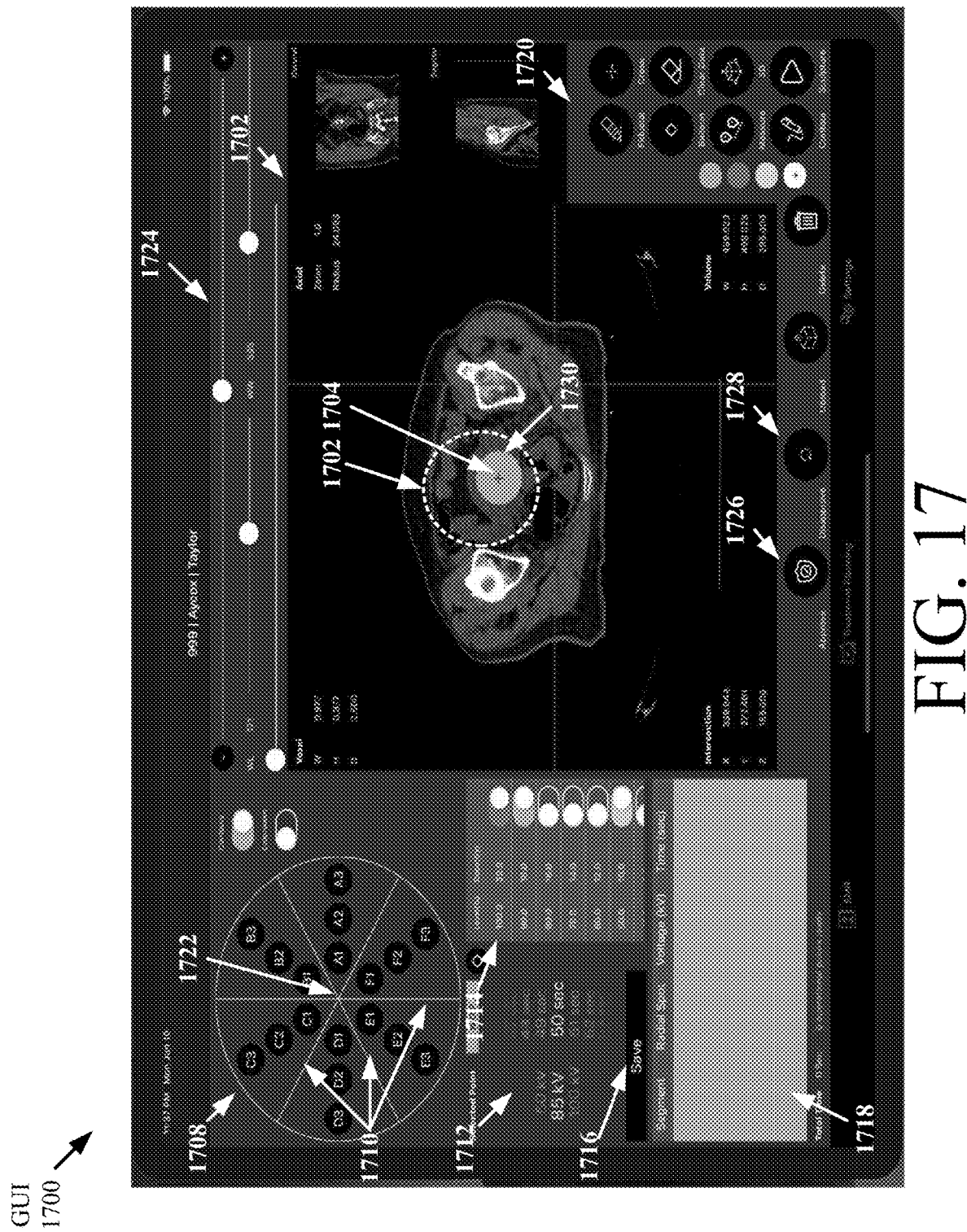
FIGS. 17-24 each provide a screen shot of an illustrative GUI for creating a treatment plan for a patient.

Referring now to FIG. 17, there is provided a screen shot of an illustrative GUI 1700 provided by the software applications 1622. GUI 1700 is designed to facilitate the creation of a treatment plan for a patient who is to have radiation therapy in relation to his/her cancer. In this regard, the GUI comprises a first portion 1702 showing general imaging modality. The general imaging modality includes, but is not limited to, a CT scan, an MRI, a PET, or a Tomosynthesis. The first portion 1702 has three parts: an original planar image set (e.g., an Axial plane) and two reconstructed planar image sets (e.g., Coronal and Sagittal planes). As such, the first portion 1702 of FIG. 4 shows a main planar view (e.g., an Axial plane) and secondary planar views (e.g., Coronal or Sagittal planes) of the medical image modality. Notably, the imaging may be acquired using the treatment system 106 of FIG. 1 following a tumor's removal by using the source inside the treatment head. The location of each one of the fiducial markers contained in multiple locations on the treatment head or on a designated phantom, such as on, but not limited to, the balloon applicator and the cannula, are shown by one or more crosses 1704. These fiducial markers allow the user to know the location and orientation of the treatment head inside the patient. The treatment head is generally circular in form, is shown on the image and resides in the area encompassed by the dotted line 1706. The fiducial markers, the radius of the balloon applicator, and the location of the intersection point between the three planes can be chosen and marked by using the buttons in the control panel as shown in portion 1720.

The treatment head has a plurality of apertures from which a radiation beam can be emitted. A schematic illustration of the treatment head and its apertures is provided in a second portion 1708 of the GUI 1700. As shown in portion 1708, the treatment head comprises a plurality of apertures represented by multiple areas, with a unique mark for each area. For example, as shown in portion 1708, these areas are marked A1-A3, B1-B3, C1-C3, D1-D3, E1-E3 and F1-F3. Adjacent sets of apertures are separated from each other by outwardly protruding plates represented by the lines 1710 crossing the center 1722 in portion 1708. The plates assist with a controlled application of radiation only to select areas within the patient (e.g., patient 902 of FIG. 9). The areas marked A1-A3, B1-B3, C1-C3, D1-D3, E1-E3 and F1-F3 in portion 1708 are selectable by a user of the GUI 1700. The GUI 1700 also comprises widgets 1712 which allow the user to select a strength of radiation to be applied to the patient, and a duration at which radiation should be applied to the patient. The user can choose the voltage and time for each treatment item in portion 1708 by using the selectors as shown in portion 1712. When the user is pressing the button 1716, a treatment item is added to the treatment plan and displayed in portion 1718 of GUI 1700. Each treatment plan item is adjustable by using a control panel in portion 1724.

Figure 18:
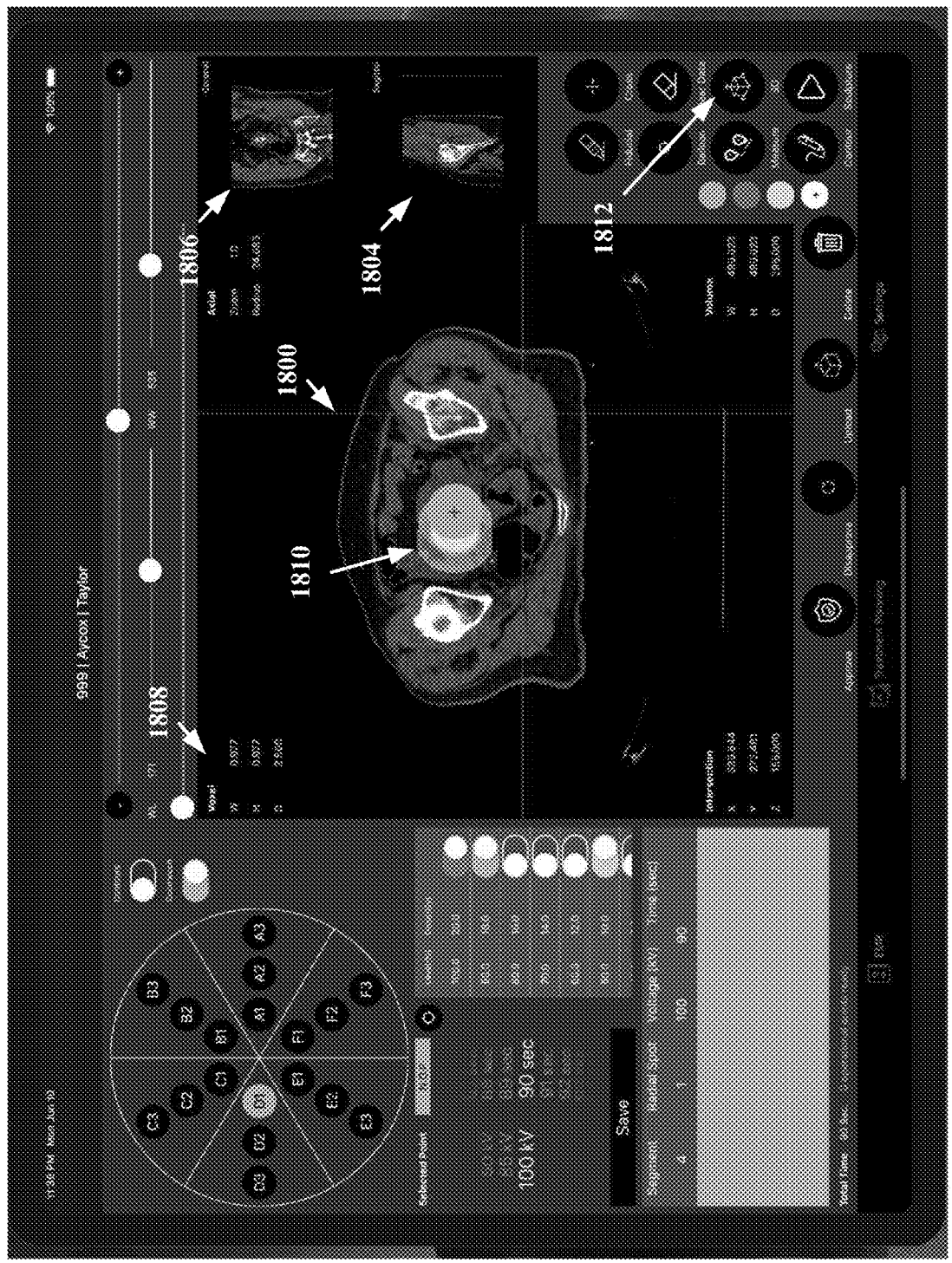
Figure 19:
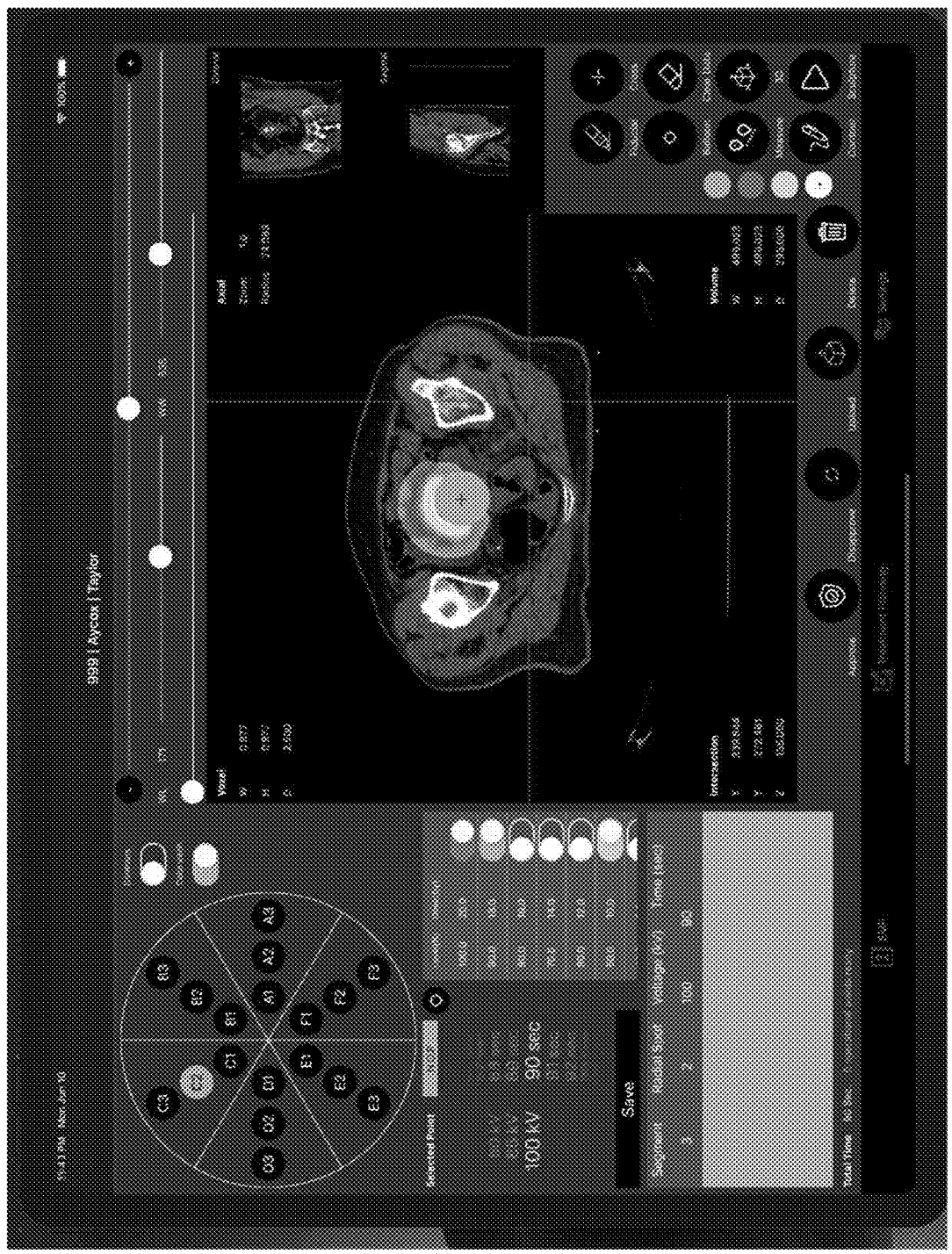
Figure 20:
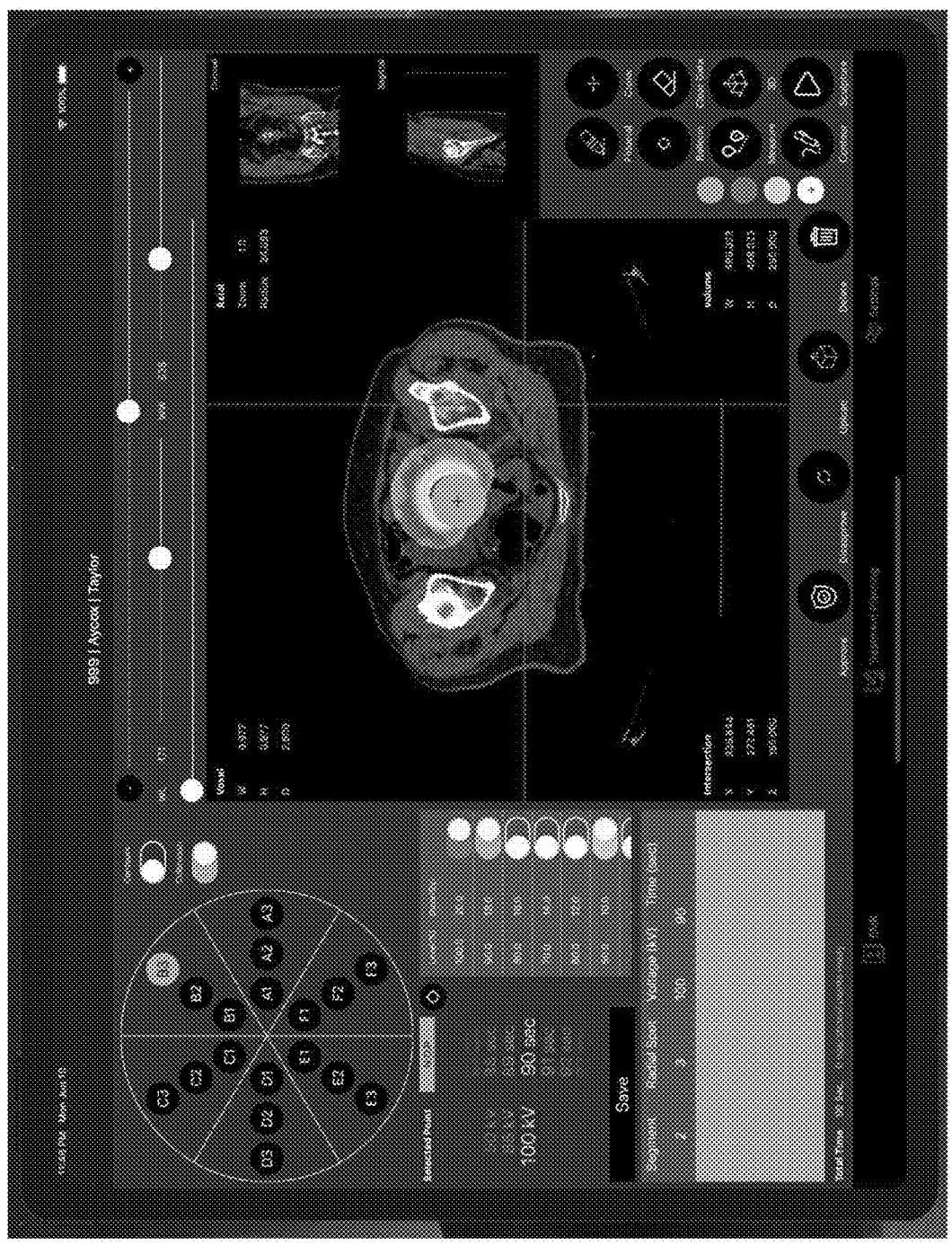

The user can adjust the correlation between the dose level and the isodose percentage by using a correlator as shown in portion 1724. Once the treatment plan has been created, the treatment plan can be approved or disapproved by using the buttons 1726, 1728 in the control panel. Once the treatment plan has been approved, the treatment system 106 of FIG. 1 is programmed to apply radiation to the patient in accordance with the same. This programming can be achieved by the server 108 of FIG. 1. Radiation patterns for various treatment plans implemented by the treatment system 106 of FIG. 1 are shown in FIGS. 18-20.

Prior to programing the treatment system 106 with a treatment plan, the user of computing device 102 can use a tool of the software application 1622 to verify the treatment plans expected effectiveness. This tool comprises a dynamic virtual measurement component presented in the GUI 1700 so as to be superimposed on top of the medical image modality scan shown in the original planar image area 1702. Illustrations showing the dynamic virtual measurement component superimposed on top of the medical image modality scan are provided in FIGS. 21-41.

Figure 21:
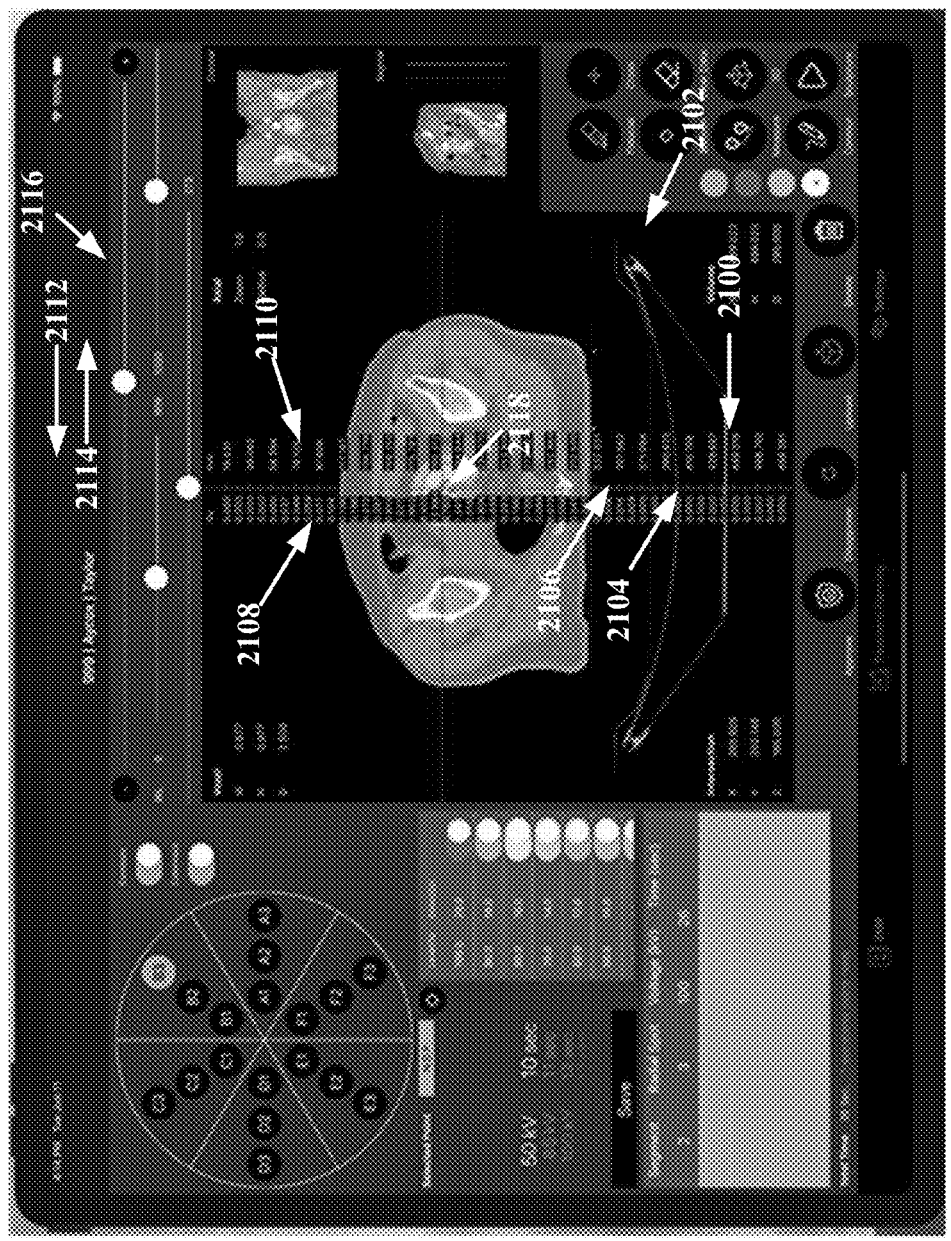
Figure 22:
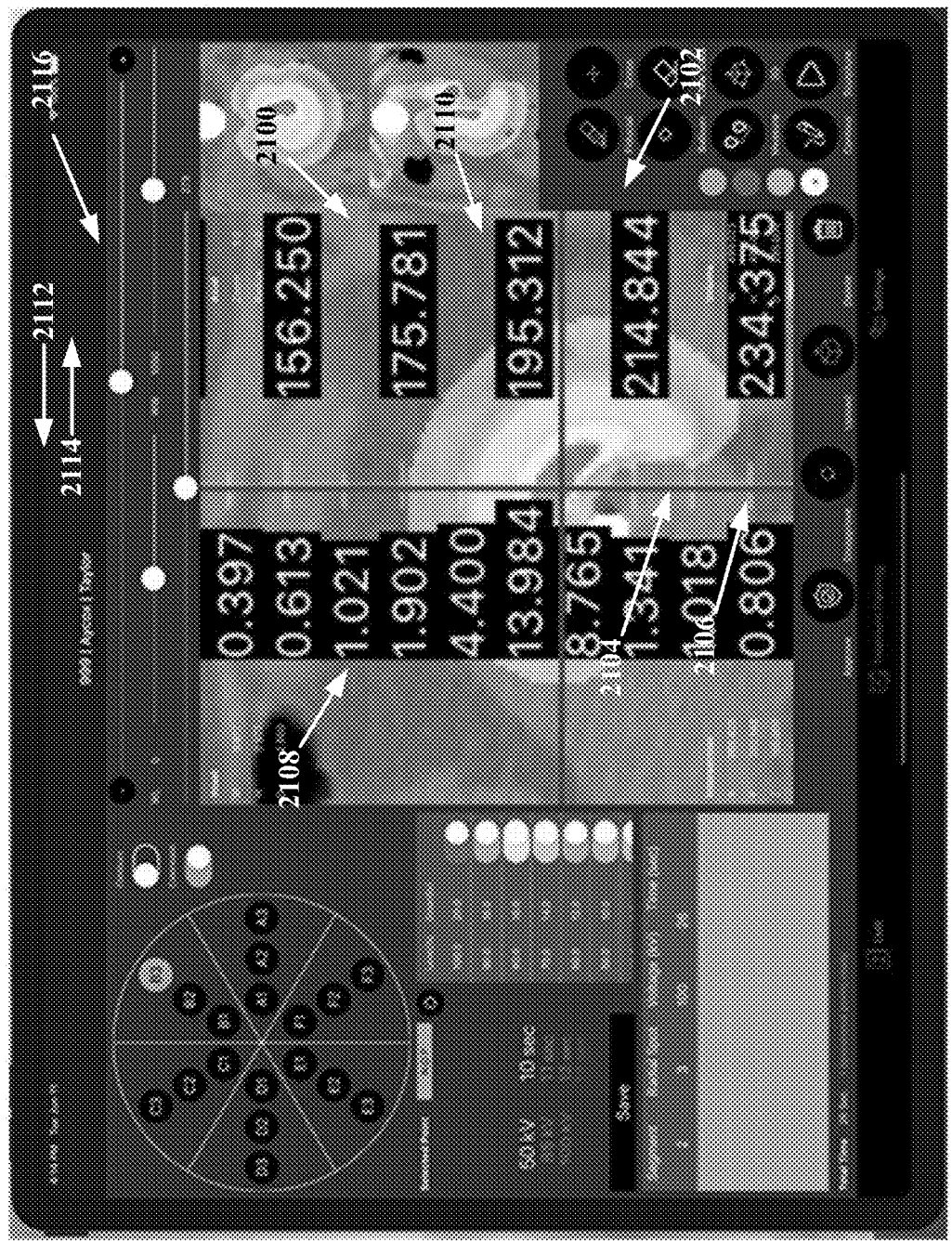
Figure 23:
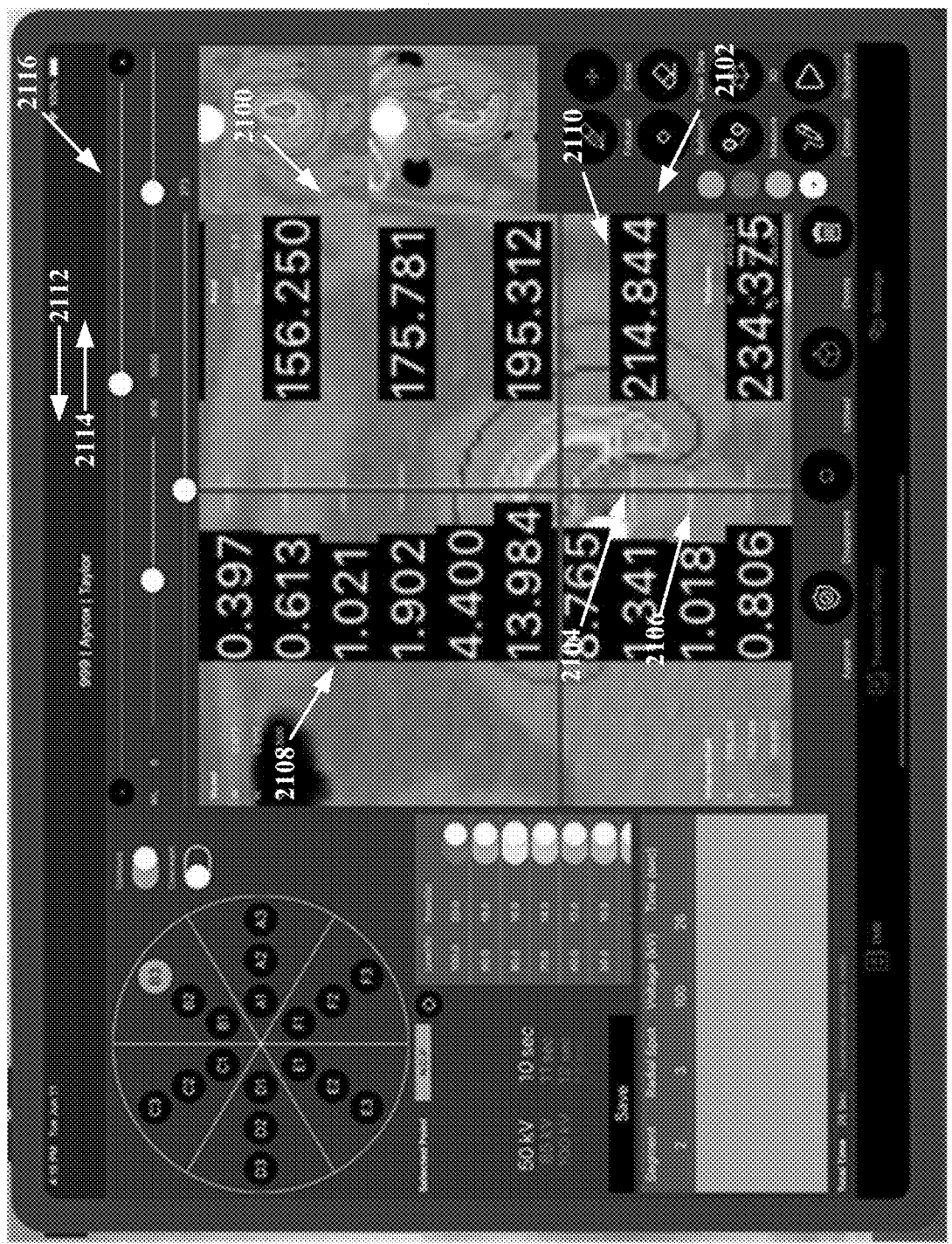
Figure 24:
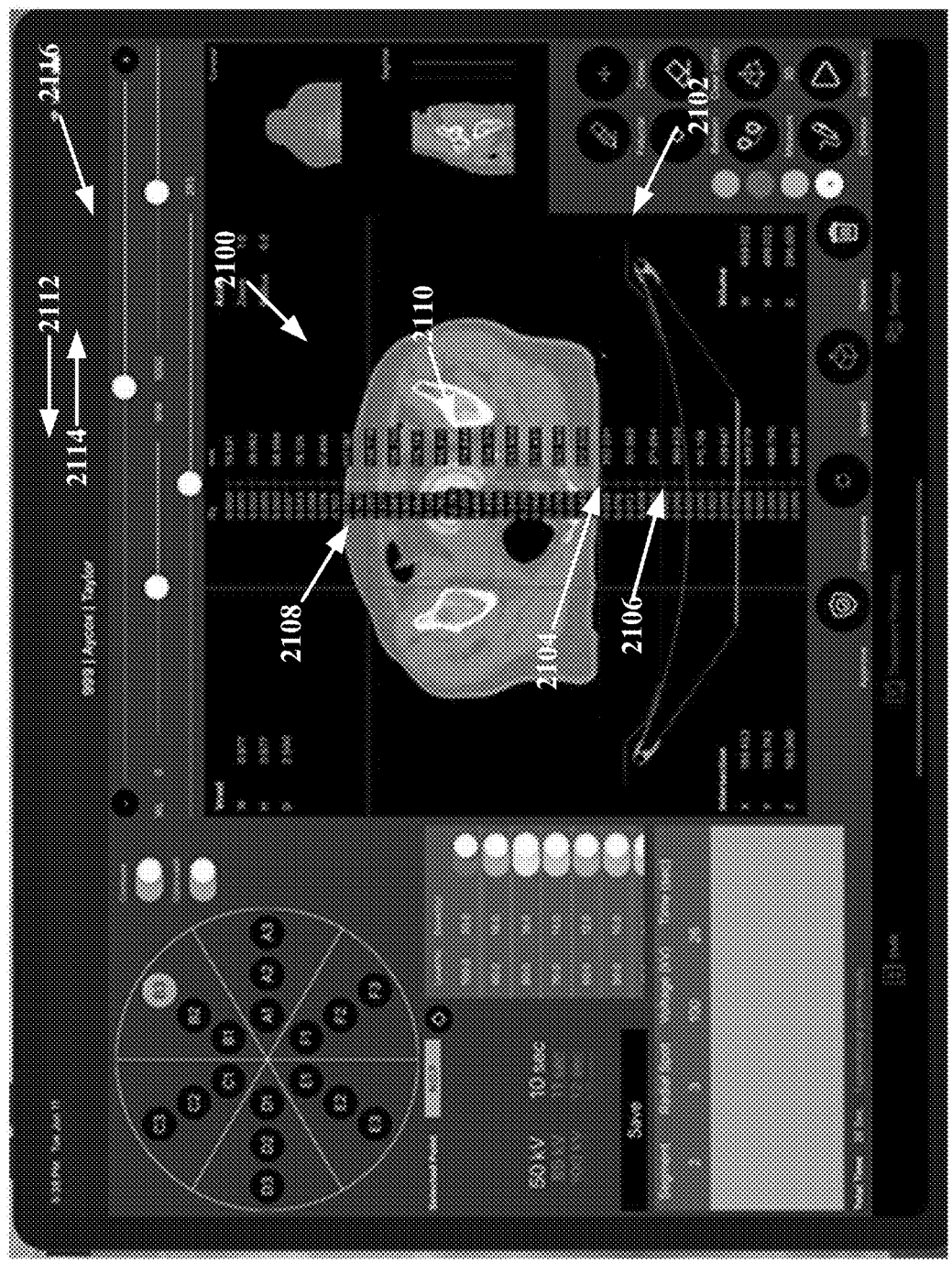

Referring now to FIG. 21, there is provided an illustration of a virtual measurement component 2100 superimposed on top of the medical modality scan image 2102. The virtual measurement component 2100 comprises a center line 2104 with equally spaced markers distributed along its elongate length. The markers include relatively small linear markings (e.g., lines) 2106 that are perpendicular to the center line 2104. Numbers are provided to the left and right of each small line 2106. The numbers 2108 to the left of the center line 2104 represent radiation dose amounts in Gray (Gy) at points of intersection between the center line 2104 and the small linear markings 2106. The numbers 2110 to the right of the center line 2104 represent distance values measured in millimeters (mm) from the center of the target (denoted with a cross in the center of the balloon) 1704 of FIG. 17 to the point of intersection between the center line 2104 and the small linear markings 2106. Accordingly, the virtual measurement component has a dual purpose of allowing a user to measure distances and allowing a user to measure radiation dose amounts. The distance measurements and radiation dose measurements can be performed simultaneously or concurrently. The values of numbers 2108 and 2110 dynamically change as the virtual measurement component is moved horizontally in directions 2112, 2114 via widget 2116. The virtual measurement component 2100 can be in the form of vertical center line 2104, horizontal center line or the combination of both. Widget 2116 is shown as a sliding scale. The present solution is not limited in this regard. Other types of widgets can be used to move the virtual measurement component 2100 horizontally within the GUI. Zoomed-in views of the virtual measurement component 2100 are provided in FIGS. 22-24.

As shown in FIGS. 21-24, numbers 2108 can have different values based on (1) the location of the vertical and/or horizontal center line 2104 relative to the fiducial market dot 2118 and (2) the parameters of the treatment plan. The values of the numbers 2108 can be determined using a Look-Up Table ("LUT") stored locally on or remotely from the computing device 102 of FIG. 1 and/or using at least one pre-defined mathematical algorithm.

Figure 25:
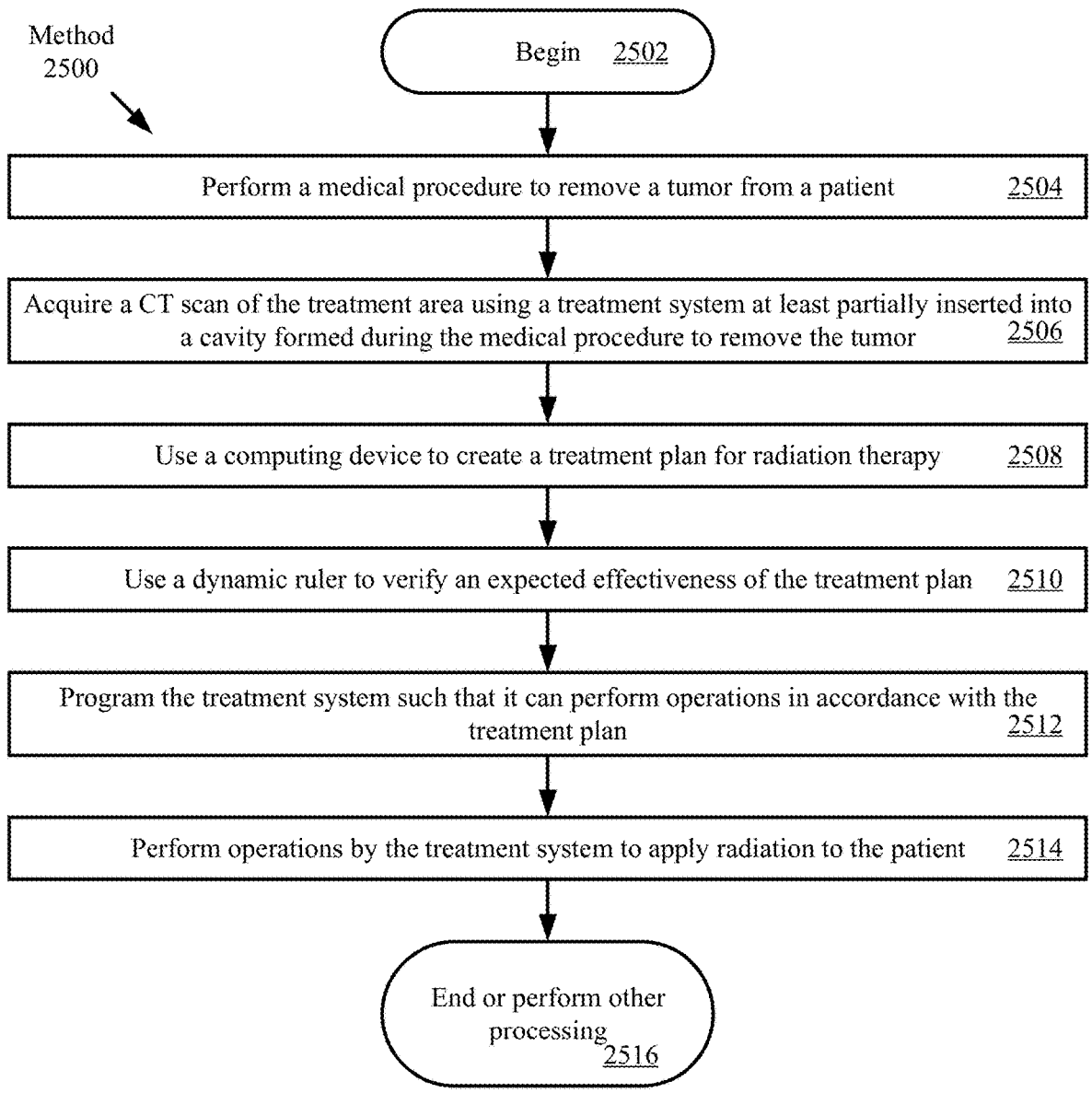
FIG. 25 provides a flow diagram of an illustrative method for creating a treatment plan for a patient.

Referring now to FIG. 25, there is provided a flow diagram of an illustrative method 2500 for treating a patient with cancer. Method 2500 begins with 2502 and continues with 2504 where a medical procedure is performed to remove a tumor from a patient.

Next in 2506, a medical image modality scan of the treatment area is acquired using a treatment system (e.g., treatment system 106 of FIG. 1). Subsequently, a computing device (e.g., computing device 102 of FIG. 1) and a server (e.g., server 108 of FIG. 2) are used in 2508 to create a treatment plan for radiation therapy. The treatment plan is created using a software application installed on the computing device and/or accessible via a software application (e.g., software application 1622 of FIG. 16) installed on the server (e.g., server 108 of FIG. 1). The software application provides a GUI (e.g., GUI 1700 of FIG. 17) within which the medical image modality scan is displayed along with a plurality of widgets for defining parameters of the treatment plan. A dynamic virtual measurement component (e.g., virtual measurement component 2100 of FIGS. 21-24) is used in 2510 to verify an expected effectiveness of the treatment plan. If the results of the verification are insufficient, then the user can go back to 2508 and modify the treatment plan. If such verification is made, then the treatment system is programmed in 2512 such that it can perform operations in accordance with the treatment plan. This programming can be achieved by: communicating a treatment plan from the computing device to the server; and performing operations by the server to set operational parameters and other values in accordance with the treatment plan on the treatment system.

Thereafter, radiation is applied to the patient (e.g., patient 902 of FIG. 9) as shown by 2514. Subsequently, 2516 is performed where method 2500 ends or other processing is performed (e.g., return to 2502).

The present solution also concerns a system for sculpted beam treatment planning applications. Such a system is the same as or similar to system 100 of FIG. 1. This system is also referred to herein as "a Treatment Planning System ("TPS")". The TPS offers a dedicated method and system to create a real-time treatment plan for the robotic sculpted beam IORT system 300 of FIGS. 3-15. The TPS comprises a software application that is run on a mobile computing device (e.g., computing device 102 of FIG. 1) or other computing device.

In some scenarios, the TPS 100 comprises the mobile computing device 102 which acts as a main user interface, the server 108 which implements a parallel computing platform (such as a CUDA®, or other parallel processing platforms), and a treatment system 106. Treatment system 106 includes, but is not limited to, the robotic sculpted beam IORT system 300 of FIGS. 3-15. All of these listed devices operate on a dedicated secured closed-loop Gigabit or faster network. The TPS 100 is capable of creating multiple real time sculpted beam treatment plans for multiple robotic sculpted beam IORT systems in a facility. Furthermore, the TPS 100 allows multiple users to work on the same treatment plan simultaneously.

Figure 26A:
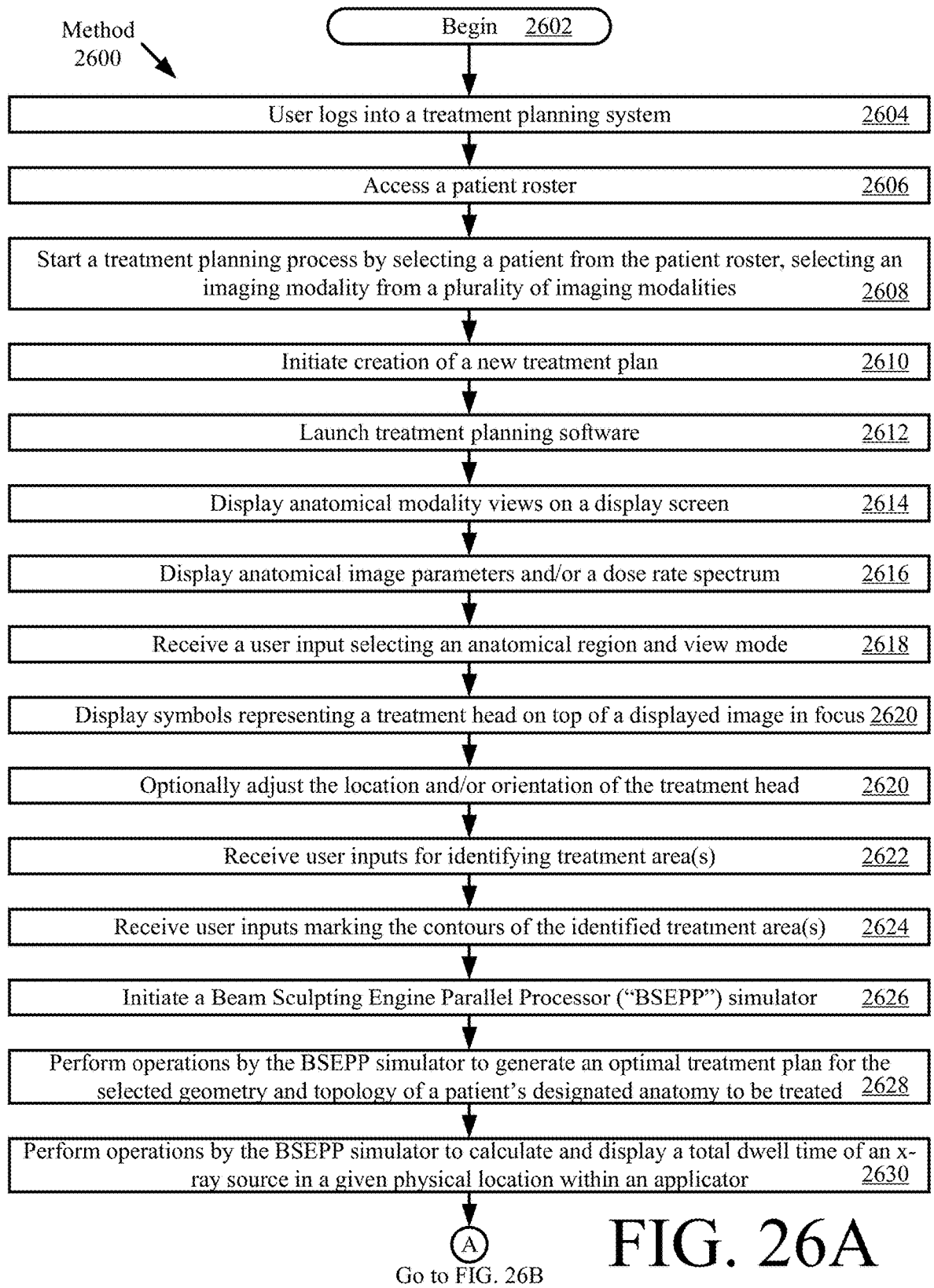
FIGS. 26A-26B (collectively referred to herein as FIG. 26) provide a flow diagram of another illustrative method for creating a treatment plan for a patient.

Referring now to FIG. 26, there is provided a flow diagram of an illustrative method 2600 for operating a TPS (e.g., system 100 of FIG. 1). Method 2600 begins with 2602 and continues with 2604 where a user logs into the TPS using a computing device (e.g., computing device 102 of FIG. 1). Techniques for logging into systems are well known in the art, and therefore will not be described herein. Any known or to be known login technique can be used herein. In some scenarios, a user identifier and/or password are used for login purposes. Additionally or alternatively, biometrics are used for login purposes (e.g., Touch ID and/or Face ID).

Once the user is successfully logged into the TPS, the user accesses an electronic patient roster as shown by 2606. Electronic patient rosters are well known in the art, and therefore will not be described herein. Any known or to be known electronic patient roster can be used herein without limitation. The electronic patient roster may be stored in a data store which is remote from the user's computing device. In this case, a server (e.g., server 108 of FIG. 1) may facilitate access to the electronic patient roster. A screen shot of an illustrative GUI for accessing a patient roster 2700 is provided in FIG. 27.

Figure 27:
FIG. 27 provides a screen shot of an illustrative GUI for accessing a patient roster and selecting a patient from the patient roster.
Figure 28:
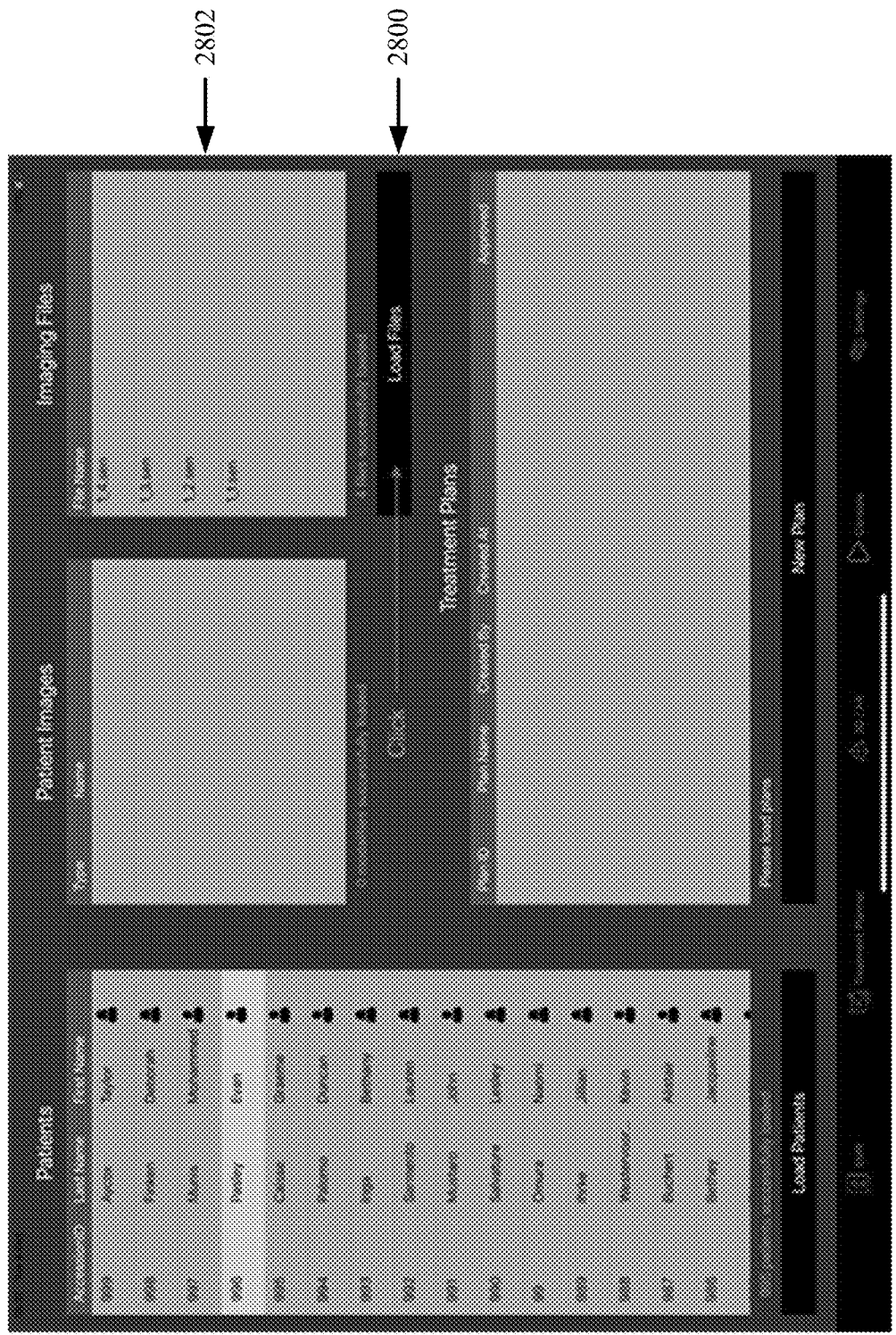
FIG. 28 provides a screen shot of an illustrative GUI for loading image filed from a remote computing device to a local system.
Figure 29:
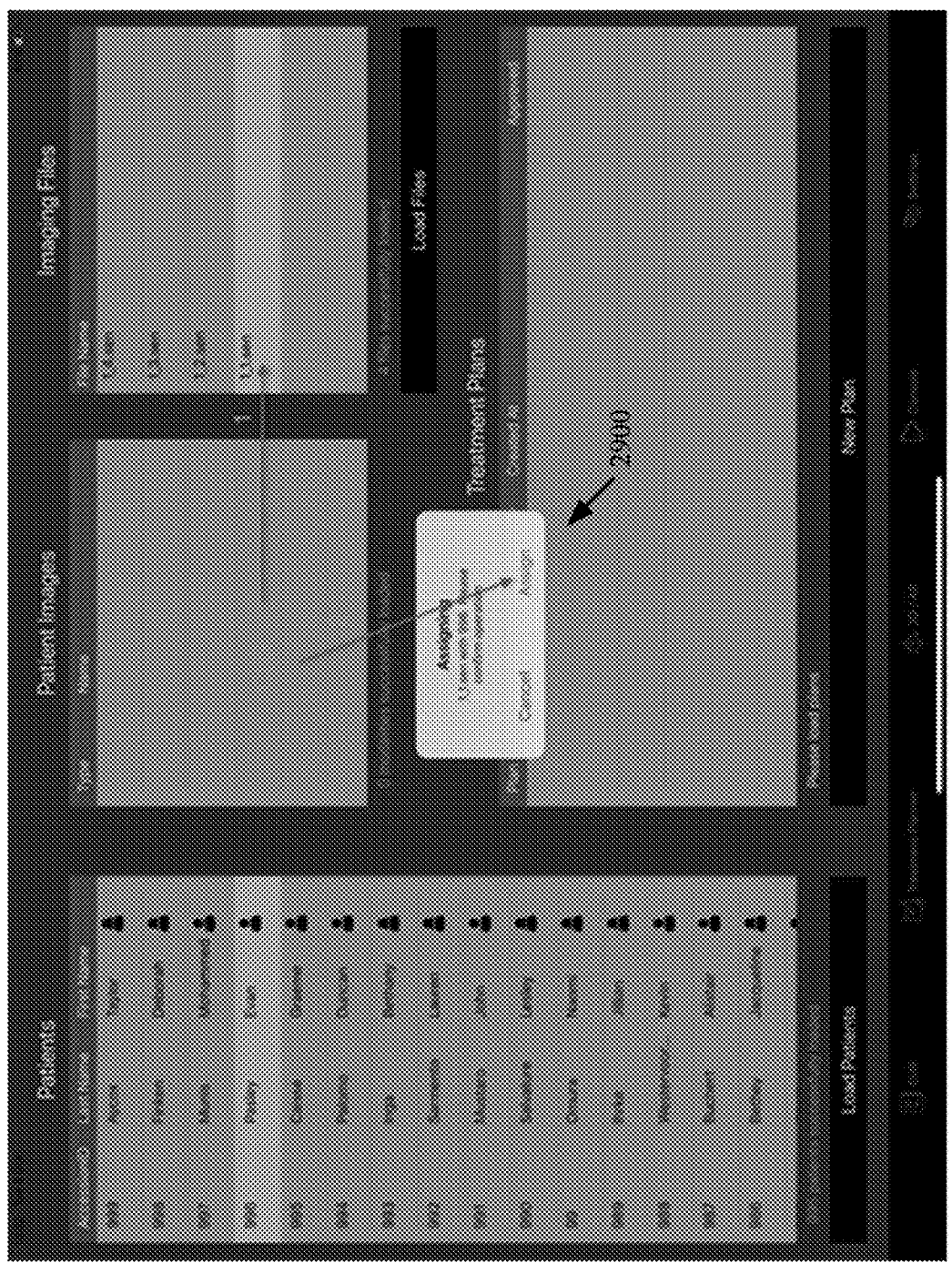
FIG. 29 provides a screen shot of an illustrative GUI for assigning image file(s) to a patient.
Figure 30:
FIG. 30 provides a screen shot of an illustrative GUI for selecting the image file for the treatment planning procedure.

The user starts a treatment planning process in 2608 by selecting a patient's name from the electronic patient roster, and selecting an imaging modality from a plurality of imaging modalities (e.g., a DT scan, a CT scan, an MRI, or a PET scan). FIG. 27 also shows an illustrative way of selecting a patient (e.g., Evan Pasley) from the patient roster 2700. For example, the patient is selected by moving a mouse over the name and depressing a mouse button. Alternatively, a gesture can be made to select the patient if the display is a touch screen display. Once the patient has been selected, then a load files virtual button 2800 is depressed (e.g., using the mouse or via a gesture), as shown in FIG. 28. Depression of button 2800 causes imaging files to be loaded from a remote sever (e.g., server 108 of FIG. 1 or a PACS in a hospital) to the TPS. FIG. 28 also shows an illustrative list 2800 of loaded imaging files (e.g., 1_4.sen, 1_3.sen, 1.2_sen, 1_1.sen). Next, the user assigns an imaging modality to the selected patient. As shown in FIG. 29, this assignment is achieved by: selecting one of the loaded imaging files (e.g., 1_1.sen) (e.g., via a mouse click or via a gesture); and depressing an assign virtual button 2900 to assign the selected imaging file to a treatment plan. Thereafter, the user selects an associated imaging modality. As shown in FIG. 30, this selection is made by selecting one or more imaging subsets 3000 contained in the previously selected imaging file.

Figure 31:
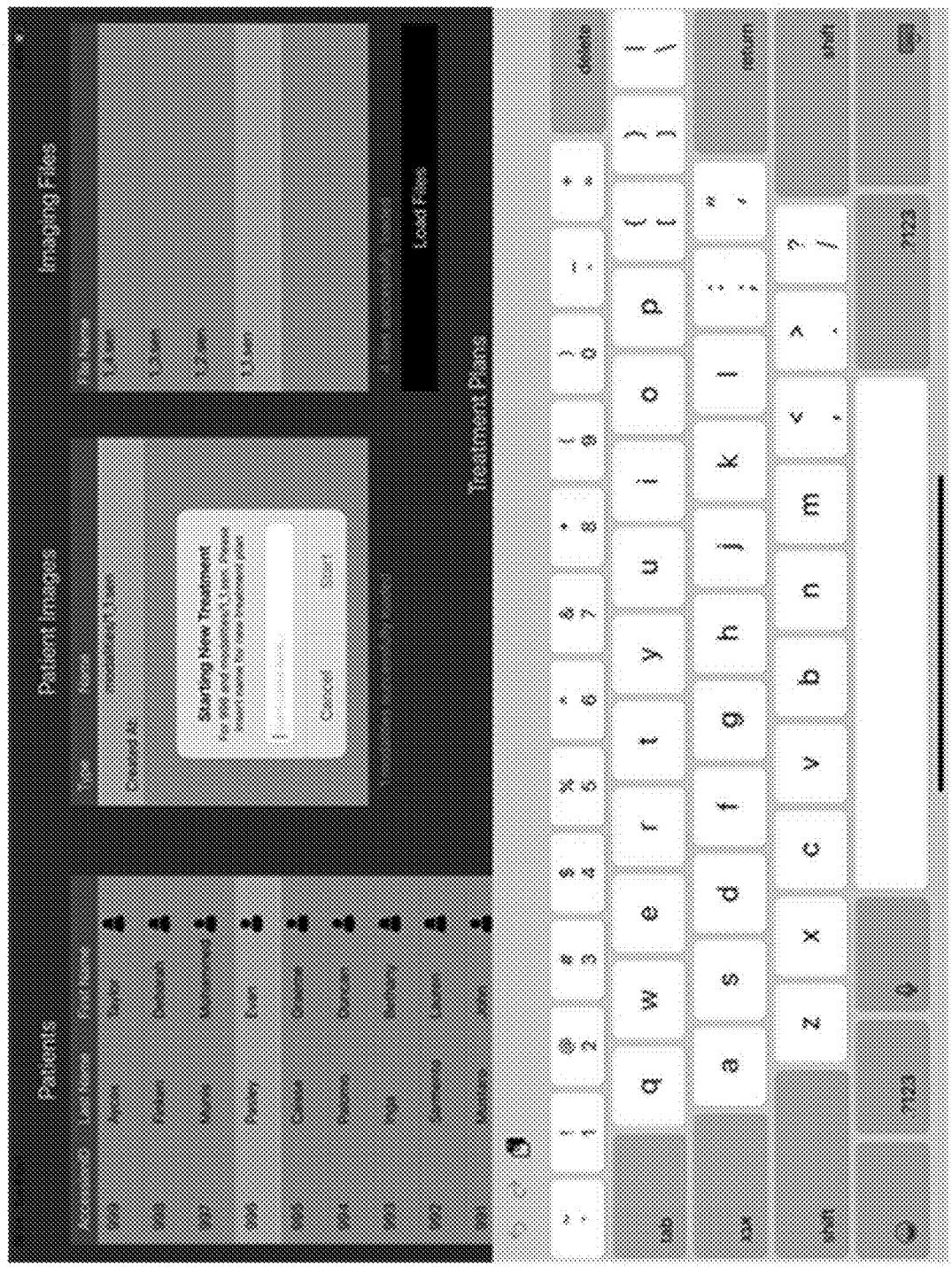
FIG. 31 provides a screen shot of an illustrative GUI for inputting a name for a treatment plan.
Figure 32:
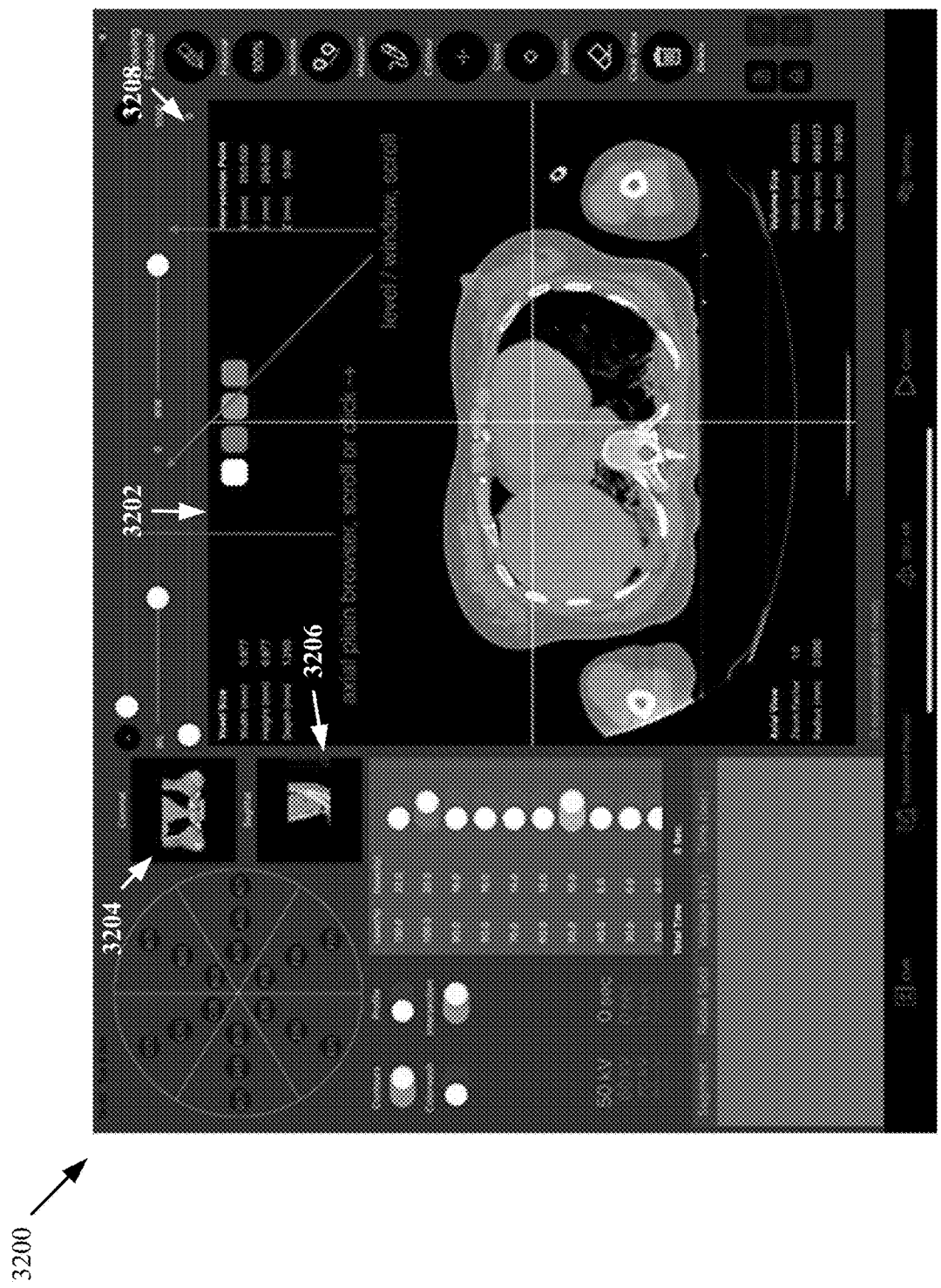
FIG. 32 provides a screen shot of an illustrative GUI displaying images in various anatomical imaging modality views.
Figure 33:
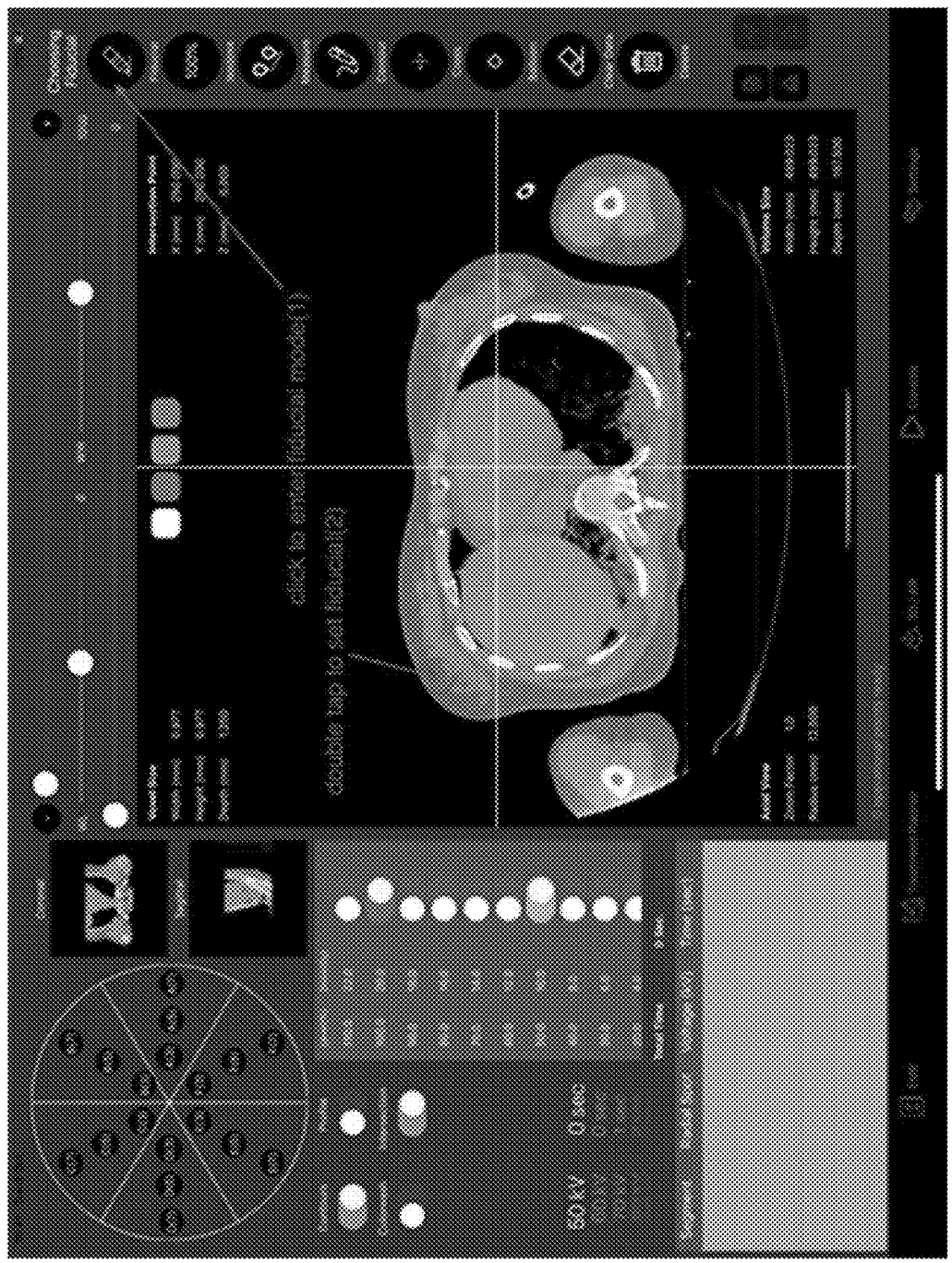
FIG. 33 provides a screen shot of an illustrative GUI that is useful for understanding how fiducial marker locations are set.

Next in 2610, creation of a new treatment plan is initiated by the user by depressing a virtual button (e.g., virtual button 3002 of FIG. 30). The user may also be prompted to input a name for the new treatment plan as shown in FIG. 31. The present solution is not limited in this regard. In other scenarios, a pre-created treatment plan is selected (e.g., from a list of previously created treatment plans) rather than the initiation of a new treatment plan creation. The pre-created treatment plan may be a pre-approved treatment plan or a pending treatment plan that still needs to be approved (e.g., by using a virtual button 1726 of GUI 1700 shown in FIG. 17). If the pre-created treatment plan comprises a pre-approved treatment plan, then the pre-created treatment plan is unable to be edited by the user and is set for treatment (i.e., sent to the robotic sculpted beam IORT system). If the pre-created treatment plan comprises a pending treatment plan, then the pre-created treatment plan is editable by the user and is set for treatment upon the user's approval of the same.

When the user initiates the creation of a new treatment plan, treatment planning software (e.g., application 1622 of FIG. 16) is launched by the user's computing device (e.g., computing device 102 of FIG. 1), as shown by 2612. The treatment planning software provides the user with a GUI (e.g., GUI 1700 of FIG. 17 or GUI 3200 of FIG. 32) in 2614 displaying images (e.g., images 1800-1806 of FIG. 18 or images 3202-3206 of FIG. 32) in various anatomical imaging modality views for the patient selected from the electronic patient roster.

The anatomical imaging modality views may include, but are not limited to, a sagittal image view, an axial image view, and/or a coronal image view. The displayed images may include, but are not limited to, a sagittal image (e.g., image 1804 of FIG. 18 or image 3206 of FIG. 32), an axial image (e.g., image 1800 of FIG. 18 or image 3202 of FIG. 32), and a coronal image (e.g., image 1806 of FIG. 18 or 3204 of FIG. 32). A first image of these images (e.g., image 1804 of FIG. 18 or image 3202 of FIG. 32) is displayed in a center of an image display portion (e.g., portion 1702 of FIG. 27 or portion 3208 of FIG. 32) of the GUI (e.g., GUI 1700 of FIG. 17 or GUI 3200 of FIG. 32), while the other two images (e.g., images 1800 and 1806 of FIG. 18 or images 3204 and 3206 of FIG. 32) are displayed on the side of the first image within the image display portion. The user is able to toggle the display focus between these images, for example, to identify an optimal treatment delivery location. The optimal treatment delivery location is identified using fiducial marker location visible in the images. The image to which focus has been toggled is shown with a larger size than that of the other two images. Once the optimal treatment delivery location has been identified, then the user sets the same, for example, by clicking or touching the fiducial marker locations shown in the images. An illustrative GUI that is useful for understanding how the fiducial marker locations are set is provided in FIG. 33.

The user is also able to change one or more characteristics of the GUI and/or image(s) being displayed in the GUI window (e.g., display 1654 of FIG. 16). The GUI characteristics include, but are not limited to, window size and/or window width. The image characteristics include, but are not limited to, size, contrast, and/or brightness. The GUI/image characteristics may be adjusted for optimizing the visual appearance of the objects shown in the images.

The user is further able to scroll through imaging data's slices. The user may further zoom in and out of any displayed plane for any selected imaging data slice.

The user may triangulate the anatomical display by selecting a certain area of patient's anatomy. Images of the corresponding viewing planes of the selected area in the patient's anatomy are then displayed within the GUI window.

Figure 34:
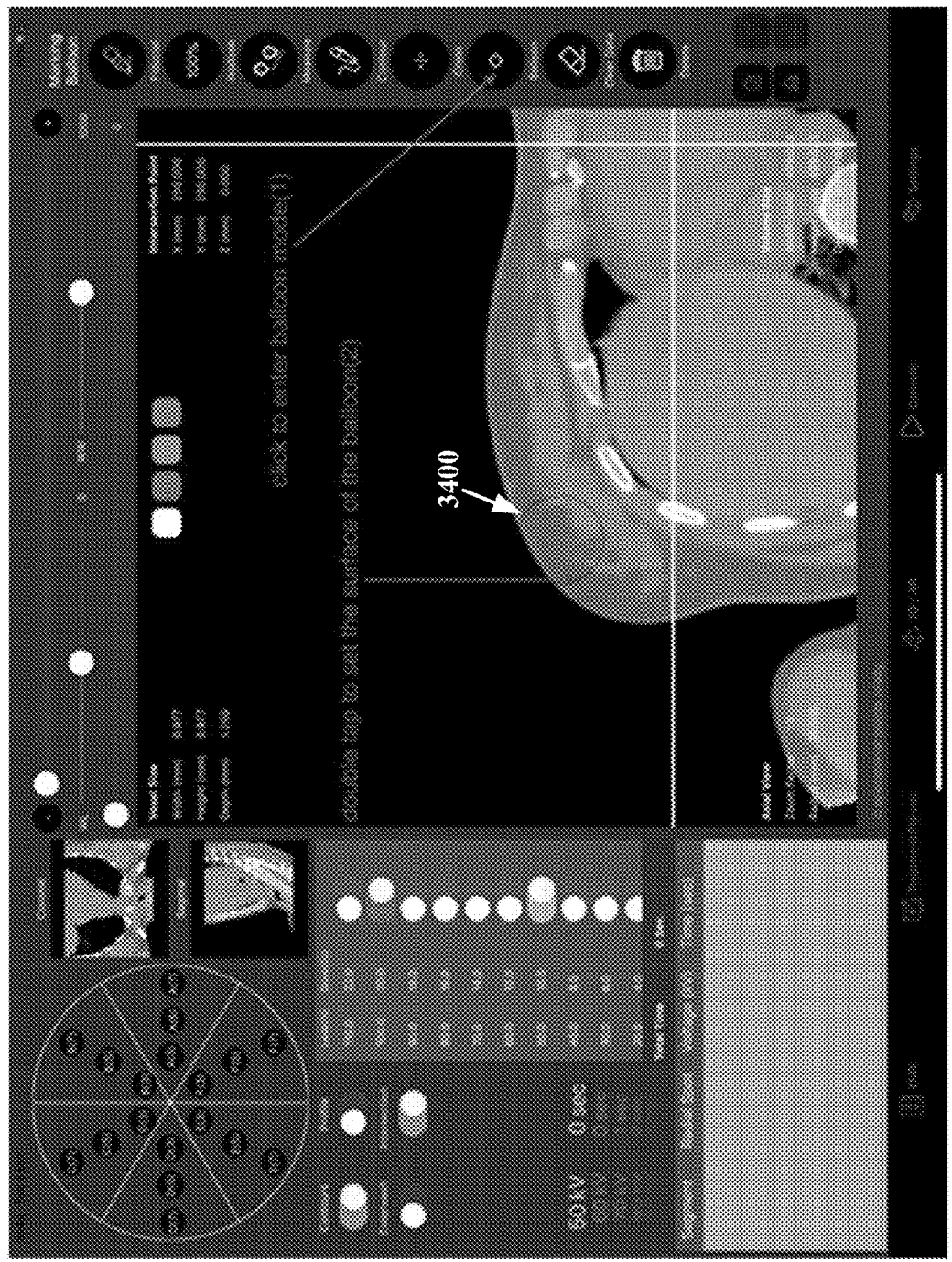
FIG. 34 provides a screen shot of an illustrative GUI showing a balloon volume adjustment.

The user may further adjust the volume of the balloon shown in the GUI. In some scenarios, this balloon volume adjustment is performed to cause the balloon to fill the contours of the tumor bed tissue. An illustration showing the balloon volume adjustment is provided in FIG. 34. In FIG. 34, the balloon is represented by the dotted line 3400. The present solution is not limited in this regard.

In some scenarios, the optimal treatment delivery location is automatically determined by the TPS, rather than manually by the user as described above. For example, the TPS performs operations to: fuse 3D pre-operation images (e.g., CT images) with real time X-ray images (e.g., Tomosynthesis images) to register fiducial marker locations within the 3D pre-operation images; and using the fiducial marker locations to identify a designated treatment anatomical location. The designated treatment anatomical location facilitates a determination as to how an X-ray source will be positioned relative to the patient's body.

In 2614, anatomical image parameters (e.g., parameters 1808 of FIG. 18) and/or a dose rate spectrum (e.g., dose rate spectrum 1810 of FIG. 18) are also displayed within the GUI. The anatomical image parameters include, but are not limited to, voxel width, voxel height, voxel depth, image size in pixels and metric units (size per pixel), a zoom rate, a location of a selected triangulation spot, a selected slice index number, and/or a relative view depth in a patient anatomy. The dose rate spectrum is displayed as a reference guide and baseline for the user.

In 2618, the user selects an anatomical region of the patient and a view mode (e.g., axial, coronal, or sagittal) via the GUI. Next in 2620, symbols (e.g., a circle 1702 and/or cross(es) 1704 of FIG. 17) representing a treatment head (e.g., treatment head 316 of FIG. 3) and the fiducial markers contained in the treatment head are presented in the GUI so as to be overlaid on top of the image in focus (e.g., image 1800 of FIG. 18). These symbols allow the user to visualize and/or know the location and orientation of the treatment head relative to the patient's body represented by the displayed images.

The GUI is designed to allow the user to manually adjust the location and/or orientation of the treatment head relative to the patient's body (e.g., by pointing and double-clicking at a desired location in the GUI window). Accordingly, method 2600 includes optional 2620 where the user adjusts the position of the treatment head relative to the patient's body by manipulating the location and/or orientation of the respective symbol(s) within the GUI.

In 2622, the TPS receives user inputs for identifying one or more treatment area(s). Next in 2624, the TPS either performs operations to automatically mark the isodose contours of the identified treatment areas or receives user inputs for marking the isodose contours of the identified treatment areas. The user inputs can be facilitated using an input device (e.g., a stylus, a trackball, and/or a mouse) and/or a gesture. A first contour is marked by the TPS or the user for an area of the patient's body that is to receive a radiation dose of a minimum intensity. A second contour is marked by the TPS or the user for an area of the patient's body that is to receive a radiation dose of a maximum intensity. A third contour, and any additional contour, may also be marked for an area of the patient's body that is to receive a radiation dose(s) of any desired intensity(ies).

The operations performed by the TPS to automatically calculate and display the isodose contours involve: drawings areas where radiation is to be deposited; and calculating beam characteristics using one or more beam defining algorithms. Beam defining algorithms are well known in the art, and therefore will not be described herein. Any known or to be known beam defining algorithm can be used herein. For example, a beam forming algorithm is employed here which comprises a combined implementation of a Monte Carlo algorithm based on GEANT4 simulation toolkit. The Monte Carlo algorithm and GEANT4 simulation toolkit are well known in the art, and therefore will not be described herein.

Figure 35:
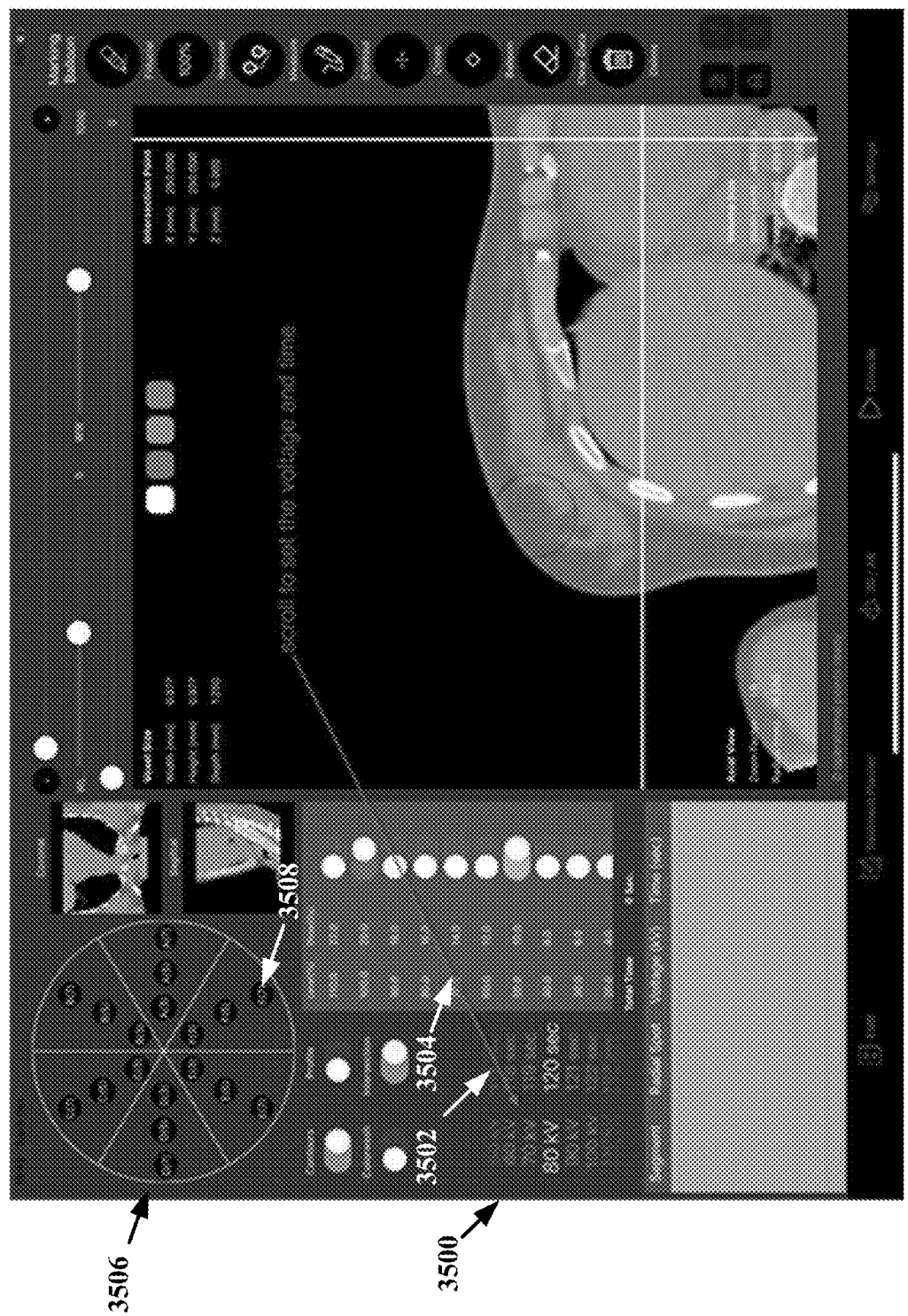
FIGS. 35-36 provide screen shots of illustrative GUIs showing how a user chooses operational points using widgets.
Figure 36:
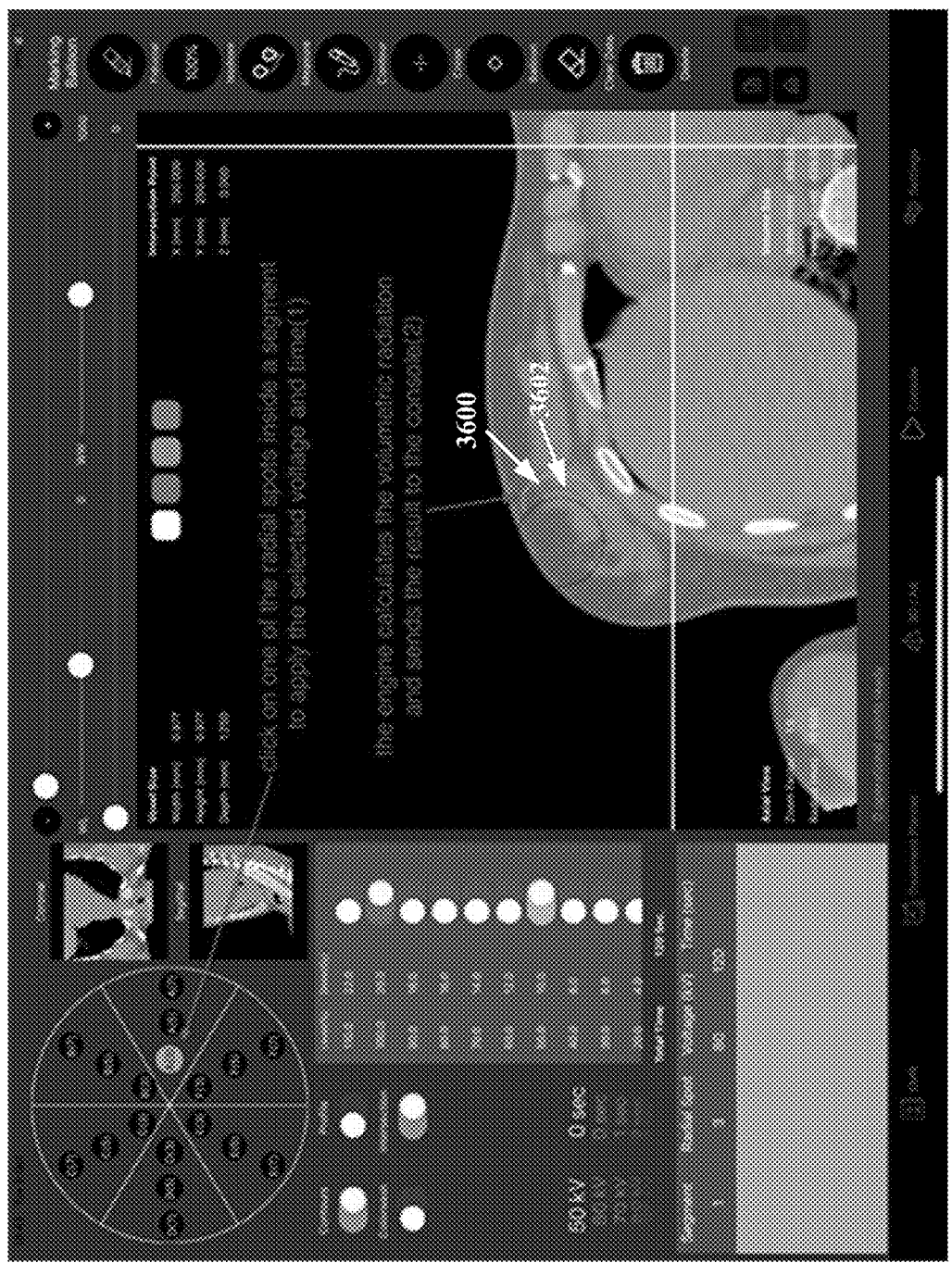
Figure 37:
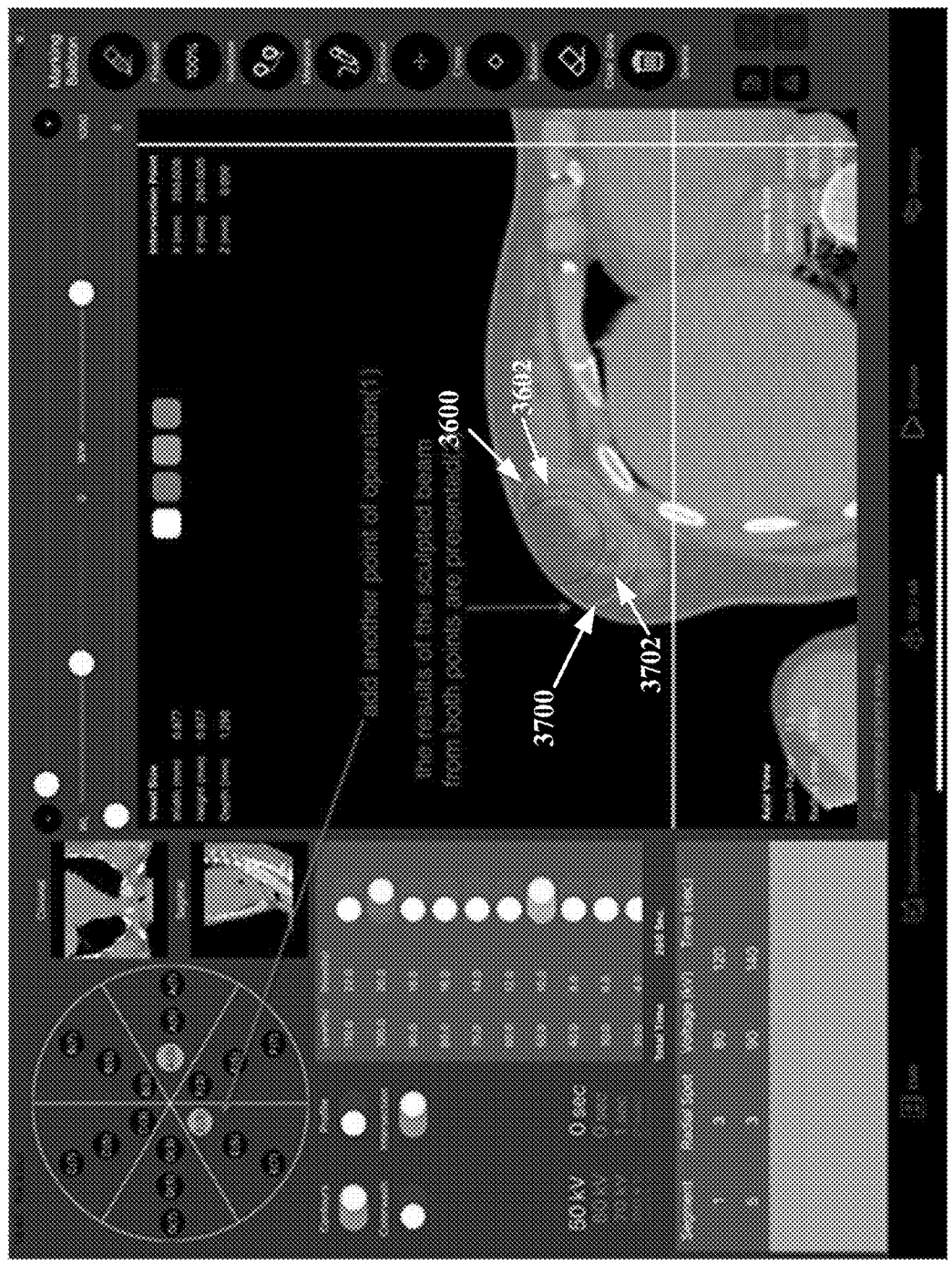
FIG. 37 provides a screen shot of an illustrative GUI showing isodose contours in a toggled on state.
Figure 38:
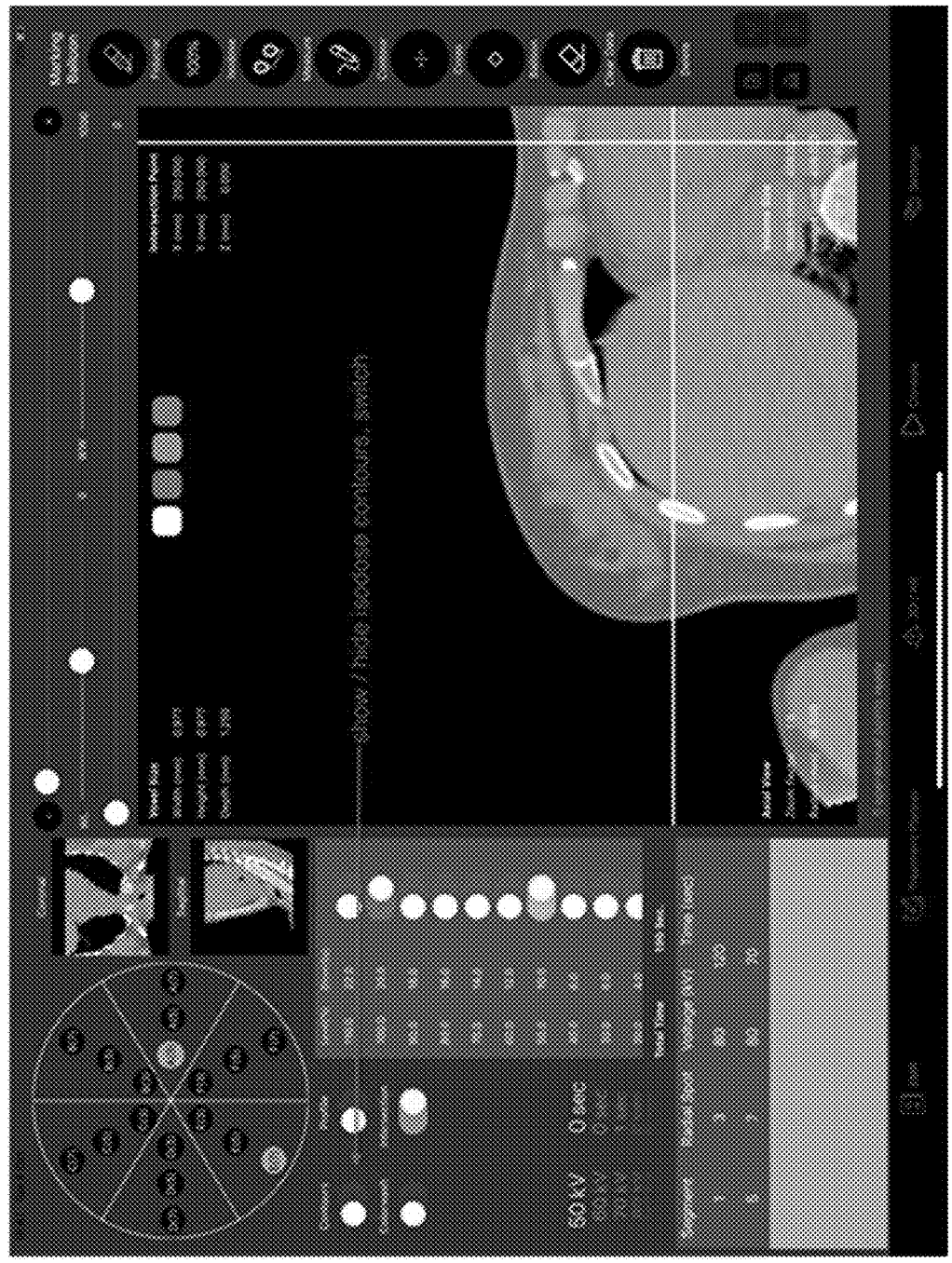
FIG. 38 provides a screen shot of an illustrative GUI showing isodose contours in a toggled off state.
Figure 39:
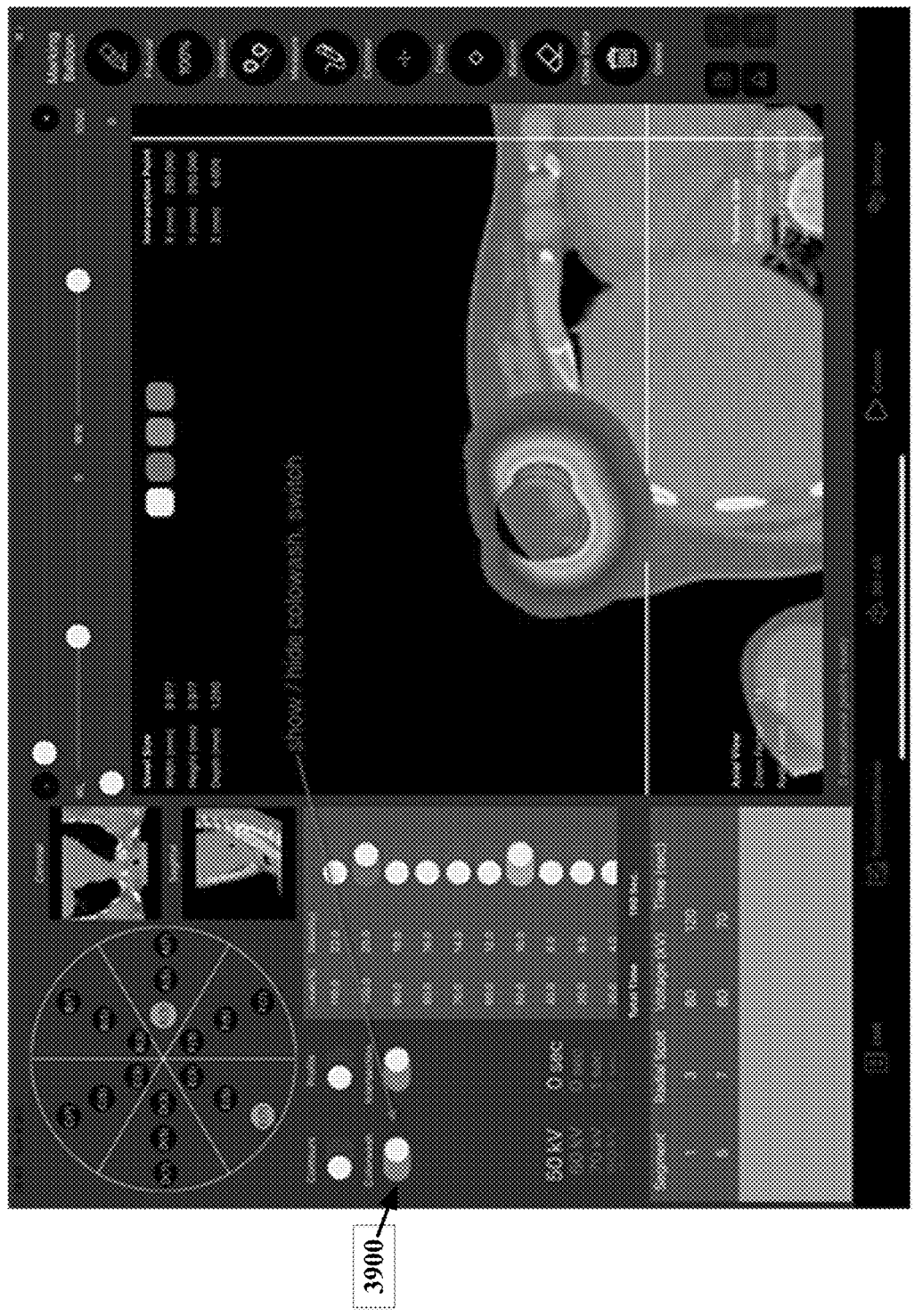
FIG. 39 provides a screen shot of an illustrative GUI showing a widget that can be used to toggle a colorwash on and off.
Figure 40:
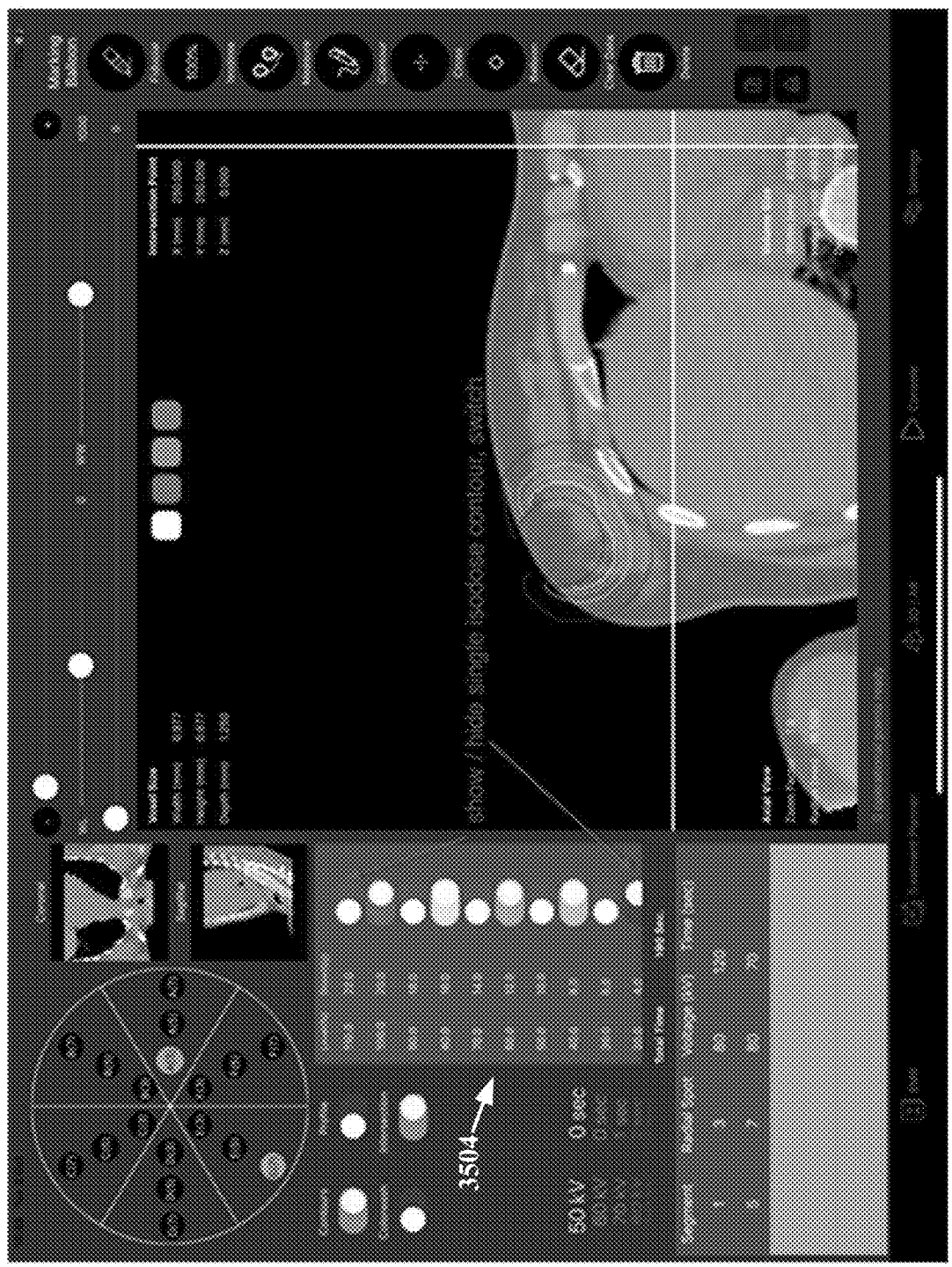
FIG. 40 provides a screen shot of an illustrative GUI showing additional intermediary dose boundaries.
Figure 41:
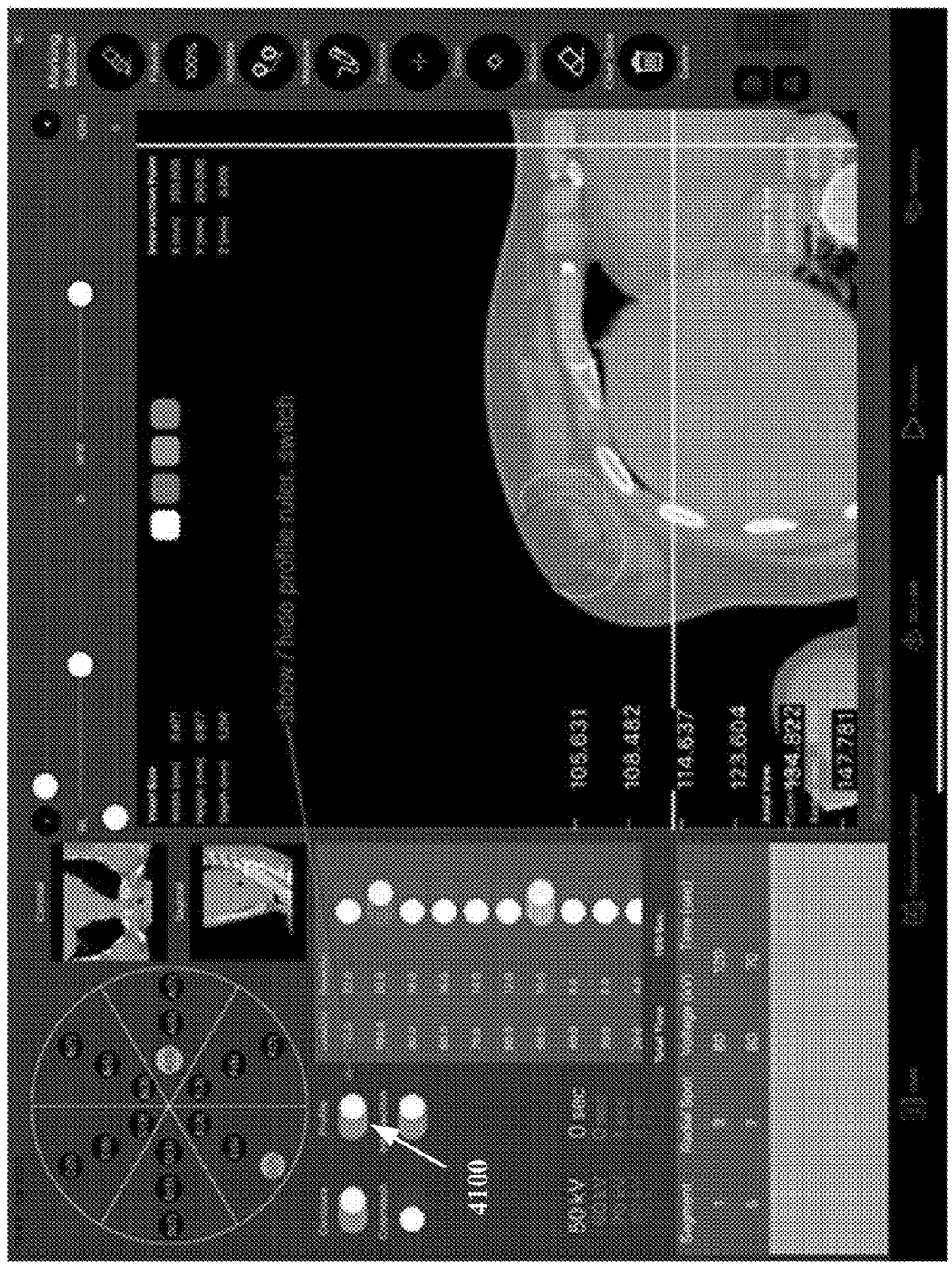
FIG. 41 provides a screen shot of an illustrative GUI showing a profile ruler in a toggled on state.

The operations performed by the user to calculate and display the isodose contours can involve adjusting the minimum intensity level and the maximum intensity level using widgets of the GUI (e.g., widgets 1712 and/or 1714 of FIG. 17 or widgets 3500-3506 of FIG. 35). For example, the user performs the following actions to define beam characteristics as shown in FIGS. 35-36: select an energy in kilovolts using widget 3500 of FIG. 35; select a dwell time using widget 3502 of FIG. 35; and select a dwell point (e.g., A(3)) from a plurality of dwell points 3508 in area 3506 of FIG. 35. In response to these user actions, the TPS calculates the volumetric radiation or volume of the beam in accordance with the selected energy, dwell time and dell points. The TPS also provides a visual indication of the beam structure and registration on the images. For example, the TPS displays lines 3600, 3602 on the GUI. Line 3600 represents a 50% dose boundary, while line 3602 represents a 100% dose boundary. The present solution is not limited to the particulars of this example. These actions can be repeated in relation to any number of dwell points (e.g., dwell points A(3), A(5), A(7), B(3), B(5), B(7), C(3), C(5), C(7), D(3), D(5), D(7), E(3), E(5), E(7), F(3), F(5), and/or F(7)). Illustrative results from performing a second iteration of these actions is shown in FIG. 37. The user does not have to repeat this operation for every slice. The user can skip slices and the TPS interpolates the missing slices by different algorithms. The system registers every contouring and other user action on the main display slice throughout all anatomical planes.

Figure 42:
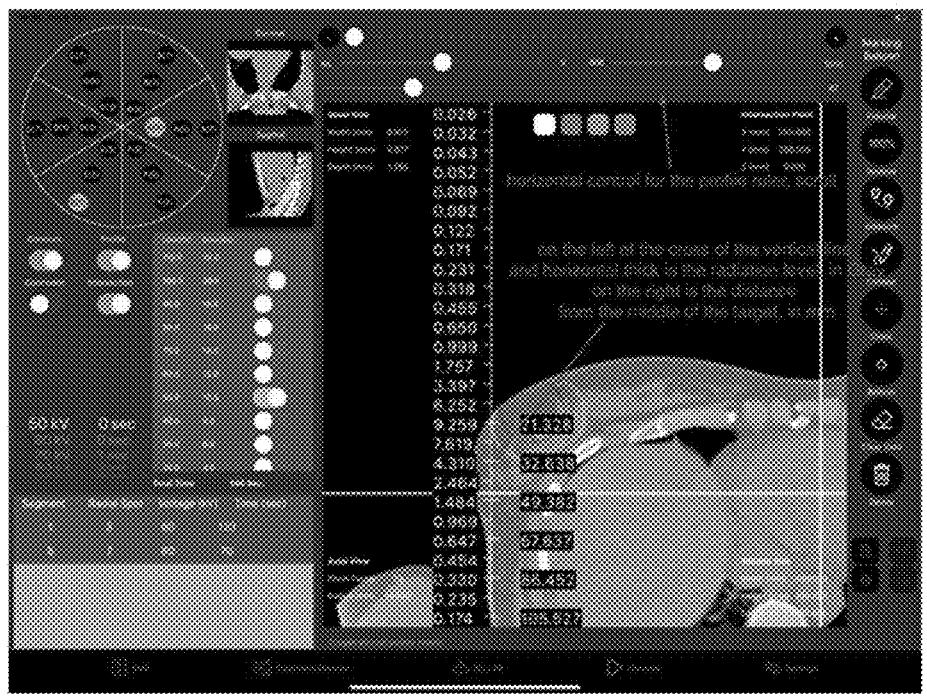
FIGS. 42-43 provide screen shots of illustrative GUIs showing a profile ruler scrolled to different positions or locations of displayed imagery.
Figure 43:

Notably, the isodose contours (e.g., represented by lines 3600, 3602, 3700, 3702 of FIG. 37) can be toggled on and off. An illustration showing the isodose contours toggled on is provided in FIG. 37, while an illustration showing the isodose contours toggled off is provided in FIG. 38. Additionally or alternatively, a colorwash can be toggled on and off using a widget 3900 of FIG. 39, additional dose boundaries can be toggled on and off using widget 3504 of FIG. 35, and/or a profile ruler tool can be toggled on and off using a widget 4100 of FIG. 41. An illustration showing an illustrative colorwash toggled on is provided in FIG. 39. The colorwash represents the radiation beam spectrum. An illustration showing additional intermediary dose boundaries (e.g., 80%, 40%, 20% dose boundaries) is provided in FIG. 40. An illustration showing a profile ruler toggled on is provided in FIG. 41. The profile ruler can be scrolled to see the radiation dose at any specific point. Illustrations showing the profile ruler scrolled to different positions are provided in FIGS. 42 and 43.

Figure 44:
FIG. 44 provides a screen shot of an illustrative GUI that is useful for understanding how a Gray value can be set.

The user may also set the Gray value for the 100% isodose. An illustration that is useful for understanding how the Gray value can be set is provided in FIG. 44. The Gray value can be set to regulate a threshold based on what is to be achieved at a certain percentage of the treatment dose. All other Gray values for the rest of the isodose percentages are calculated automatically after setting the Gray value of the 100% isodose.

Figure 45:
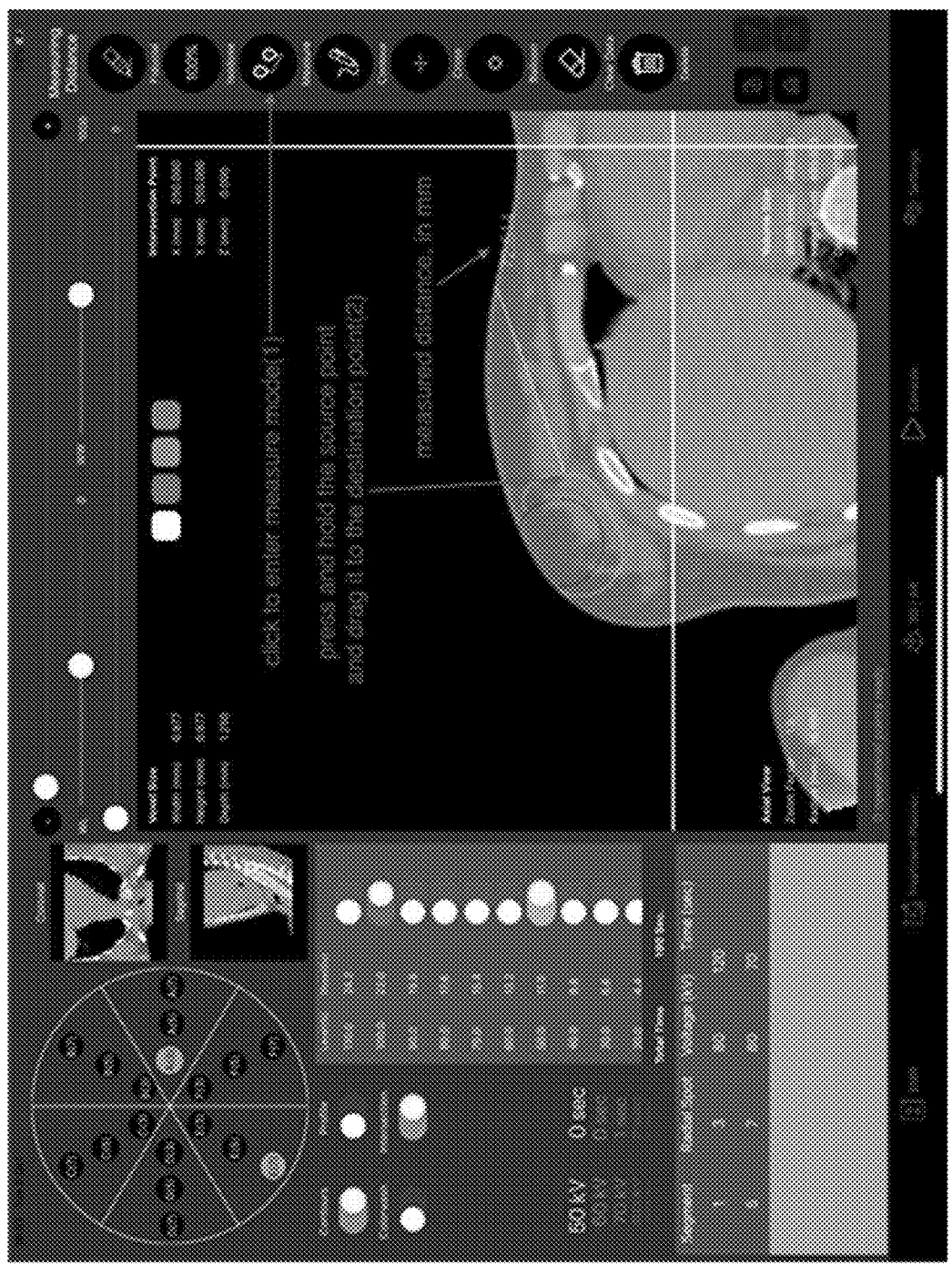
FIG. 45 provides a screen shot of an illustrative GUI that is useful for understanding how a distance measurement can be made.
Figure 46:
FIGS. 46-49 provide screen shots of illustrative GUIs showing how a user marks contours using widgets and the comparison of marked contours with calculated contours.
Figure 47:
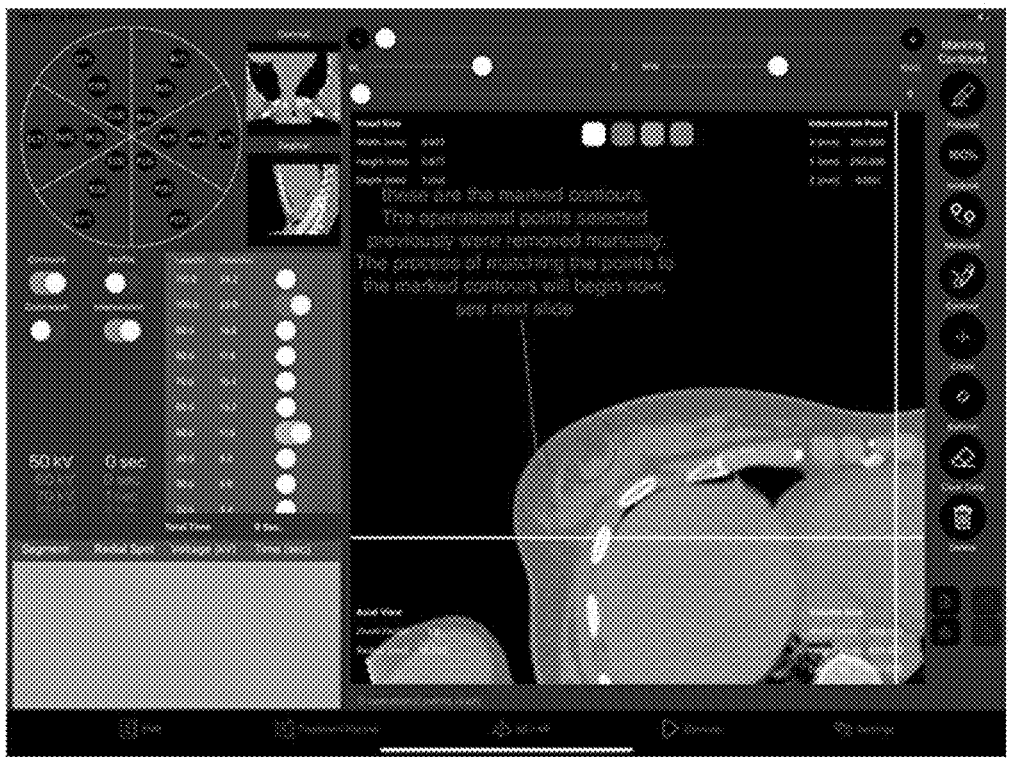
Figure 48:
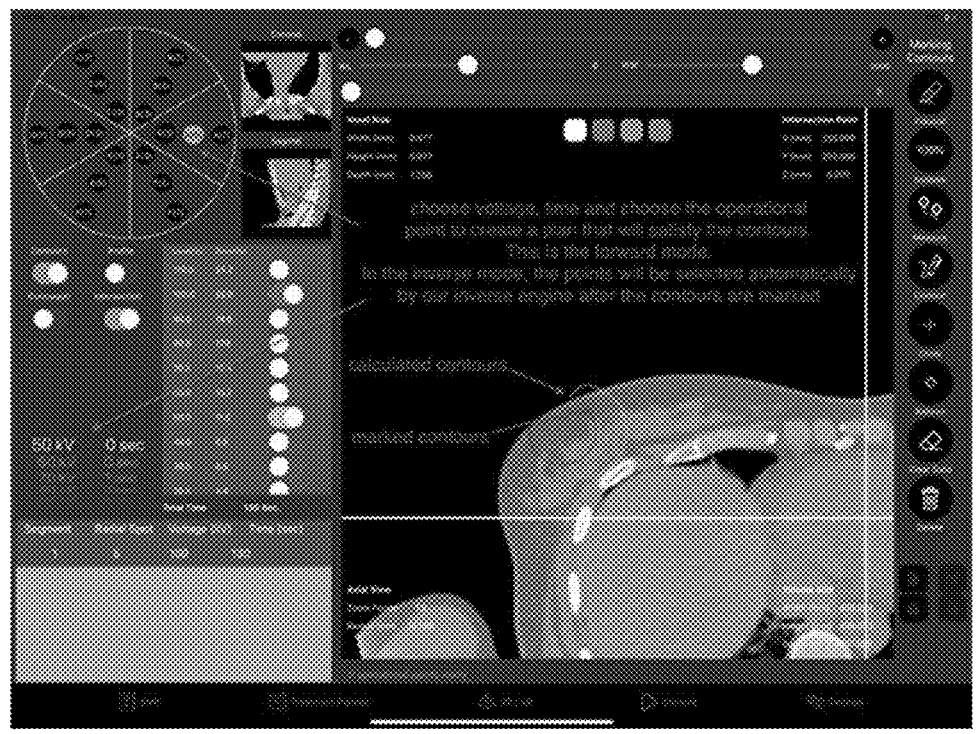
Figure 49:

The user may further measure a distance between any two points. For example, a measurement tool can be used to determine distances in anatomy to make sure that the radiation is not going to be provided to certain areas of the body, such as to organs at risk. An illustration that is useful for understanding how such distance measurements are made is provided in FIG. 45.

Figure 50:
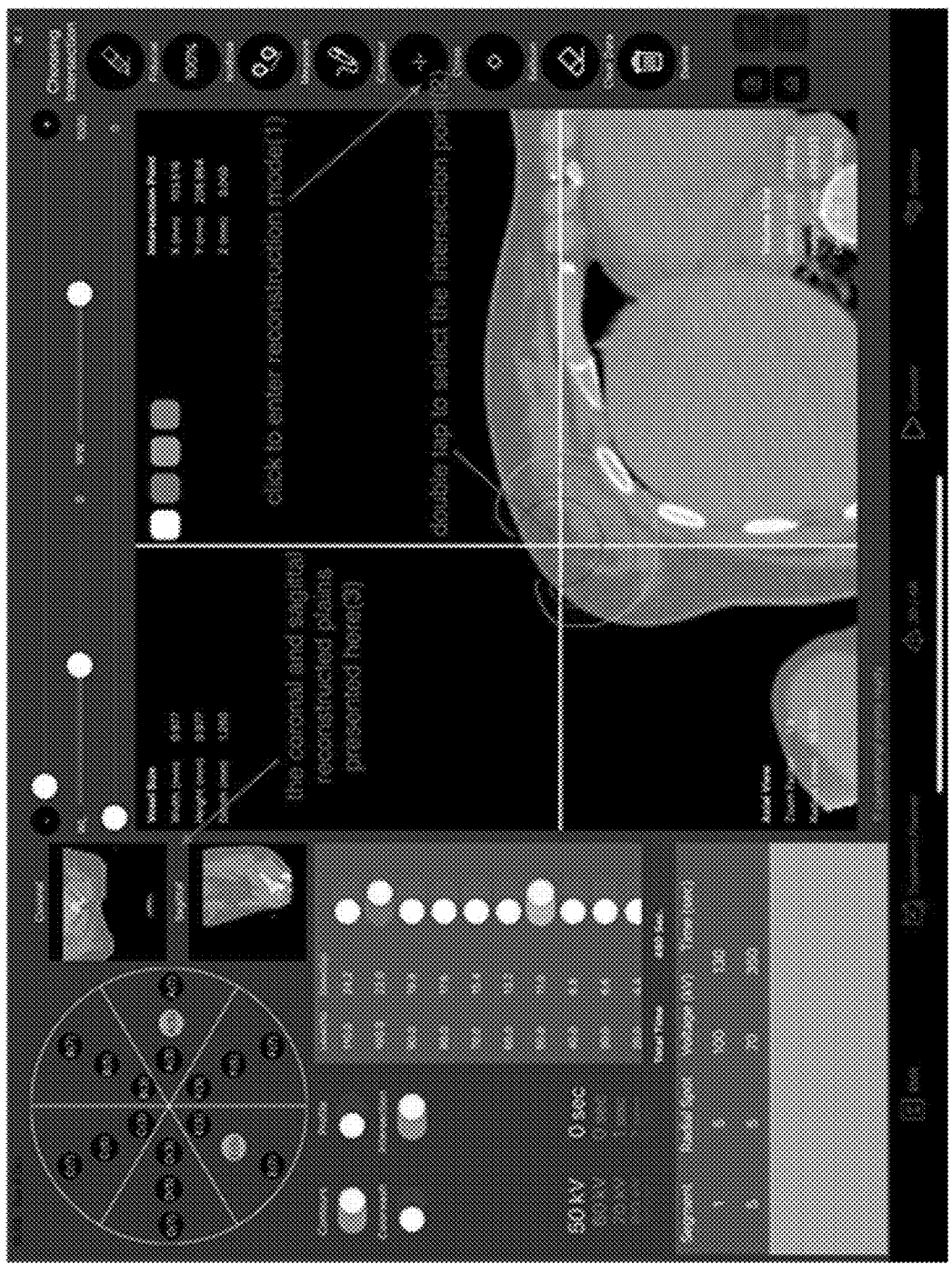
FIG. 50 provides a screen shot of an illustrative GUI showing reconstructed coronal and sagittal planar images.

Subsequently, the contours are marked by selecting a color representing an isodose and by drawings a contour on the GUI (e.g., via gesture, mouse operation, or other pointing device operation). Illustrations showing marked contours are provided in FIGS. 46-49. Next, reconstructed coronal and sagittal planar images are presented. An illustration showing such reconstructed images is provided in FIG. 50.

Upon completing 2624, the user performs user-software interactions in 2626 for initiating a Beam Sculpting Engine Parallel Processor ("BSEPP") simulator. In 2628, the BSEPP performs operations to generate an optimal treatment plan for the selected geometry and topology of the patient's designated anatomy to be treated. The optimal treatment plan is derived from the contours marked in 2624. For example, in some scenarios, the BSEPP performs the following operations: running an iterative computational cycle to optimize a planned sculpted beam's geometry and volume in a most accurate manner to conform with the user's desired minimum and maximum marked radiation dose contours and anatomical volume; and generating a final treatment plan and beam firing sequence to include an energy, a dwell time, and a target segment index/location. In 2630, the BSEPP performs operations to calculate and display a total dwell time of an X-ray source in a given physical location within the applicator.

Figure 26B:
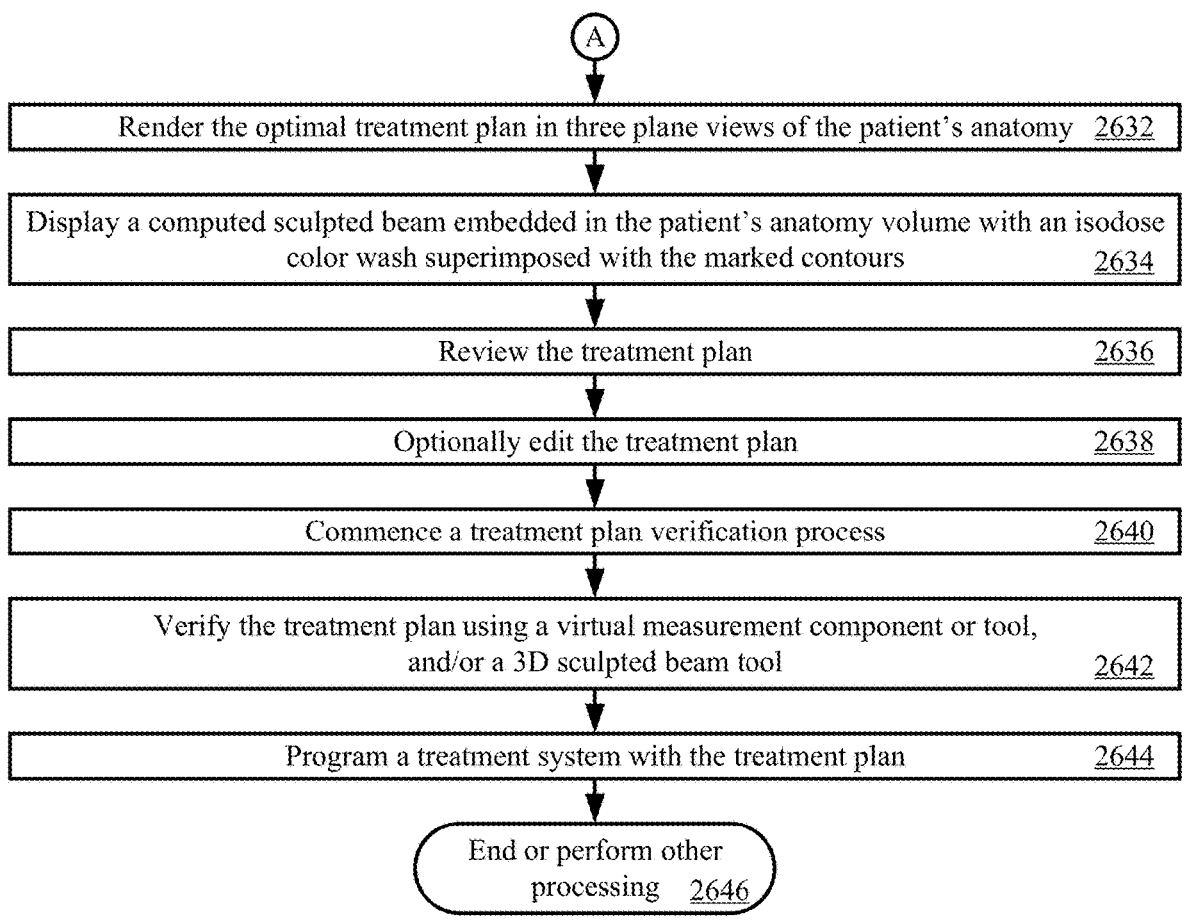

Upon completing 2630, method 2600 continues with 2632 of FIG. 26B. As shown in FIG. 26B, 2632 involves rendering the optimal treatment plan in three plane views of the patient's anatomy. The three plane views can include, but are not limited to, an axial view, a coronal view, and a sagittal view. In 2634, a sculpted beam having the optimized geometry is shown in the GUI as being embedded in the patient's anatomy volume with isodose contours and/or color wash. The isodose contours and/or color wash show optimal actual dose shaping compared to the target volume defined by the user marked contours. The user has the ability to toggle between a color wash view, an isodose curves contour view, and a clear view in which no color wash or isodose curves contour is presented.

In 2636, the user reviews the treatment plan in 2636 using the GUI. The treatment plan may optionally be edited by the user in 2638. For example, the user may modify a firing sequence of an electron beam of an X-ray source 410, change a Target Sculpting Factor ("TSF"), and an X-ray source's translation rate. The TSF includes a target segment index, a hit position within a segment, an energy level (e.g., in kV), and a dwell time (e.g., in seconds). The present solution is not limited to the particulars of this example.

Thereafter in 2640, a treatment plan verification process is commenced. The system provides the user with one or more dedicated tools in 2642 to assist in the treatment plan verification process.

One such tool comprises a virtual measurement component (e.g., virtual measurement component 2100 of FIG. 21). The tool can be moved by the user with a pointing device (e.g., a stylus, trackball, or mouse) or via a gesture to scan vertically or horizontally through the patient's anatomy and rendered sculpted beam geometry. Once the tool crosses through the anatomical image pixel, the tool displays a reference distance measurement from the center of the target, and an absorbed dose in each anatomical image pixel. Once the tool reaches the sculpted beam area, the tool begins to display the actual deposited dose at its location, the scale of the pixel size for the given anatomy view, and the isodose threshold of the reviewed sculpted beam area. The virtual measurement component also measures and displays the distance between two spots on the image main view, in order to provide the user with an additional reference and scale verification of the sculpted beam vs. the patient's anatomy.

Another such tool comprises a 3D sculpted beam tool. The 3D sculpted beam tool is specifically designed for the robotic sculpted beam IORT systems, and can be initialized by depressing a virtual button 1812 presented on the GUI. The 3D sculpted beam tool has to ability to create an omni-morphic beam geometry. The omni-morphic beam geometry can be created using a beam forming algorithm. For example, the omni-morphic beam geometry is created using an algorithm that comprises a combined implementation of a Monte Carlo algorithm and a GEANT4 simulation toolkit. The Monte Carlo algorithm and GEANT4 simulation toolkit are well known in the art, and therefore will not be described herein. The 3D sculpted beam tool renders a computed sculpted beam in 3D (an isosphere) and fuses it through three anatomical plane cross sectional displays. The 3D sculpted beam tool then intersects the three view planes (axial, coronal, and sagittal) through the isocenter of the X-ray source and target volume, and renders the sculpted beam volumetric geometry through the three plane views. This provides the user with an ultimate view of how the beam penetrates through the targeted treated anatomy and how the dose is being deposited in every voxel, all in reference of adjacent organs and tissue that the user may want to avoid or prevent any therapeutic dose deposition at. The 3D sculpted beam tool also includes and renders the user's drawn contours that are fused in the same 3D view of the sculpted beam in the patient's anatomy. While running the 3D sculpted beam tool, the user can move each anatomical plane axis and view the corresponding cross-sectional sculpted beam profile and dose deposition.

Figure 51:
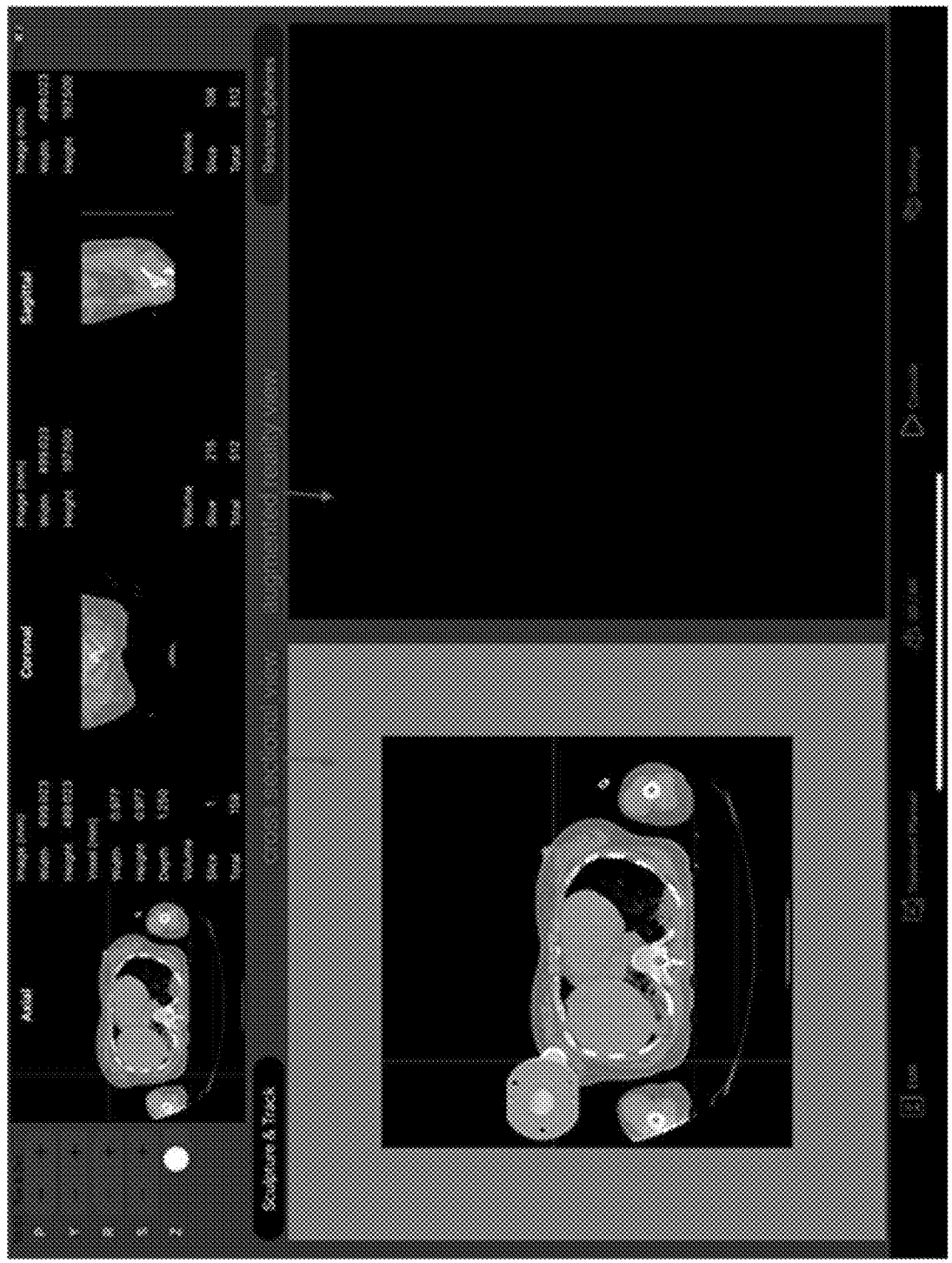
FIGS. 51-59 provide screen shots of illustrative GUIs that are useful for understanding a 3D sculpted beam tool to verify a treatment plan.
Figure 52:
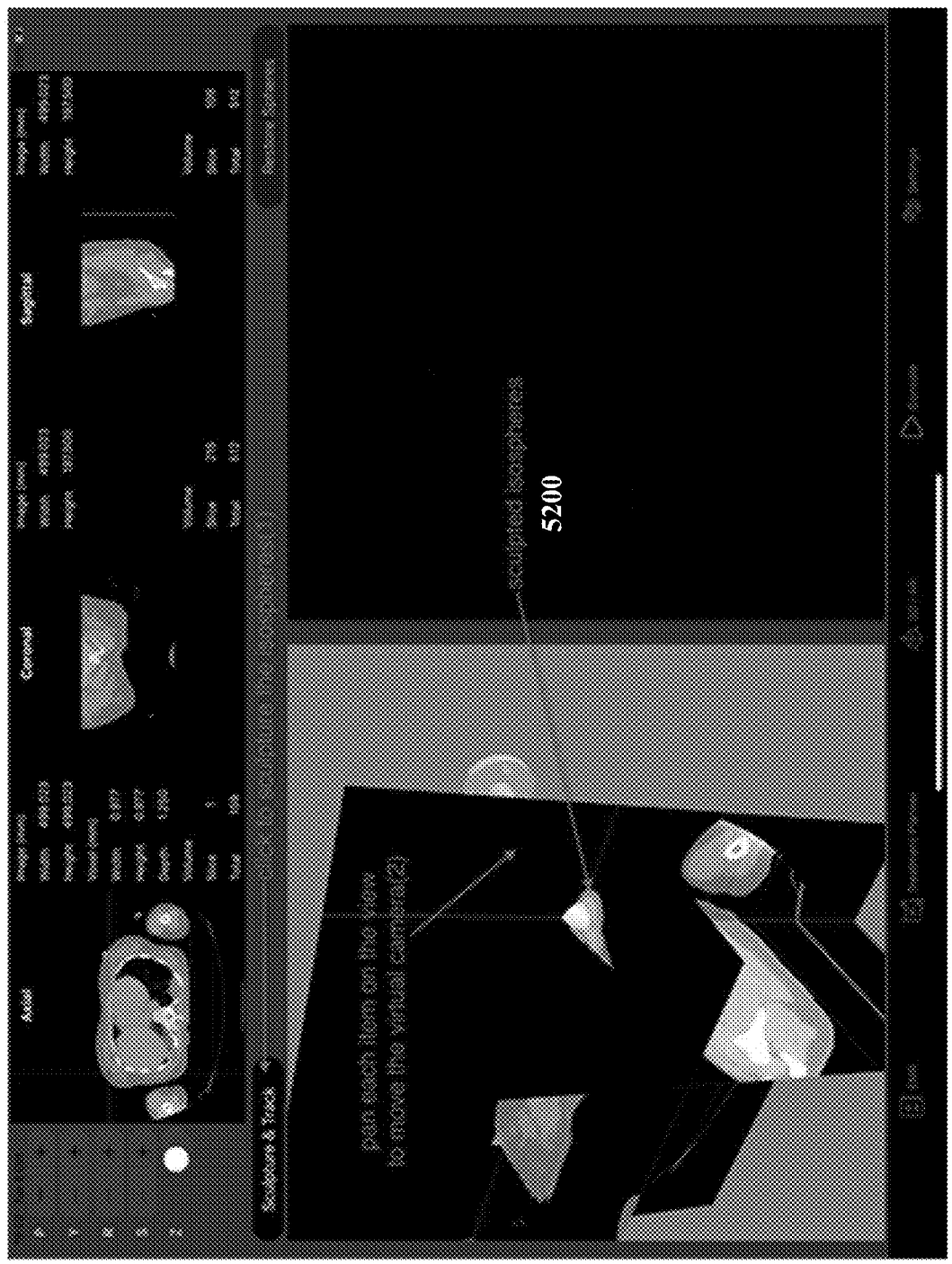
Figure 53:
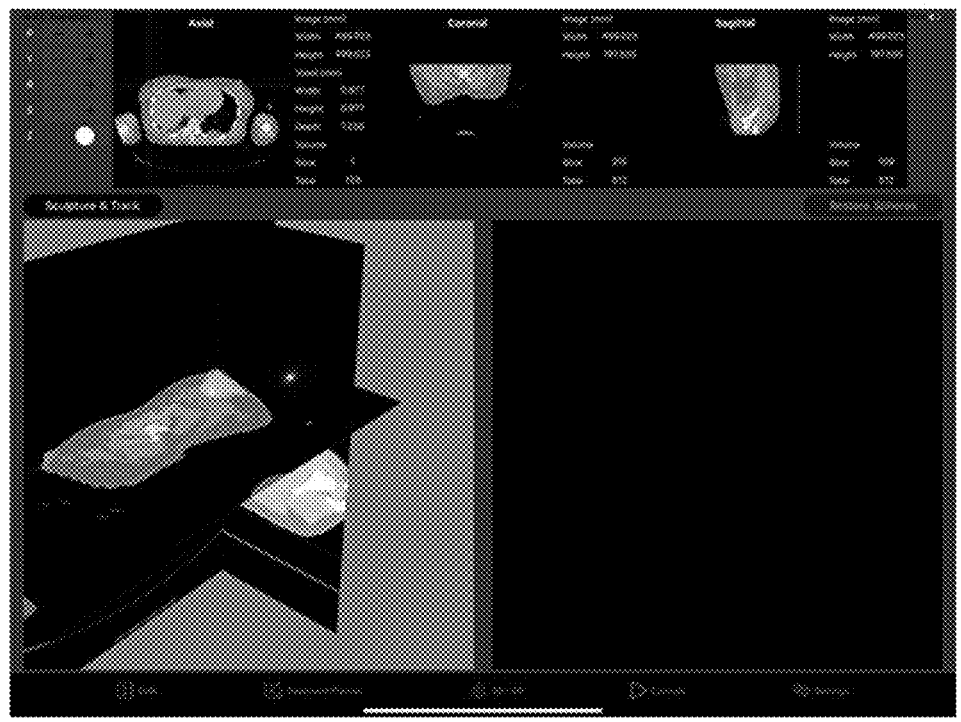
Figure 54:
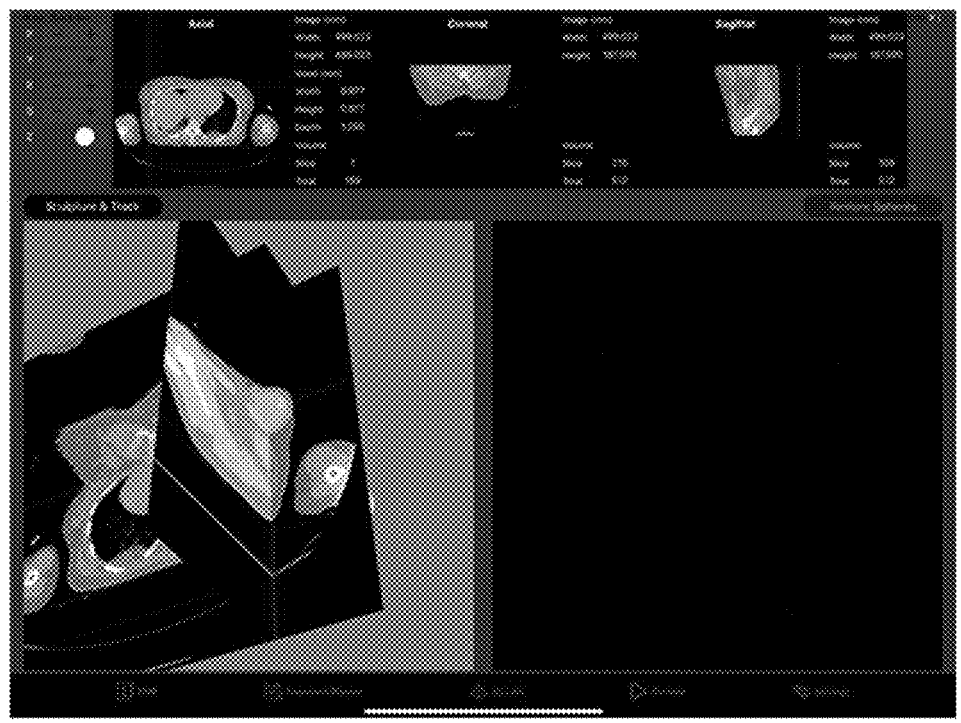
Figure 55:
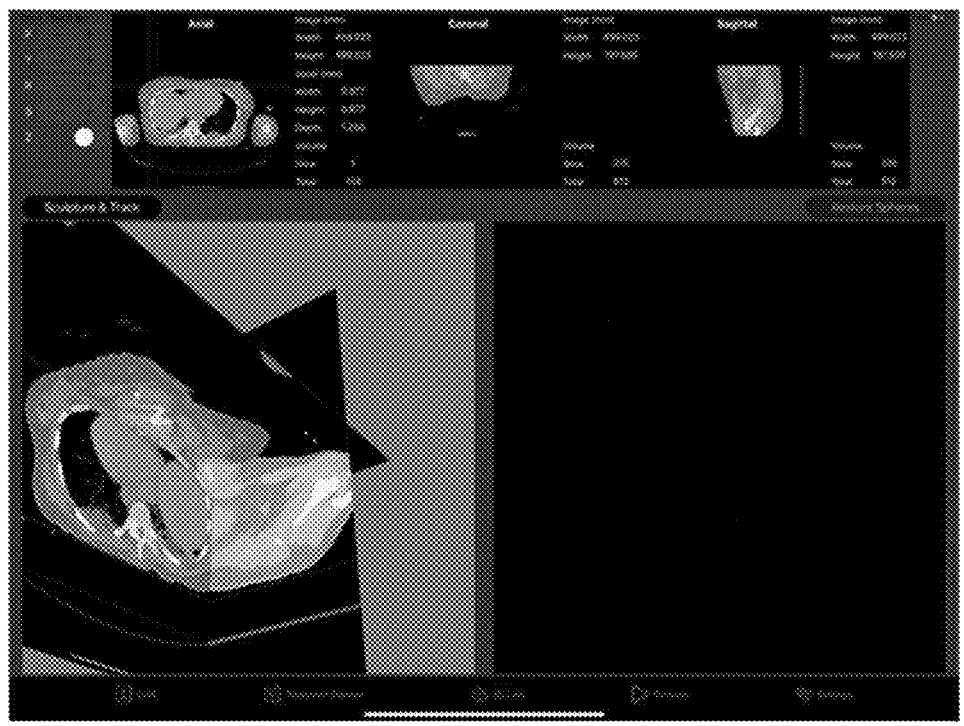
Figure 56:
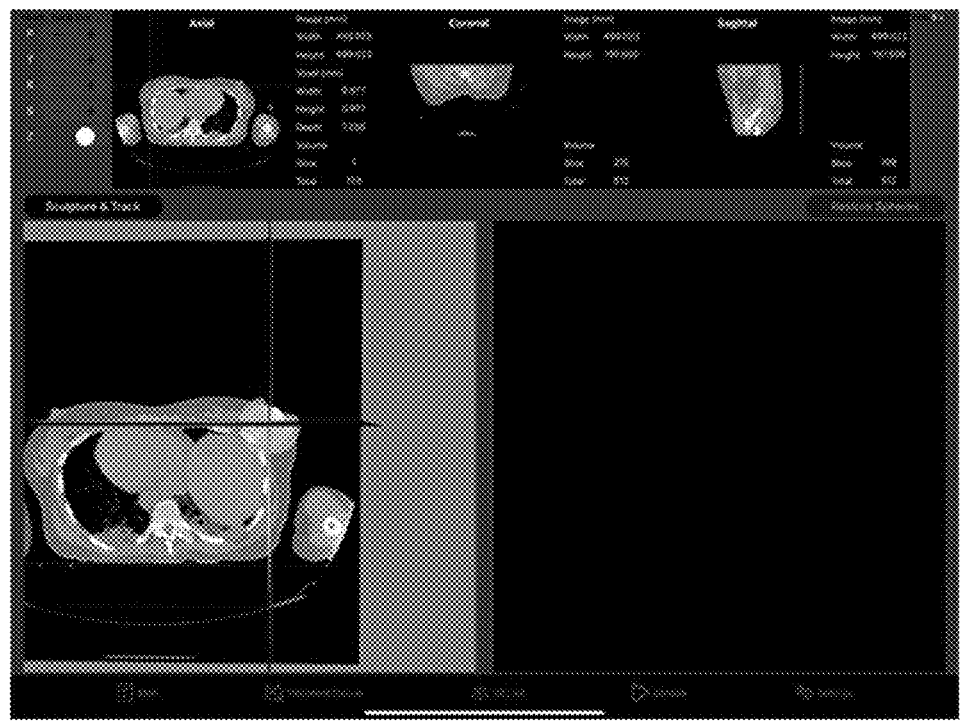
Figure 57:
Figure 58:
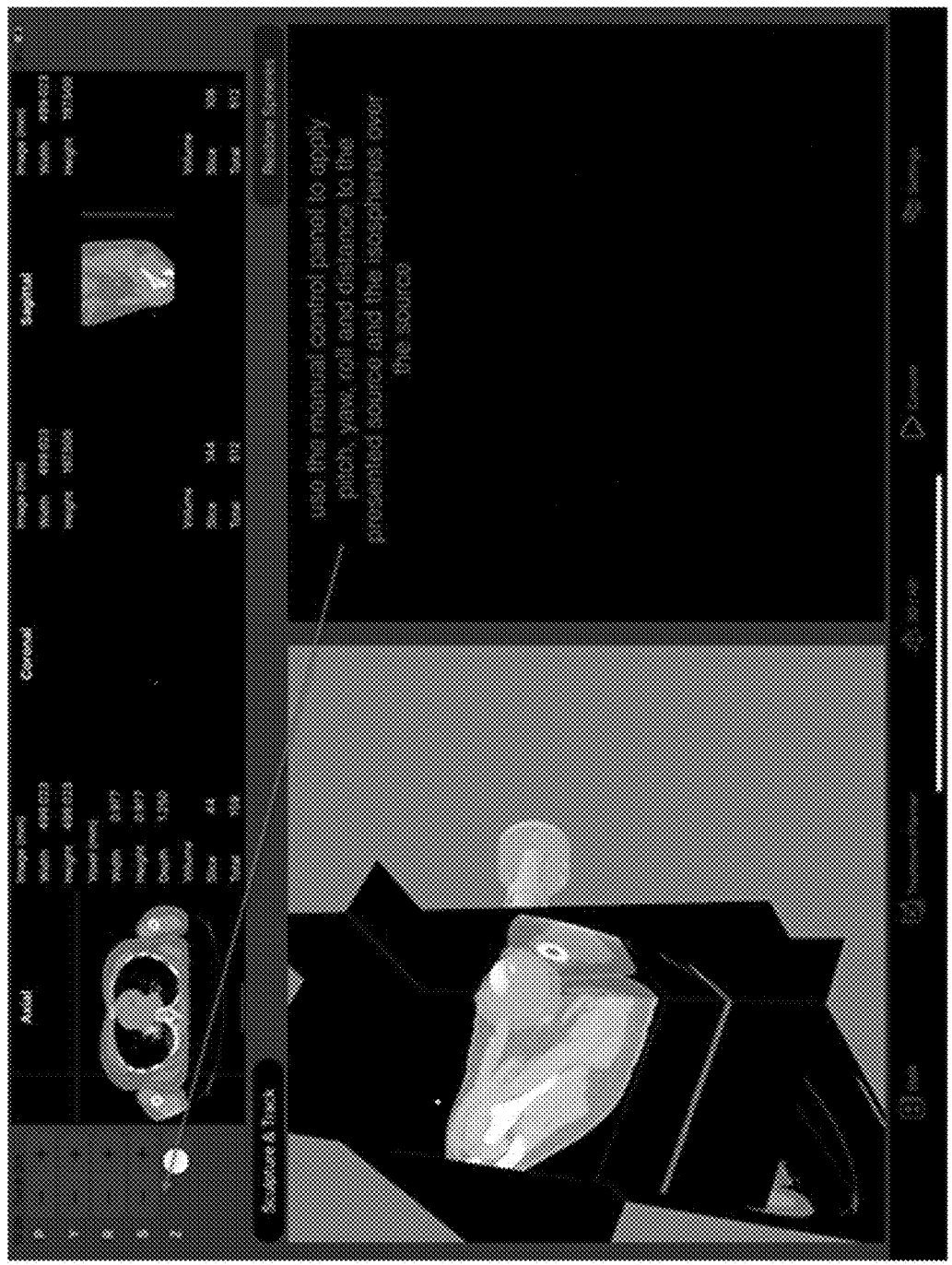

Illustrations that are useful for understanding the 3D sculpted beam tool are provided in FIGS. 51-59. In FIG. 51, the user performs user-software interactions for opening a 3D viewer. In response to the user-software interactions, the 3D sculpted beam tool presents a 3D image showing a source of radiation relative to a 3D anatomy of the patient. Next, the 3D sculpted beam tool prepares the model and renders 3D isopheres showing the beam shape inside the anatomy of the patient. The rendered 3D isopheres allow a user to see how a dose or beam will be distributed inside the patient or other anatomical treatment target. An illustration showing rendered 3D isopheres 5200 is provided in FIG. 52. The 3D view can be rotated so that the user can view the rendered 3D isopheres 5200 from different perspectives relative to the patient's anatomy within the GUI. Illustrations showing different views of the rendered 3D isopheres 5200 are provided in FIGS. 53-56. The user may also toggle the rendered 3D isopheres on and off. An illustration showing a rendered 3D isophere for a 50% dose in a toggled off state is provided in FIG. 57. In effect, the rendered 3D isophere for a 100% dose can be seen more clearly in FIG. 57.

Figure 59:
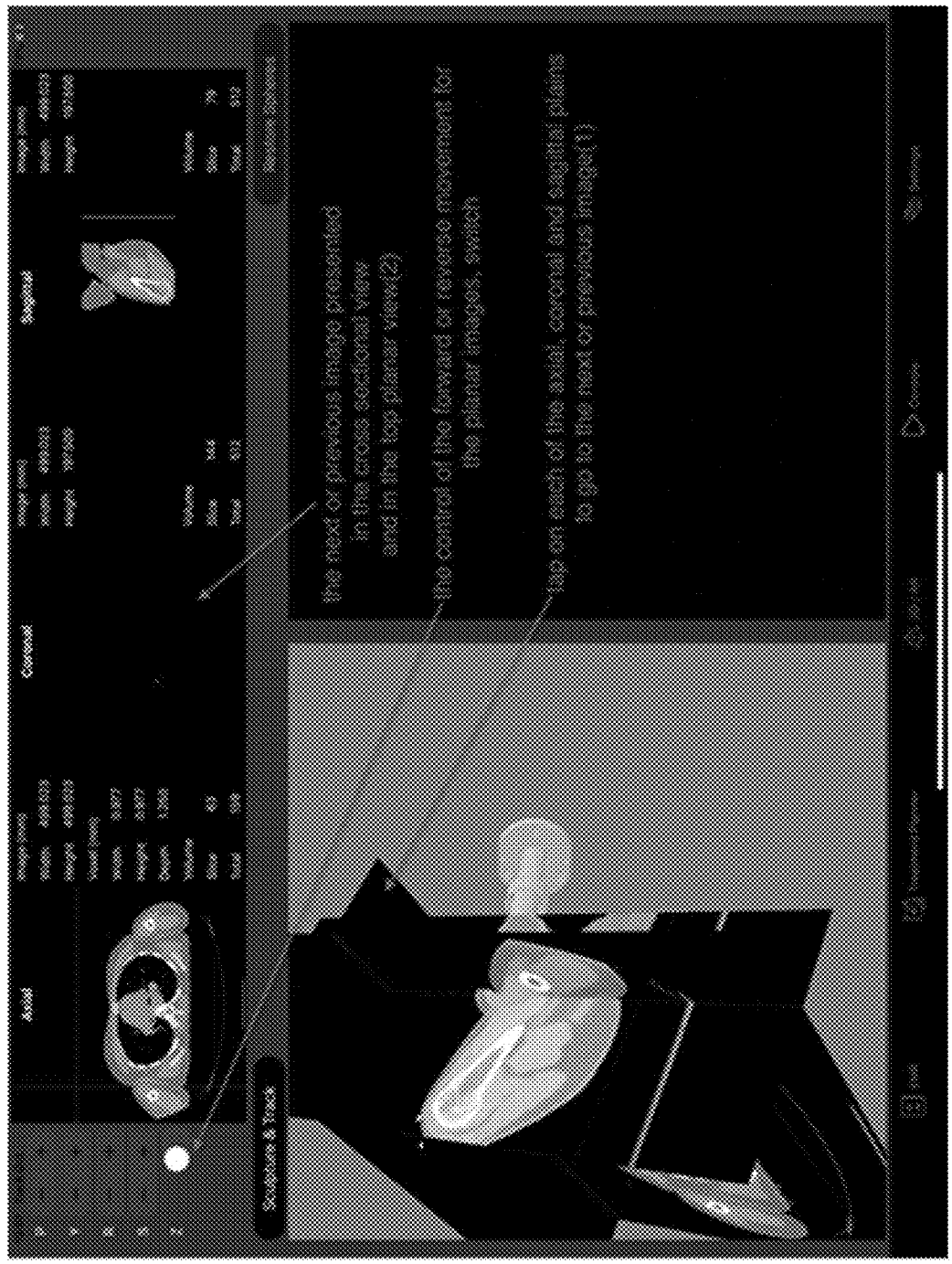
Figure 60:
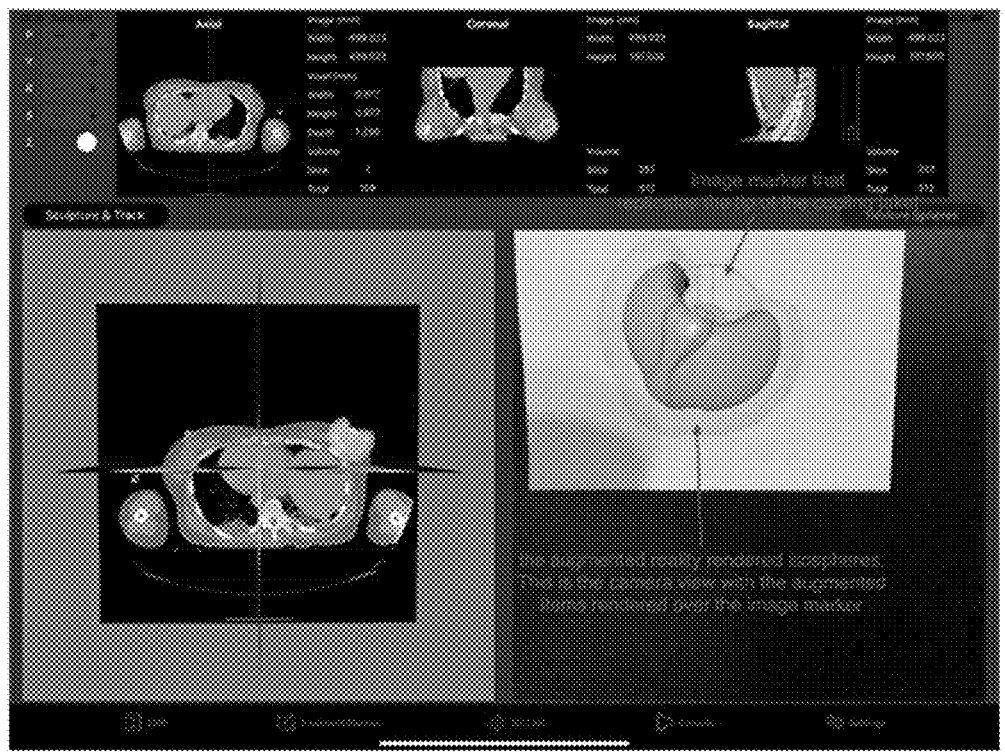
FIGS. 60-68 provide screen shots of illustrative GUIs showing use of an Augmented Reality ("AR") tool to verify a treatment plan.
Figure 61:
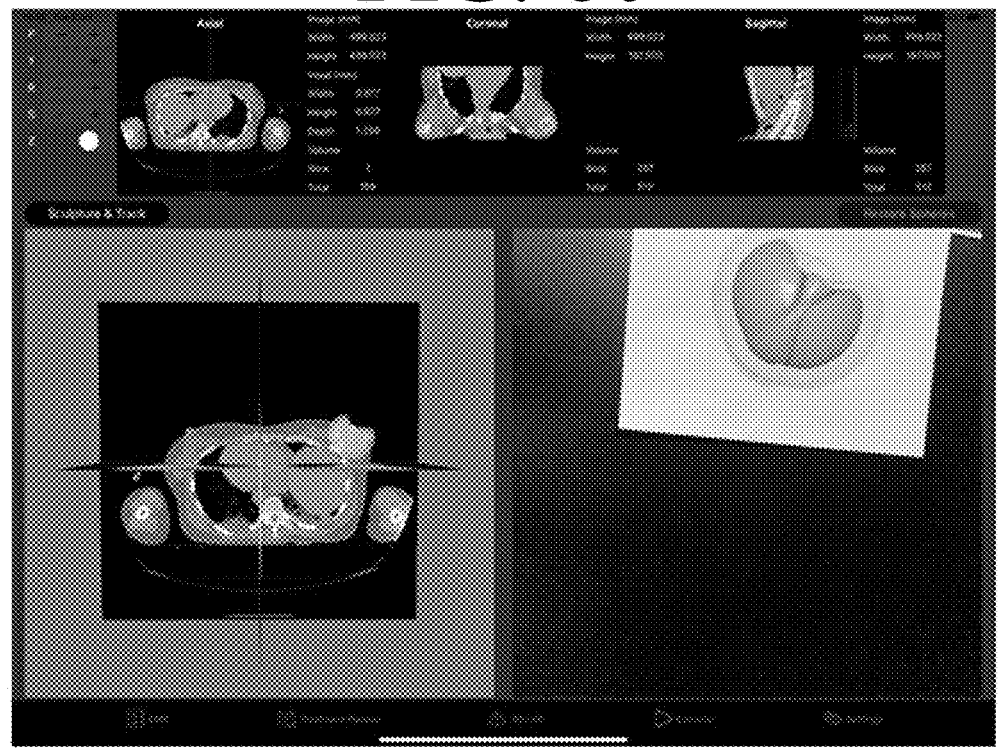
Figure 62:
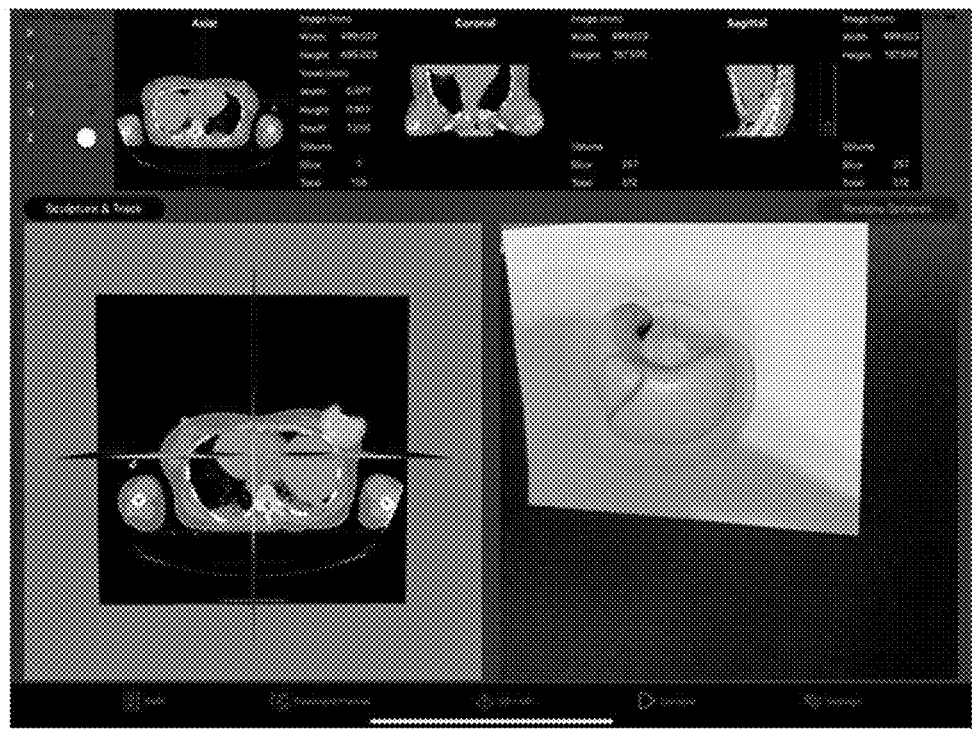
Figure 63:
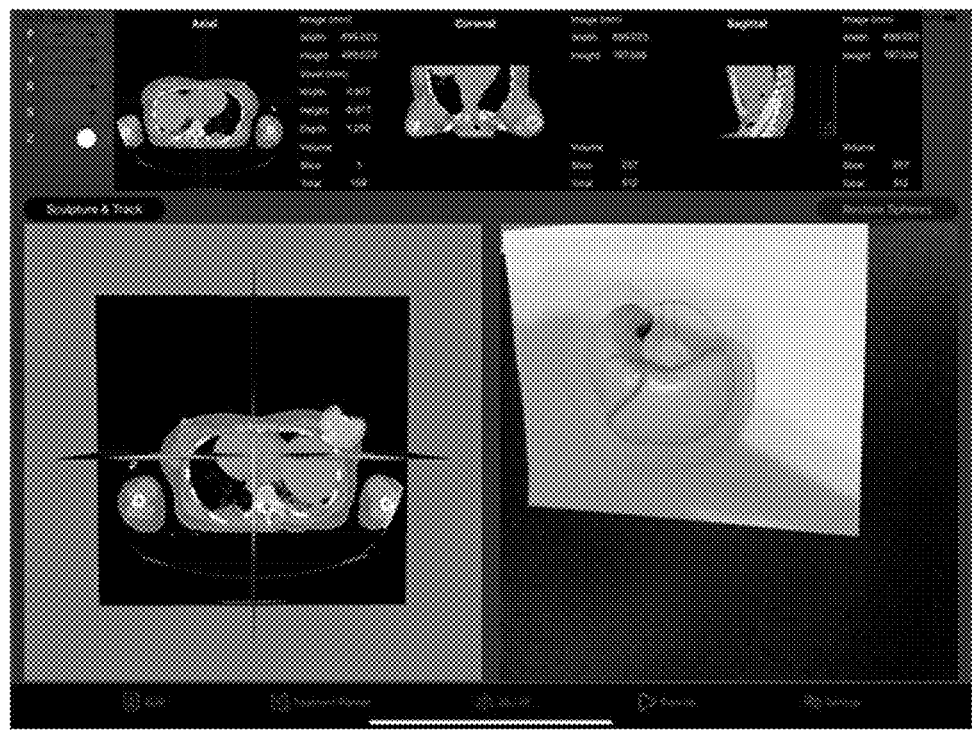
Figure 64:
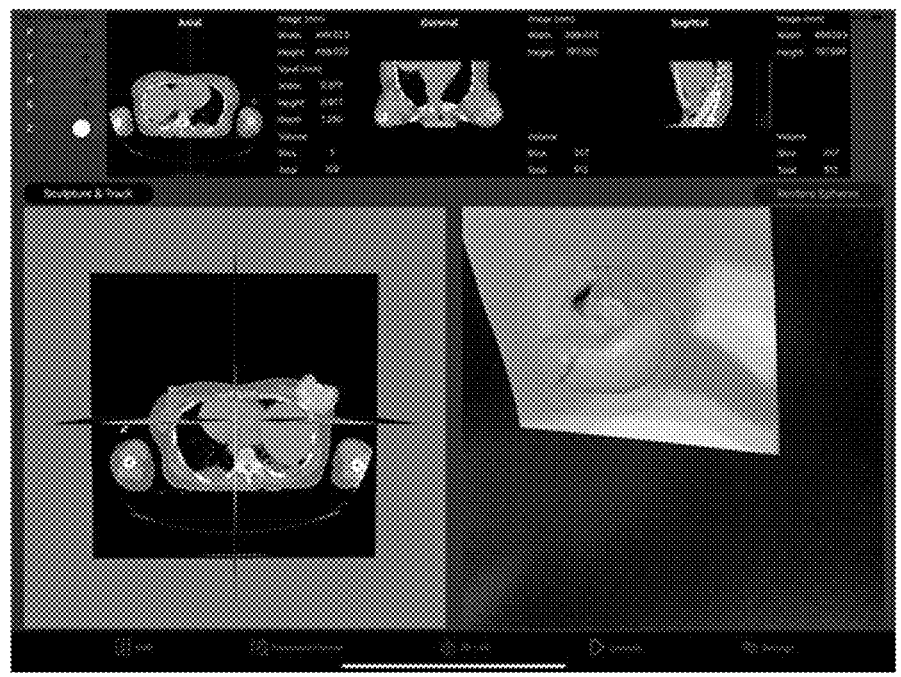
Figure 65:
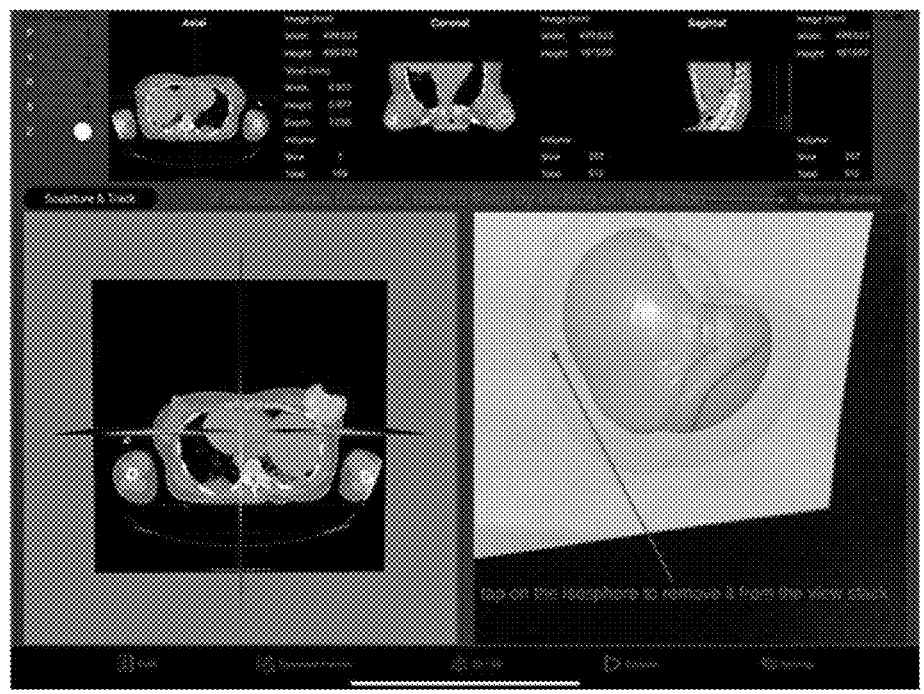
Figure 66:
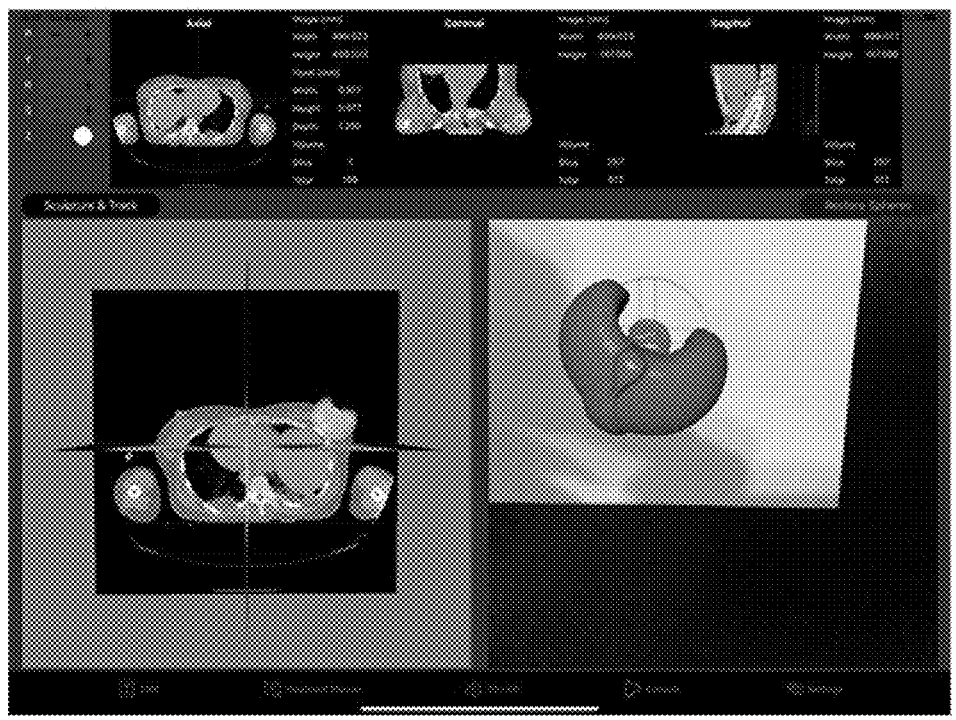
Figure 67:
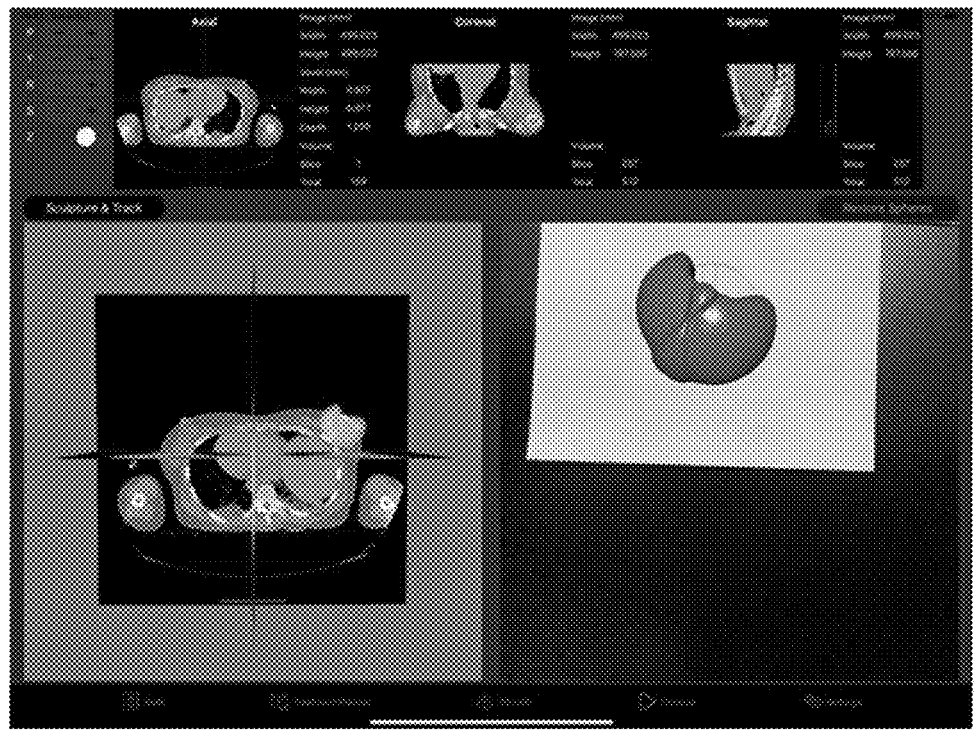
Figure 68:
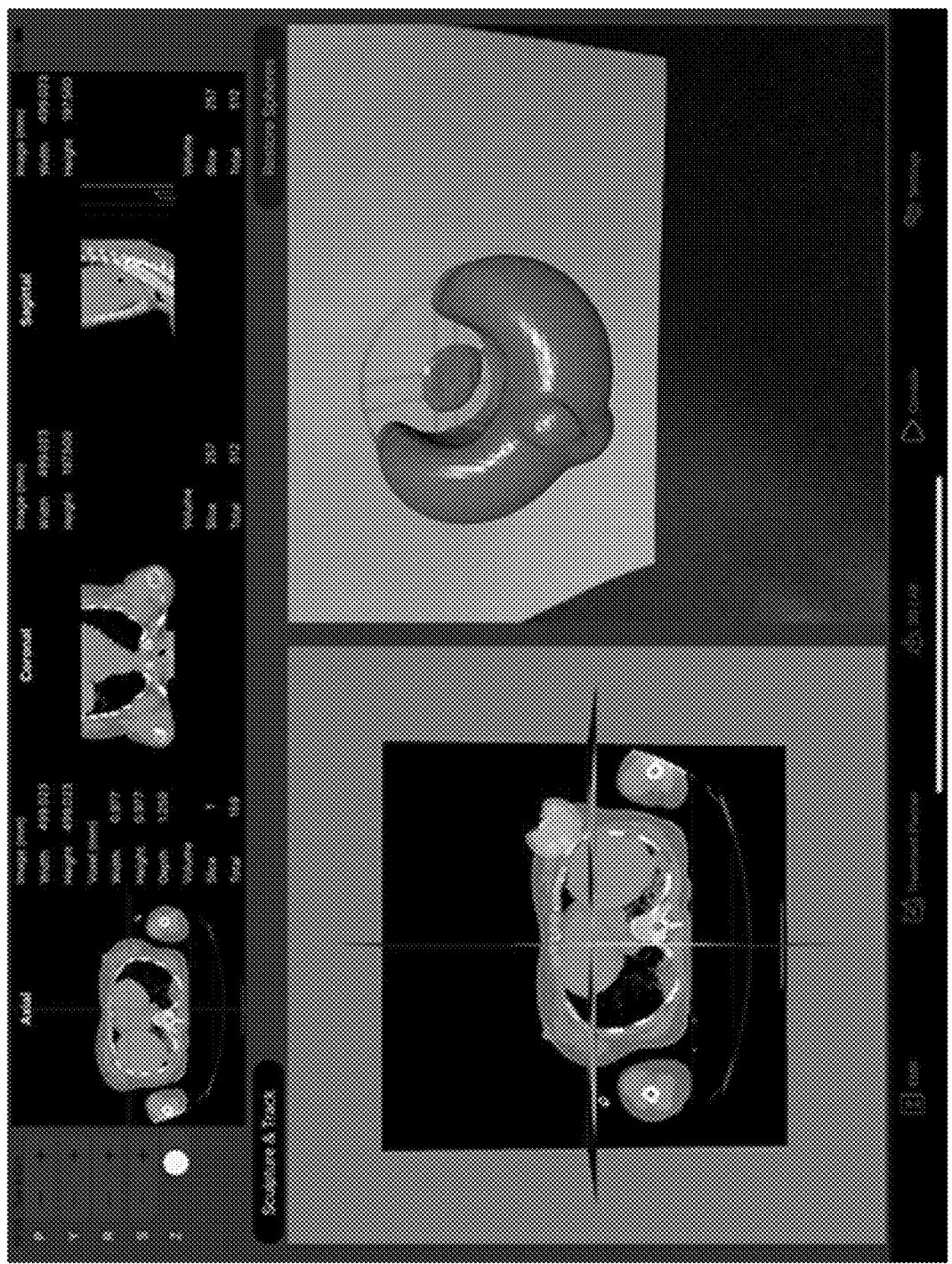

The user may further move the source relative to the person's anatomy within the GUI. An illustration that is useful for understanding how the source is moved within the GUI is provided in FIG. 58. The source movement can be performed to make adjustments to how the source is positioned in an anatomy to fine tune the actual location of the source during treatment. The user may also move the axial, coronal and sagittal images as shown in FIG. 59.

Another such tool comprises an Augmented Reality ("AR") tool. The AR tool can be implemented using a portable device with a camera and/or AR glasses. The AR glasses can include, but are not limited to, the AR glasses described in U.S. patent application Ser. No. 15/946,667 filed on Apr. 5, 2018 (published as U.S. Patent Publication No. 2018/0289983). Illustrative GUIs showing use of the AR tool are provided in FIGS. 60-68.

The system does not require the user to manually save the data of the treatment plan alongside the planning process. The system does that automatically at every step the user creates and works on. The data is being automatically logged and saved onto the system's relational database engine (that may be powered by MySQL®, MSSQL®, or other available relational database engines on the market). The system can operate with either a relational or non-relational database engines.

Once the treatment plan is verified and approved by the user, a treatment system (e.g., treatment system 106 of FIG. 1) is programmed with the treatment plan in 2644. The treatment system can then perform operations to apply radiation to the patient in accordance with the programmed treatment plan. Subsequently, 2646 is performed where method 2600 ends or other processing is performed.

Although the present solution has been illustrated and described with respect to one or more implementations, equivalent alterations and modifications will occur to others skilled in the art upon the reading and understanding of this specification and the annexed drawings. In addition, while a particular feature of the present solution may have been disclosed with respect to only one of several implementations, such feature may be combined with one or more other features of the other implementations as may be desired and advantageous for any given or particular application. Thus, the breadth and scope of the present solution should not be limited by any of the aforementioned described embodiments. Rather, the scope of the present solution should be defined in accordance with the following claims and their equivalents.

What is claimed is:

1. A method for radiation therapy, comprising:
acquiring at least one image of a treatment area using a robotic sculpted beam radiation treatment system;
presenting, by a mobile computing platform, the at least one image in a Graphical User Interface ("GUI");
creating a real-time beam sculpting treatment plan for a patient based on user inputs to the mobile computing platform via the GUI;
verifying an expected effectiveness of the real-time beam sculpting treatment plan using a virtual measurement component of the GUI, where the virtual measurement component simultaneously provides distance measurements and radiation dose deposition measurements associated with the patient's anatomy and the real-time beam sculpting treatment plan;
programming a robotic beam sculpting radiation treatment system to deliver radiation therapy in accordance with the real-time beam sculpting treatment plan; and
performing operations by a real-time beam sculpting radiation treatment system to apply radiation to the patient.

2. The method according to claim 1, wherein the at least one image comprises a Digital Tomosynthesis ("DT") scan, a Computed Tomography ("CT") scan image, a Magnetic Resonance Imaging ("MRI") image or a Positron Emission Tomography ("PET") scan image.

3. The method according to claim 1, wherein the radiation is applied to the patient prior to when a robotic sculpting radiation treatment system is inserted into a cavity formed during a medical procedure.

4. The method according to claim 1, wherein the at least one image is acquired using an X-ray system.

5. The method according to claim 4, wherein the X-ray system:
uses a robotic arm to precisely control a position of an X-ray radiation source relative to the patient;
uses an X-ray detector to obtain multiple two-dimensional X-ray projection images of the patient from a plurality of different angles as the X-ray radiation source is moved by the robotic arm over a predetermined path;
concurrent with obtaining each said two-dimensional X-ray projection image, determines a location of the X-ray radiation source relative to an X-ray detector panel as the X-ray radiation source is moved along a predetermined path by the robotic arm; and
processes the multiple two-dimensional X-ray projection images and the determined locations in a computer system to perform a digital tomo synthesis reconstruction in which section or slice images of the patient are reconstructed from the multiple two-dimensional X-ray projection images that have been acquired;
wherein the X-ray radiation source is moved along the predetermined path by selectively controlling a plurality of joint positions associated with a plurality of joints that are respectively associated with the robotic arm.

6. The method according to claim 5, wherein the X-ray system further:
uses the robotic arm to reposition the X-ray radiation source with respect to the patient so that the X-ray radiation source is disposed at a treatment location with respect to the patient; and
activates the X-ray radiation source while the X-ray radiation source is at the treatment location so as to carry out a therapeutic X-ray treatment of the patient.

7. The method according to claim 6, wherein the therapeutic X-ray treatment is an intra-operative radiotherapy treatment.

8. The method according to claim 7, wherein a deformable image fusing operation is performed in which a pre-operative volumetric imaging of the patient is deformably fused with the multiple two-dimensional X-ray projection images obtained using DT.

9. The method according to claim 6, wherein the X-ray radiation source is controlled to produce a first X-ray beam pattern for purposes of obtaining the two-dimensional X-ray projection images, and a second X-ray beam pattern for purposes of the therapeutic X-ray treatment.

10. The method according to claim 6, wherein the X-ray radiation source is controlled to generate an X-ray beam having a first X-ray beam intensity for purposes of obtaining the two-dimensional X-ray projection images, and a second X-ray beam intensity for purposes of carrying out the therapeutic X-ray treatment, the first X-ray beam intensity different as compared to the second X-ray beam intensity.

11. The method according to claim 5, wherein the predetermined path defines an arc which has a central angle of between 15° and 40°.

12. The method according to claim 1, wherein the deformable image fusing operation is performed after the medical procedure has been performed on the patient, but immediately prior to performing an intraoperative radiation therapy procedure on the patient.

13. The method according to claim 12, wherein the deformable image fusing operation comprises fusing the pre-operative volumetric imaging with an intraoperative DT imaging to combine a higher quality pre-operative volumetric imaging, with a lesser quality but more current results obtained using the intraoperative DT imaging.

14. The method according to claim 13, wherein deep learning techniques is used to guide the deformable image fusing operation.

15. The method according to claim 1, wherein the expected effectiveness of the real-time beam sculpting treatment plan is verified using a 3D sculpted beam tool in addition to the virtual measurement component.

16. The method according to claim 15, wherein the 3D sculpted beam tool presents a cross sectional anatomy of the patient together with isospheres and a radiation source.

17. The method according to claim 16, wherein the rendered 3D isospheres present a distribution of radiation forming a shape of a beam inside an anatomy of the patient.

18. The method according to claim 17, wherein the 3D sculpted beam tool allows a user to see how a dose or beam will be distributed inside the patient during a treatment, or allows the user to perform fine tuning of a position and orientation of radiation sources if any correction is required for more accurate delivery of radiation.

19. A system, comprising:
a processor; and
a non-transitory computer-readable storage medium comprising programming instructions that are configured to cause the processor to implement a method for radiation therapy, wherein the programming instructions comprise instructions to:
cause at least one image of a treatment area to be acquired using a robotic sculpted beam radiation treatment system;
cause the at least one image to be presented in a Graphical User Interface ("GUI") of a mobile computing platform;
create a real-time beam sculpting treatment plan for a patient based on user inputs facilitated by the GUI;
receive a user input indicating that an expected effectiveness of the real-time beam sculpting treatment plan has been verified using a virtual measurement component of the GUI, where the virtual measurement component simultaneously provides distance measurements and radiation dose deposition measurements associated with the patient's anatomy and the real-time beam sculpting treatment plan;
cause a robotic beam sculpting radiation treatment system to be programmed to deliver radiation therapy in accordance with the real-time beam sculpting treatment plan; and
cause operations to be performed by a real-time beam sculpting radiation treatment system to apply radiation to the patient.

20. The system according to claim 19, wherein the at least one image comprises a Digital Tomosynthesis ("DT") scan, a Computed Tomography ("CT") scan image, a Magnetic Resonance Imaging ("MRI") image or a Positron Emission Tomography ("PET") scan image.

21. The system according to claim 19, wherein the radiation is applied to the patient prior to when a robotic sculpting radiation treatment system is inserted into a cavity formed during the medical procedure.

22. The system according to claim 19, wherein the at least one image is acquired using an X-ray system.

23. The system according to claim 22, wherein the X-ray system:
uses a robotic arm to precisely control a position of an X-ray radiation source relative to the patient;
uses an X-ray detector to obtain multiple two-dimensional X-ray projection images of the patient from a plurality of different angles as the X-ray radiation source is moved by the robotic arm over a predetermined path;
concurrent with obtaining each said two-dimensional X-ray projection image, determines a location of the X-ray radiation source relative to an X-ray detector panel as the X-ray radiation source is moved along a predetermined path by the robotic arm; and
processes the multiple two-dimensional X-ray projection images and the determined locations in a computer system to perform a digital tomo synthesis reconstruction in which section or slice images of the patient are reconstructed from the multiple two-dimensional X-ray projection images that have been acquired;
wherein the X-ray radiation source is moved along the predetermined path by selectively controlling a plurality of joint positions associated with a plurality of joints that are respectively associated with the robotic arm.

24. The system according to claim 23, wherein the X-ray system further:
uses the robotic arm to reposition the X-ray radiation source with respect to the patient so that the X-ray radiation source is disposed at a treatment location with respect to the patient; and activates the X-ray radiation source while the X-ray radiation source is at the treatment location so as to carry out a therapeutic X-ray treatment of the patient.

25. The system according to claim 24, wherein the therapeutic X-ray treatment is an intra-operative radiotherapy treatment.

26. The system according to claim 24, wherein the X-ray radiation source is controlled to produce a first X-ray beam pattern for purposes of obtaining the two-dimensional X-ray projection images, and a second X-ray beam pattern for purposes of the therapeutic X-ray treatment.

27. The system according to claim 24, wherein the X-ray radiation source is controlled to generate an X-ray beam having a first X-ray beam intensity for purposes of obtaining the two-dimensional X-ray projection images, and a second X-ray beam intensity for purposes of carrying out the therapeutic X-ray treatment, the first X-ray beam intensity different as compared to the second X-ray beam intensity.

28. The system according to claim 23, wherein the predetermined path defines an arc which has a central angle of between 15° and 40°.

29. The system according to claim 28, wherein a deformable image fusing operation is performed in which a pre-operative volumetric imaging of the patient is deformably fused with the multiple two-dimensional X-ray projection images obtained using DT.

30. The system according to claim 29, wherein the deformable image fusing operation is performed after the medical procedure has been performed on the patient, but immediately prior to performing an intraoperative radiation therapy procedure on the patient.

31. The system according to claim 29, wherein the deformable image fusing operation comprises fusing the pre-operative volumetric imaging with an intraoperative DT imaging to combine a higher quality pre-operative volumetric imaging, with a lesser quality but more current results obtained using the intraoperative DT imaging.

32. The system according to claim 31, wherein deep learning techniques is used to guide the deformable image fusing operation.

33. The system according to claim 19, wherein the expected effectiveness of the real-time beam sculpting treatment plan is verified using a 3D sculpted beam tool in addition to the virtual measurement component.

34. The system according to claim 33, wherein the 3D sculpted beam tool presents a cross sectional anatomy of the patient together with isospheres and a radiation source.

35. The system according to claim 34, wherein the rendered 3D isospheres present a distribution of radiation forming a shape of a beam inside an anatomy of the patient.

36. The system according to claim 35, wherein the 3D sculpted beam tool allows a user to see how a dose or beam will be distributed inside the patient during a treatment, or allows the user to perform fine tuning of a position and orientation of radiation sources if any correction is required for more accurate delivery of radiation.

* * * * *